USOO5753488A

United States Patent [19]
Martin

[11] Patent Number: 5,753,488
[45] Date of Patent: *May 19, 1998

[54] ISOLATED STEALTH VIRUSES AND RELATED VACCINES

[76] Inventor: William John Martin, 1634 Spruce St., South Pasadena, Calif. 91030

[*] Notice: The portion of the term of this patent subsequent to Jun. 5, 2015, has been disclaimed.

[21] Appl. No.: 465,388

[22] Filed: Jun. 5, 1995

Related U.S. Application Data

[63] Continuation-in-part of Ser. No. 157,811, Nov. 23, 1993, which is a continuation-in-part of Ser. No. 887,502, May 22, 1992, abandoned, which is a continuation-in-part of Ser. No. 704,814, May 23, 1991, abandoned, and Ser. No. 763,039, Sep. 20, 1991, abandoned.

[51] Int. Cl.$^6$ ............................................. C12N 7/01
[52] U.S. Cl. ................................. 435/235.1; 435/240.2
[58] Field of Search .......................... 435/239, 240.2, 435/240.25, 5, 235.1; 436/63

[56] References Cited

U.S. PATENT DOCUMENTS

| 4,629,783 | 12/1986 | Cosand | 535/324 |
| 4,683,195 | 7/1987 | Mullis et al. | 530/324 |
| 4,683,202 | 7/1987 | Mullis | 435/91.2 |
| 4,889,818 | 12/1989 | Gelfand et al. | 435/194 |

FOREIGN PATENT DOCUMENTS

| 9220787 | 11/1992 | WIPO | C12N 7/02 |

OTHER PUBLICATIONS

Plotkin et al., "Protective effects of Towne Cytomegalovirus vaccine against low-passage cytomegalovirus administered as a challenge", J. Infect. Dis. 159(5): 860–865, May 1989.
Cowley et al., "A chronic fatigue cover–up", Newsweek, Apr. 22, 1996, p. 62, Apr. 1996.
Ehrlich et al., "Detection of Human T–Cell Lymphoma-Leukemia Viruses," PCR Protocols: A Guide to Methods and Applications, Ch. 39, pp. 325–336 (1990).
Feinberg and Vogelstein, "A technique for radiolabeling DNA restriction endocnuclease fragment to high specific activity," Anal. Biochem. 137:266–267 (1984).
Freshney, "Ch. 10—Maintenance of the Culture–Cell Lines," Culture of Animal Cells: A Manual of Basic Technique, Alan R. Liss, Inc., New York, pp. 127–136 (1987).
Gupta and Vayuvegula, "A Comprehensive Immunological Analysis in Chronic Fatigue Syndrome," Scand. J. Immunol. 33:319–327 (1991).
Ham, R.G., "An Improved Nutrient Solution for Diploid Chinese Hamster and Human Cell Lines," Exp. Cell Research 29:515–526 (1963).
Ho, M., Cytomegalovirus: Biology and Infection, 2nd ed., pp. 75–76, Plenum Medical Book Company, New York, N.Y. (1991).
Holmes, G.P., "Defining the Chronic Fatigue Syndrome," Reviews of Infectious Diseases 13(Suppl. 1):553–555 (1991).

Holmes et al., "Chronic Fatigue Syndrome: A Working Case Definition," Annals of Internal Medicine 108:387–389 (1988).
Iscove and Melchers, "Complete Replacement of Serum By Albumin, Transferrin and Soybean Lipid in Cultures of Lipopolysaccharide–Reactive B Lymphocytes," J. Exp. Med. 147:923–933 (1978).
Kendell, R.E., "Chronic Fatigue Viruses and Depression," The Lancet 337:160–161(1991).
Landay et al., "Chronic Fatigue Syndrome: Clinical Condition Associated with Immune Activation," The Lancet 338:707–712 (1991).
Martin, W.J., "Ch. 27—Detection of viral Related Sequences in CFS Patients Using the Polymerase Chain Reaction," The Clinical and Scientific Basis of Myalgic Encephalomyelitis/Chronic Fatigue Syndrome, pp. 278–281, Hyde et al. eds., The Nightingale Research Foundation, Ogdensburg, New York (1992).
Martin, W.J., "Ch. 34—Viral Infekction in CFS Patients," The Clinical and Scientific Basis of Myalgic Encephalomyelitis/Chronic Fatigue Syndrome, pp. 325–3271, Hyde et al. eds., The Nightingale Research Foundation, Ogdensburg, New York (1992).
Martin et al., "Cytomegalovirus–Related Sequence in an Atypical Cytopathic Virus Repeatedly Isolated from a Patient with Chronic Fatigue Syndrome," The American Journal of Pathology 145(2):440–451 (1994).
Niks and Otto, "Towards an Optimized MTT Assay," Immunological Methods 130:149–151 (1990).
Palca, J., "On the Track of an Elusive Disease," Science 254:1726–1728 (1991).
Palca, J., "Does a Retrovirus Explain Fatigue Syndrome Puzzle?" Science 249:1240–1241 (1990).
Rethwilm et al., "Infectious DNA of the Human spumaretrovirus," Nucleic Acids Research 18:733–738 (1990).
Sanger et al., "DNA sequencing with chain–terminating inhibitors," Proc. Natl. Acad. Sci. USA 74:5463–5467 (1977).
Schirmer et al., "Differentiation Between Two Distinct Classes of Viruses Now Classified as Human Herpesvirus 6," Proc. Natl. Acad. Sci. USA 88:5922–5926 (1991).
Shafran, S.D., "The Chronic Fatigue Syndrome," The American Journal of Medicine 90:730–738 (1991).

(List continued on next page.)

Primary Examiner—James Ketter
Assistant Examiner—Iran Yucel
Attorney, Agent, or Firm—Lyon & Lyon LLP

[57] ABSTRACT

An isolated stealth virus that is positively correlated with chronic fatigue syndrome is provided from a patient having a disease. Examples of diseases the patient may have include multiple sclerosis, unexplained encephalopathy, acute encephalopathy, psychiatric disorder, Alzheimer's disease, fibromyalgia, myositis, muscle neuritis, chronic pain syndrome, salivary gland enlargement, autoimmune disease, and unexplained hepatitis. A vaccine having an isolated stealth virus or antigen is also provided.

1 Claim, 24 Drawing Sheets

OTHER PUBLICATIONS

Shepherd, C., "Myalgic Encephalomyelitis—Is It a Real Disease?" *The Practitioner* 233:41–46 (1989).

Wang et al., "Single primer–mediated polymerase chain reaction: application in cloning of two different 51–untranslated sequences of acidic fibroblast growth factor MRNA," *DNA Cell Biol.* 10:771–777 (1991).

Welch et al., "Cytomegalovirus Homologs of Ceullar G Protein–Coupled Receptor Genes Are Transcribed," *J. Virology* 65:3915–3918 (1991).

Werner, J., "Isolation of Foamy Virus From Patients with De Quervain Thyroiditis," *Lancet* II:258–259 (1979).

Yousef et al., "Chronic Enterovirus Infection in Patients with Postviral Fatigue Syndrome," *Lancet* i:146–150 (1988).

Ablashi et al., "Genomic Polymorphism, Growth Properties and Immunologic Variations in Human Herpesvirus 6 Isolates," *Virology* 184:545–552 (1991).

Ablashi et al., "Utilization of Human Hematopoietic Cell Lines For the Propagation and Characterization of HBLV (Human Herpesvirus 6)," *Int. J. Cancer* 42:787–791 (1988).

Ada, "Vaccines" in *Fundamental Immunology*, 2nd edit., Paul ed., Raven Press, Ltd., New York, pp. 985–1032 (1989).

Archard et al., "Postviral Fatigue Syndrome: Persistence and Enterovirus RNA in Muscle and Elevated Creatine Kinase," *The Royal Society of Medicine* vol.81 (1988).

Buchwald et al., "A Chronic Illness Characterized by Fatigue, Neurologic and Immunologic Disorders and Active Human Herpesvirus Type 6 Infection," *Annals of Internal Medicine* 116:103–113 (1992).

Chee et al., "Analsyis of the Protein Coding Content of the Sequence of Human Cytomegalovirus Strain AD169," *Current Topics in Microbiololgy and Immunology* 154:126–169 (1990).

Cohen et al., "Okadaic Acid: A New Probe for the Study of Cellular Regulation," *TIBS* 15:98–102 (1990).

Dale et al., "The Inoue–Melnick Virus, Human Herpesvirus Type 6, and the Chronic Fatigue Syndrome," *Annals of Internal Medicine* 110:92–93 (1989).

Dale et al., "Chronic Fatigue Syndrome: Lack of Association with Hepatitis C Virus Infection," *J. Medical Virology* 34:119–121 (1991).

DeFreitas et al., "Retroviral sequences related to human T–lymphotropic virus type II in patients with chronic fatigue immune dysfunction syndrome," *Chemical Abstracts* 114:No. 205331c (1991).

DeFreitas et al., "Retroviral Sequences Related To Human T–lymphotropic Virus Type II in Patients with Chronic Fatigue Immune Dysfunction Syndrome," *Proc. Natl. Acad. Sci. USA* 88:2922–2926 (1991).

Demitrack et al., "Evidence for Impaired Activation of the Hypothalamic–Pituitary–Adrenal Axis in Patients with Chronic Fatigue Syndrome," *Journal of Clinical Endocrinology and Metabolism* 73:1224–1234 (1991).

DiLuca et al., "The Replication of Viral and Cellular DNA in Human Herpesvirus 6–Infected Cells," *Virology* 175:199–210 (1990).

Plasmid: 1

```
GAATTCTGGT ATGAGACGGA CGGCACGCCG GTTCAATCCC GGAAATTATT        50
ACAATGTCGG CGGCAATTCC AAATTCTATG GCGCAGTGCT GGTGCGCTAT       100
CGGCGAAGAT TTGAGGAGC TTGCGCATCT TGAAGGCGTG TCTCCGGCAT        150
GGCCTTTTGG      SEQ ID NO. 7                                 160
```

Plasmid: 2

```
TANGTACACN CNCTNGAGCT CTCGCTNTCT AGTAACAAAG GCTCAGTACG        50
TGGNAAGGGG TGTNGCGTCA CGCCTACACA CCTGGGCTGC TCGACCATCA       100
TAACGTGTGT GATCTGGAGG GGCCTTCTAN ACCTGTCGTN GNTGNGGACC       150
CCNCAGNTTT NTATCNGTAG CATACTNACN NAACGCTCTA CCNCNTCNAC       200
ATTTGANNCN TTCCTATTTT TTTCCCCCCA CACTTTTTNT TTTTCANTTT       250
ACCTCTNANC TANTTTCCNA CATTCTNCNN NNNNCATNTC TNCATCCCCC       300
ACTAATNTTC TTCANTCNNT TATNNATCAA NCCNCNNTCN CACNTTNCCA       350
TTNCAACCAC CNANNNTNTT ANCTCNCTTA NNNTTTCTCC TTNNNACTAT       400
CAATCTTNTN TNACTNNACA CCNANCACTC NAANCTCCAT TTTTAAANNN       450
TNNANNTNTC NTNNCCNTTN TNTAACCCNC TTNANCNTAC NTCNNTAATT       500
NCTTTTCCNA ANATTNANNC CNCACCNANT TATNNNTCAC CANNCAACAT       550
NTNNTATNTC TANNNNANNN TTNTTTNNCN TAAACNTCCT ACTTCTANNT       600
NTNCANNTAA TANAATNCTA NACTNCTCAC CTTNAACNNC TNCACTNCAN       650
ACNTNACNNN NTCNNNTTTT AAACTNCNNT NNTNNNTTTT TANATCCCNT       700
CTCACTTNAT CTNATAANNC NNATCCATNT TTGNCCNCTC ATCTATCNTA       750
CTNNNNACNC NTNNCTNCCN TCTTNCTCAT CCAA      SEQ ID NO. 8      784
```

Plasmid: 3

```
TGTTTTNCAN CTTCTCAAGG GACCCCCCCC CGAGGAAGAC GGTATCGATA        50
AGCTTGATAT CGAATGCCCT GCAGNCCGGG GGNATCCACT AGTTCTAGAG       100
CGGNCGCCAC CGNGGTGGAG CTCGAGACAG GTGNCGCGAT ATGCCNCGGC       150
CTGGCACCGC GAACACAGCG GCCCCTGGCC GTGACACGTG AGCTTCAGGA       200
GTCGCGGGAT AGTGACGGAG CGCACCACCA CGGTGGAATC GCACGTCCGC       250
GCAGAGCACG GTAGAATGAT GTCAAACGTG ACGAGGTGGT CATAGACCGC       300
ACACGCGGTG TTCANCCCCA AGACTGNCTT CCAACCAAAC CGNAAACAAC       350
GTTGCCCACA NATCGTCTCA GAGACANCTT CGTAAACACG TTCTTTTAAT       400
GACACGCTGA CTTCCACAAA AGAGAACAGT GCANCAGTTC GGCGTTAGTA       450
TTGAAANTGA CACTCTTTTC TTGGCGGTCT CTATANTAGA ACATAGAGTT       500
AAGGGGGGAA TTCTGCTCGC AGNGNAGGTT CTCCTGGCCA AGTTCAAGCA       550
GGGGNCGAAT TCGGANAAC ACGGNGACAG GATCTTGGTT TAGTGGNGTC        600
NACTCAGNGA AAAGCACAGG NGGTTTATAC GTTCTTTNTC CCGAGNCNCC       650
ATCTATATTT GGTGTCNGGC CCNTTTTTT     SEQ ID NO. 9             680
```

Plasmid 4:

```
GAGCTCGCCT CTGGCTGCAC CTGTGGGGGG CTCTTTCCAT GTCCTCACAC        50
GTCTCTGTCA CGTCCGCCCT CGTACAGNAT CACCGCTCTC CTAGCTTTCC       100
CAATTTTGNG GTCAAACACG TCACAATTAC ACTGCGTCAA CCACCTGCCC       150
GCGAGCCATT CACACGGTAC TTATGAGAGC GACAGGTAGN CCCTTGNCAG       200
TCCCGTCAGT CTTGCCCCAA TAGAAGCCAT CACAGACACT GTCCATCACA       250
GNCCATCTAA ATTACANCAT NACATTATTC ACACCGAGAC GANCNANNNG       300
GCTCGTNGTG ATGATCGAAN TTTGNGATCG CNACTGCGGT GANCAGTTGC       350
AGATCGAACG GNTGAGGACG TCGTNGTAGA CAGGAGTNTC GNCAGNGCAA       400
ANCTTACTGN TNGGCANCGG CCGANTGANG CCGANAGCCA NAGACCGACG       450
TCTCGANTCA ATTCAAACAA AGACGTCCGG TAGCAGGGTC CGTAAATAGG       500
GCTGCGTTAA AACNCNTGNC G      SEQ ID NO. 10                   521
```

*FIG. 1A*

Plasmid 5:

```
GAGCTCCATC TGTGTGACGT TAATCTCCAA ACACCCTTCA AAGAAATGCA       50
CGAACAGTTA AGTTACCTGA TTACAGGACA CACCTCAACC ANCTCCATGT      100
CCTTTTCCGA CGAGCTGCTT CAACTACGCT CACAGTTCAC GTACGCTACT      150
CAGGTAAAGG AAGACACCGA AAGCAAAATC CATGACCTGA TGCTCAACAT      200
CGAAACCGNC ATCCAGGAAC CTACCACCCG CAGCTCCAAT ATCGNCATGG      250
NCATGGTCCA AGAACAGCTA AANGAACTTC AACAGCTCGG AGGNGCCANC      300
ATCCCTGAAA TAGCTACCCG TCTGGAAAAG GTACACAAGG TGTTGAATTC      350
CCTCCAACAN GAAGNACAGG GGGGCAGAGT CTTCGTCAAC GGGCTAAATT      400
ATGACACTTA CCAANCGATC AANCACTCAN NAGACANGCG GGCTTTCAGA      450
CTGNTGGGGA GGNGGCAGCT CACGAATTTC ATCCAGAANT CNGGTTTTTT      500
CAAACCTCTG GCCT       SEQ ID NO. 11                         514
```

Plasmid 6:

```
NGNTTGACAC TNTTAAGCTC GATGCCNACA TAAGCTGACG GNGACAAACC       50
AGGAGCGGGT ACAGACACCG AGGACGATTT ACGCGCGCGC GATGCACAAG      100
CTCTTGGGCT ACCGGCCAAC GCCGGCTGCA ATGCCCGTCN GAGCGACCTG      150
GGTCAGCTGA GTCGTGCTCT ACGTTGCGAT TGGCGATACT GGCGACTCAC      200
TACTGCCCCG GAAGAATACG AAGACCCCGG TGAAGACGAT TCTTATAGCG      250
AGTTACCATA CCGCACGTNG GNTCCCANCG ANTATNACNC TCAGTGNNAT      300
CCANAGATCG TATTCGGNNC AANCACAACC GTCGCTNGCC GACTGTNTCA      350
TCACCGAGCC AGNGTCGGTN GACCCCTNCA CGCCCCCCCC CNCNCCCCCT      400
TTTAGCCNNC CCTCCCCCCG NNCNCNTGTC CACCCCCCCC CTANCCAAGN      450
NCCCCCCCGC CNNCCCTNCN CCNTNCCCNT NNTTNAGNTT CTTTTCAAGT      500
CTTTCATATT TCTNNATTNN CNCCTTTTCA TTTCGATGNA GGAANCTNCG      550
TNNNGNTTTG NNNTTTCTTC CNGCCTANGT TGTTTNANNT TTTTNTTNNN      600
CNNTTNNNTA NAATCCNGAG NNNNTTNCTC NCTTTANTNT CGTATTTNTG      650
AAANTGTTTT TCACCCCCCC A     SEQ ID NO. 12                   671
```

Plasmid: 7

```
GAGCTCTGCC GGGCGTTTGG AGGTGAACAG TTTGACCGGC TGCTCCGTGA       50
CTGATGGCCG CAGCGGCGGC CGACGGGTTA GGATATTGAC GACCTAACAG      100
TTCAGTTATG TGAGGAGGAT NAGTTGTGAG CGGTGAAATC ATAGTACACA      150
GGTACAGGCG AGGGATATCG CCGNAGCCGT ATTTCCAGAA CTCGTCAGCA      200
TCGGTGGNCA CGAGATGCAG AGTTAGTCGA GGAAAGTCGA GAAGAAAAAC      250
ACNGAAGTGG GGTCCNAGAG CGANGTNCAG NNCTNCATNN TGACAGATAG      300
TTGNTTGANA NNCANNGCCA GNAGTNGTTT CCTTNCACNA TNCANGNCAA      350
TNTAANANCC NCCCANTNCG TCNTTTTGNT NNACANTTNN CCGNANTTCC      400
AANNTNNNCC CACCNNTTNN NCNTTTNCNT NNCCNNNNNT TNNTCNTTTC      450
AATATNACCC NNCCNNNNCN TCTATTCANN NNTNTNNNCN CCTCTCCCNT      500
CNNAACNNTT TNTNNTNNTN NNTNNTNCNC TTCNNACNNC NTCCCTCCCC      550
ATCCNTCNAN CNNNNTNCNC NTTTNNCNNN NNNTTTTTTT TTTANTNNTC      600
CCATTNNTCN TCNTTA    SEQ ID NO. 13                          616
```

FIG. 1B

Plasmid: 8

```
GAGCTCTACT AGACGCGGAG AGACGCGTTC GCGACGGAAA AATTCCGGTA       50
CCCTTTGTGG ATCGCGATAG CCTGTTGGCC AACGTTATTC CCGTCGCCCC      100
CACTCCCAAT CCGGAAANTN NAGGAAGACC GGAGAAGAAA GCACTGACAC      150
GACAGTGTTC GNTCCCTACC CCCCACCCTA AGAAGTTCGG AGTNCAGCCT      200
GATTCCGATA GCGACAGNGA TACGATTATC GATTCAACTA TGGAAGGNGC      250
GGNATCTCTG TAGATTTTTT TTTTGNTGAA TTGNGCAACC CGCANTNGCT      300
TGGTGTNACT GTAGACAAGN CTNCTNTNAA TCANTAGTNT TNNTTTNGTA      350
ATAAAACNGN TTNGTTTNNT TTAATCCACN NAGTNGCNNT GTNTTAATCT      400
TNNTTGTGGG NTGATNAGNN CCNNCCCNCN NCTTTNACTA ANTNNTTNTA      450
ANTTNGNNNN TNNACNNNNT NTNNTNTNTN TNTTCCCNNT NTNTNTCCCC      500
NCTTTNNNNT TNNNNTTNNN CNTNNTTNTT NCNNNCCNTC TNTNTNTNNN      550
CNTTTNCNTT ATCTNNTCTC NCNTATTNTN NNCCCCTCNC NTCNCNNTTN      600
T       SEQ ID NO. 14                                       601
```

Plasmid: 9

```
GAGCTCCTAC CCTGTGCCCT TATACCATTC TAGGCACTTT ATTTTTTACA       50
TGGCTTGCCT CTGTTAAATG TCACCGTAAC TCCCAGATAA CCTCTTCTGA      100
TAGCTGGGAA AACCAAAGCA CAGATTGGTT TATAAACTTG CTCACACAGC      150
TAGCATCAGA GAGACCTGGG ATGTCTCATC ATTTCTGTTC TCGTATCAAA      200
GAGGGCCCTT GTGAGCCTCT CAGTTGGCCG ATCCTAACAC TGGTCAATTG      250
GAATCTACTC CCCAATGTTC CAAGGAATGG ATGTCATGAA CCATGGNAGG      300
TGGNATGGNT GCTGGAATCC AGNNNGGTC CAGGTGANGN CTCAAGCCAT       350
ATTGNAGGTT GGCCTCAAGA NTTTGGCCTC CCCATNGGGT TATGATGNNG      400
GGGGTTNCAT NTTTCACCAA ATTNGNAANT TTNGGNCAAN TCTTTCTTTT      450
ANNNAAAANT NTTGGNCTCA CCNGGNAANA AANANNAAAG GGGGGAANNN      500
TNNNNNNTNN GGNTTTNGNN NNNNTTCCCN NTNCTNTTTT TANNNNGNNN      550
NNNNNTGGGG NNNANNNNNT NNCCCCNNNN TCNNNNNAAA       SEQ ID    590
NO. 15
```

Plasmid: 10

```
GAGCTCCTCG GTGGGACAGA GCGTANAGGC TGGAGTGCTC GGGGCGCTTC       50
GTGACATTTT ATATCAATAC GCTGACAACG ATGAGTATGG GCTATACGTG      100
GACTGGTACG TCACGGTTGG AATCATCCCT CTGATGGATG TCAAGTCTAA      150
ACCCGCCGAC ATCACGCAGC GCGCAGGCTT CGTCCGAGCC GCAATCCACA      200
GAGCCACAGA GACTCACCCG CTAGCTCAAG ATTTACTGAC CGNTAACCTT      250
CCCGCTTCTG CAGNAAGTGN GTAACGCATC TTNTNCGCGG GTCCCCAATC      300
GTTANCTCCC CCGNAGNTNN CGGATCTTCA AACGAATCCC CTCCGGNAAA      350
GATTGNNGNG CANCCTANNT GAAAAGCATA CCCGCNGCTA TNTTCTTACA      400
GANCCNNTTN GCCTNNNAAC GNNAACANNT TNTTCTTCAN CNNCCCCATC      450
GNCCCACCTT CAGNAAGANA TTTNGGCGTT NACGAATNCC TNTTTNCCTC      500
ACNAGNAGTT CTTCCNATTN CNTNNNAANT NTTCANTCAA GCCCNCACCN      550
CNCCCCNTNN TTTACTTAAA AATCNCCNNT CTGNAANCAC NCCCNGAGCN      600
ATTCNANNNN NCCCANAACT NTTTTTNTCT TNTCCNN    SEQ ID NO.      637
16
```

FIG. 1C

Plasmid: 11

```
GAGCTCCTCG GTGNGACAGA GCGTACAGAC TGNAGTGTTC GGCGNGTTNC        50
GNGACANTTT CTATCAATTN GCTGACAANG ATGACTANNG NNNTATTCNT       100
TTNCNTGNNA CNTTATTTTT TNANNTNAAC CCCACTTATN NTTCNCATAT       150
NCTCTNACNN NNCTNANATC AACCTNATNA ATCTTCCNAT ANTNCTNNT        200
CTTACTACCA TTTTNCTNCT NGATTNTCCN ATTTNCNTTC CACTTNTNTT       250
ANNNTCCANN TTTNCTACTN CNANTNNCNT TTATNCNCNC TCCATCTCTN       300
TTTCCCTCAT NNTCNACTTT TNATANTNCN CTTNACNNCT CNNACNCTAT       350
NNTTTNNACC TTCCANCTAN NCAATCNTNT ATNNCTTTNT ATTAATTNCC       400
TAANCNCNCC TTNNCCNNTN NANTCAAAAT TNCACTATTN NATTTATNNA       450
CNCNTNTTNN TTNCTANTNN CACTCATCNC TCTAAATTNN CNNCTANNAN       500
TTATNTCAAA TNTANTCTTT NTNTATTTAA NATNATCTCA CCNATTTCTC       550
TTATACNCNA TNTNNNANNN CATTTNTANT TAAAANTANA NTATTTTNTT       600
TNTTNTNNTN NNTTNTCNCT CNCATCTNAC ANNNTTTANA NTNCAANNTT       650
TTTNNCCTTC TATCANATN       SEQ ID NO. 17                     669
```

Plasmid: 12

```
GNNTTTGACA AAGCCCGTNG TCACAAACGT CNCGGAGACN AGTCGGCGCT        50
CGGGACTCAC ATCCACCGAC TCATTGCGCT CTTGGATCAC GACAACCATC       100
GCGAACTGTG CAATGTGCTG GTCGGGCTGC TACACCAAAC ACCCCACATG       150
TGGGNCCGNT CCATCCGTCT TATCGGTCGA TTAAGAAACT ATCTACAACA       200
GAAGTTTCTC AATATCTTGG TGGATAGNGG NCTCCAGATC GATAGTCTTT       250
TTGAGGGTTG GTTACCACAG CGAAGCGTAC CGCTTGCTGT TCCAGATCGA       300
AAAAACGAAC TCCACGCCTA GCTCTCTAGC CTGTGCAAGC ACCGNNTTAC       350
CTGTCGGTGA AAACGAAACT GAAGGNACAC CTNGNNCCGC CCNNGTNTTT       400
ANTGAAATAA TAATATGGGT NCTCAANGAA TAAGANGGGG CTTTTNTTTC       450
GNNNNNGGTN NGACAANTNT NANTCTTCCN CCCNATNCAA TNCCTNNCTG       500
GCCCGTNNNN TTCGNCTCCN NTTCNTTTNT CTTNGGTCCT GTNNTTTNCT       550
CATNNNCNNN ANNTCCTCCT NGNNCTNCTC CCCTATCNTC NNNCTNNTTT       600
TNNNTNNCTC NCCNNNNNNT CNTNTCNCTN TCNTCNTCTN TNNCCNNNNT       650
NTTCNNTCTT NCCCTTCTCT TNNTNNNTTN NTTCNNCTCT NNTNTNTCNT       700
TTNTNCNTTN TCTCC       SEQ ID NO. 18                         715
```

Plasmid: 13

```
TTTTTTTNNNN NNTTTTTTTN CGCACCNNCG CAATTAACCC TCACTAAAGG       50
GAACAAAAGC TGGAGCTCCA CAGCTTTCCC TTGGCATGGA AAGGGCCAGA       100
AGAGCCAGTG GAAGGGACCT GCCATGCTAA GGGGCGAGGT GACCCCATGA       150
TGAAGGCCAC AGAGTGTTTA ACTTAGTAAG GGTCAGGTGG AGGGTGCATC       200
TGAAGCTCAG AAGGCCGAGC AGAGCAGTGA GGAGCTGGGA TGGGGCAAGT       250
CGGCAAGGGA AGAAGACAAA TTTCAGGTTC ATCTCCATAC TCCGGGAGAG       300
AAAAGCCAGA AGTAGNCCAT GGACCAGGCG TCTCTGNCTC TACCTCCTGC       350
ACCTTCTCCA GTTCCAGNCA CTCCCGNTCC CCCTTCACTG NAGNCACAAC       400
CAGACTCCAG NCCTCCAGNN NTGNCTNGNT GCCTNNGGNC CACAGNNCTC       450
CCNNACCTCC CNTCTCTCCT CCNNNNTCAN ANTCANNTTC CNNNATCTTC       500
CTTNNNNTTN GNNCANNNNC CNNCTCTCNT CATNCTCTNT NNNNNTTNNN       550
NNNTNTTCAN NNNNCTNNGN NNNNNNNNTT CNNNNTTNNN TNNNNNGNAN       600
NNCNTNNNNA CCNNTTCCNN NNNNNNNNNN NNNNNNTCNN NNNGNANNN        650
NNNNTNNNNN NNNNNTNNNN TNNNNNNNNN NNNNNCCCNN NNNNNNNNNN       700
NNNNNNNNNN NCNNNNNNNN TNNNNNNNNN NNNTNTT       SEQ ID NO.    737
19
```

FIG. 1D

Plasmid: 14

```
GGTTTNGNAA CTCTTGAAGC TCTCGNTCCC CTAGAAACAA GGCTCAGTAC         50
GTGGAAGGGG TGTGGCNTCA CGCCTACACA CCTGGGCTGC TCGACCATCA        100
TAACGTGTGT GATCTGGAGG GGNTTCTTTA CCTGTTGTGC TGCGGACCCC        150
GNAGTTTCTG CTCGCGGNAC ACGTGTTTCG GGCGGGAGAA GCACGGTTGA        200
CCATTCCCCG CCCTGCTCCC CAAGGATCTT TTACGAGCCC GNTCGCGATT        250
ATATGACGNA TGTGAACCTG GCTGAACTTC TACGTTTATG TGTGGNATCG        300
CGGCTATGAT CGCCCTTCGA CTTCGGATCC NACGCAGGG GNTGATGACG         350
ACCGANCTNC NGNCNGNCTT TTAATAGANC CGCCCTCNCN TNCNCACCNN        400
TCTCAACAGG ANNTTGCTTA AAAGNCGTGA TCCNANCGNC NGCTTCTTNG        450
GCCGTCNCNA TANTTCNCTC TTCNACNTNC CTNNCTTNNT CCTNACANTC        500
TNNCTTCNTC CNTCNNGCCT CNNTGCACNN CNTATTTCTT CTNCATCTNT        550
TTANCCTCCC NTCNNANTTT NNNTTNNCNA TCACTCCANN CACNNCCNNN        600
TNTTANCCCC CANNTCCCCC CCCATTNTTN NCANCTNCTC CNCTGCCAAN        650
NNCCTNNTTT TTANCCCCNT CTNNCCATNT TTTNCTTNGC TTCNCNTANA        700
TCCANANTCC CCCTNNACCT TACANCTCTN TATCCTCTNA TCCCTCCNAC        750
TATACCCCTT NTTNTATCNT NTCCNCCCC     SEQ ID NO. 20             779
```

Plasmid: 15

```
GAGCTCACAA AACGGTGCTG GTTTGGTTTT TTACTTGGCC CACGGATACG         50
GGGGAGAGGT AGACAGGCCC GACTTCTTTG TTANTCTCCG GGTCGTCGGC        100
GTCCGCCACG CTGGTCAGCA GGTGTTGTTT ACTCTGCACC AATTCCGACA        150
GCGGTGTACT CGCCATCGCG CCCGTGCCCG ACCACATGTN AAAAAGCAAG        200
TACGTGAAGC GCTCGGGGA CGGAGTGCTG TGTTCTGTAA ACATCTGTAG         250
AAGTTGCTTC GGNGCCTCTG GGATTTTCAC AACGATTGTC TGTTTGTGGT        300
GGCTAAATCG CCGGTGTTTG GTGTACGGTA CCGTCTCGTC ACCCATCACC        350
ATGGCTTTTG GACCACTGCC ANATGGCTCA GGGTTATGTT TTCGGTTCTT        400
CCACTGAATC TCCCAACTGC TTTTCGAAGC AGCGATTAAT ANAAAAATGN        450
AGATGGAAAT CAAACAACNT CAANGAAATN TTGTCAAAAA GAGNTNGTCC        500
ACGTGAAGGT CCCNANNNTT CTTGACGCAA AGTATGATTC AACTCGGNNA        550
TNGTNANTNG CAAACTTTAA GGCGCCCNCN NGGCCCATTA NATTANACNA        600
NAGAAACTTC NCCGNATGCC AANTTGTCTT ACTTGTCAAN AGTTTATNNG        650
GAGTTTGACG TTNNTCNAGG GNCAAGTTTT CT     SEQ ID NO. 21         682
```

Plasmid: 16

```
TGTTTTNCAN CTTCTCAAGG GACCCCCCCC CGAGGAAGAC GGTATCGATA         50
AGCTTGATAT CGAATGCCCT GCAGNCCGGG GGNATCCACT AGTTCTAGAG        100
CGGNCGCCAC CGNGGTGGAG CTCGAGACAG GTGNCGCGAT ATGCCNCGGC        150
CTGGCACCGC GAACACGACG GCCCCTGGCC GTGACACGTG AGCTTCAGGA        200
GTCGCGGGAT AGTGACGGAG CGCACCACCA CGGTGGAATC GCACGTCCGC        250
GCAGAGCACG GTAGAATGAT GTCAAACGTG ACGAGGTGGT CATAGACCGC        300
ACACGCGGTG TTCANCCCCA AGACTGNCTT CCAACCAAAC CGNAAACAAC        350
GTTGCCCACA NATCGTCTCA GAGACANCTT CGTAAACACG TTCTTTTAAT        400
GACACGCTGA CTTCCACAAA AGAGAACAGT GCANCAGTTC GGCGTTAGTA        450
TTGAAANTGA CACTCTTTTC TTGGCGGTCT CTATANTAGA ACATAGAGTT        500
AAGGGGGGAA TTCTGCTCGC AGNGNAGGTT CTCCTGGCCA AGTTCAAGCA        550
GGGGNCGAAT TCGGANAAC ACGGNGACAG GATCTTGGTT TAGTGGNGTC         600
NACTCAGNGA AAAGCACAGG NGGTTTATAC GTTCTTTNTC CCGAGNCNCC        650
ATCTATATTT GGTGTCNGGC CCNTTTTTTT     SEQ ID NO. 22            680
```

FIG. 1E

Plasmid: 17

| | | | | | |
|---|---|---|---|---|---|
| GNNTNTGCAC | NTNNTTATAG | GTCTNANTCN | CGTTNAAAAC | ATTTGNGGGT | 50 |
| ACAGCGNTGC | CACCGNCCGA | TGGAGAACGT | GTTGTATGNC | CATNTTCTNC | 100 |
| GNACAGCCNG | GGAGATGATC | TGATGANACA | NGNNCCACTG | ANGAGTGGAG | 150 |
| GANGATNATA | ACGACTACCC | GNCNATTCCA | CAGGTGCGAC | AGGTTCCCCA | 200 |
| GTATCGATCG | TCCATCAGCN | TCGGCTGGNA | CCCACTGANG | GTGANCGCCC | 250 |
| NNATTCACAC | AGTTAAGATG | GCTGAGCAAN | GNNGAGGAAG | ATNACGTCTC | 300 |
| GCTGCACANN | ANCGCCGCAT | TGACCCGTCN | GAAGNNCGGC | ACCATATGGT | 350 |
| GCTNACCCTC | GNNCCCCAGT | CCTGTCGACG | GCTATTGANT | NNNTTNNTTN | 400 |
| AANNCCTTGG | CTTANTGTTC | NTTTGNNCAG | NTTCACGATN | TTCTNNGCCC | 450 |
| CNANTTTTTC | NGGATCCCCT | CNACATCTTA | NATGTTCGNN | TCGTTTTTAA | 500 |
| NAATCCTNCG | GNTTCCCGTT | CNTTTANTCC | ANTCNNTCNT | NCGNNTTNTC | 550 |
| ACNATGNCNN | ACTCNNGTNN | TNTCANTNTA | TTNTTTACAC | GNATCTTTAN | 600 |
| NCTTTTCNCN | CCCATTCCCC | NCNGNCNNCN | ANGTTNTTNT | CANNNNTCCC | 650 |
| NTCNNCGTC | NNCNANCTCT | NCAANCANNA | GCNTCTTTNN | TTGCNCATNT | 700 |
| NGTCNTTGGA | ANCTNTNNCN | TTNNAAGNNN | ANNGTACNNC | CTCTTTNTTT | 750 |
| NANNTNACNC | CANANACANG | NNCATTCTTA | AATCNNCNTT | ACNCCCTTAC | 800 |
| TCCATATCTN | TATCTATANT | TT | SEQ ID NO. 23 | | 822 |

Plasmid: 18

| | | | | | |
|---|---|---|---|---|---|
| GAGCTCATAC | TCCGCTGCTG | AGATGGTGGC | CTGATAGAGT | CGTCTTATGG | 50 |
| CGGTGACGGG | TACGGGTAGG | TGTTCCACCG | AGGTGTGCCG | GGAGGTTGGG | 100 |
| CGTNTCTGCA | GATGGGTTAT | ACACANGTTA | CGANTTAAAC | ATTTGGAGTG | 150 |
| AACGTCTCCG | TCCTTTGGCG | CGCGANTCTT | GTAGGGCGGC | ATCGCGCAGC | 200 |
| ATATAGTTCG | CGATTCGCNA | TTCCTCGTTC | CCCGTCTATC | GTCCATTGGN | 250 |
| NGAGGGNACA | CAGANTATAG | TCTCCNAGGA | CACAAAGCG | TCTAGGTGCC | 300 |
| CTCAACGGCT | CGCAGGNAAA | TCAANAGAGC | CCANNTTNTT | TNCTTCGANG | 350 |
| CAAAGGTTTC | GNCACCCCCG | TCCGTTTATT | TTGTCNCCGA | NAANATGGCT | 400 |
| TCCGCCNGAN | TTTGNTTTGT | TAGTCANTTC | CCGNNGNNGA | GGNGNATTTT | 450 |
| NTNANNTANC | NTTCANATTA | NNTTAANCNT | CNCCAAGCNT | TCTCTTACCT | 500 |
| NTTACNNCNA | ATNCAACCA | AATCATCNGN | TTCCGCTGNT | TAAACTGAAT | 550 |
| NTNACATCNT | TCTCCACTAA | ANCCNNTCNT | NCANACNCNT | NNCCTCCAAT | 600 |
| TCTCCTCANA | ATACCNAATA | NCNCNNCCAT | CCNNCTNANT | TNTGNNTCAC | 650 |
| TCNTT | SEQ ID NO. 24 | | | | 655 |

Plasmid: 19

| | | | | | |
|---|---|---|---|---|---|
| NGTCTTTGNA | CCTTNTCAAA | GATCGAGGCN | CCCCGAAATC | GTTGTGTCGG | 50 |
| GGCTGCGCCT | TGGTGNCCNC | AGACNGNGTG | TCACGGCAGN | AGTCATGTCG | 100 |
| TCTAGCTCGA | GNAACACGGG | TACCAACGTT | ANGAAGGATG | AGGAGNAGCG | 150 |
| GCGCCACGTG | TGTGTGAATG | TATTGGATCT | GCCCCAGGAG | TCCATGGAAC | 200 |
| ACCCCGNGAC | CGGNACCATG | TTGTCCAAGT | ACGTCCGGAT | GTCCAGCTTC | 250 |
| TTTACAGACA | AGTTTGCCTT | TAAGCTGGAC | TTACTGCGCA | TGTTGGCGGT | 300 |
| AGCCAGAACC | CGTCGCTAGC | GGGCGTCTCC | TCGCTACAGT | AGATAGAGGA | 350 |
| AGCGCAGACG | GTTAATNGTT | TCGGTAACC | GATTTAGCCA | TCGATTGAAG | 400 |
| ATCTACGGCG | CACGGATCGT | NGGATTTGAA | TNGCGTTTAC | AACATTTGA | 450 |
| GTTTAGAGTC | NTCAATTGGN | GGGATTTGGN | AAACTNCGAG | CTGGCGGNCN | 500 |
| NAGGGGAGAN | CGGCAATAAA | AACTTCCTCT | ACGANCGATA | GCTTNACAGN | 550 |
| TTNCTNGCGG | AAANAGGTTC | GACCANCNTC | ACACGGAGGG | AGCTTTTNNT | 600 |
| CCTTCCTCTN | NNAAAGCCTT | NAGNCCTCNA | TCNCCCNNTA | NNTCGTATTT | 650 |
| CCANCACGAT | ATCCGNNCC | CCTNNACTCT | CNCTAATCCN | CCCCTNNNC | 699 |
| SEQ ID NO. 25 | | | | | |

FIG. 1F

Plasmid: 20

```
GAGCTCACCA AACGTTGCGG AGACAGGTGG GCGCTCGGGA CTCACATCCA      50
CCGACTCATT GCGCTCTTGG ATCACGACAA CCATCGCGAA CTGTGCAATG     100
TGCTGGTCGG NCTGCTACAC CAAACACCCC ACATGTGGGC CCGTTCCATC     150
CGTCTTATCG GCCGATTAAG AAACTATCTA CAACAGAAGT TTCTCAATAT     200
CTTGGTGGAT AGCGGANTCC AGATCGATAG TCTTTGTGAG GGTTGTTACC     250
ACAGCGAAGC GTACCGNTTG NTGGTCCAGA TCGAAAAAAA CGAACTCCAC     300
GCCTAGNTCT CTAGCCTGTG CAAGNACCGN NTTCACCTGT CGGTGAAAAC     350
GAAANTGNAN GGGACACCTG TNCCGNCCGT NTTTTTAATN AAATAATAAA    400
ATTGGTTCTC ATNAATTTAN ACGGNCTTAA NTNTCCGNNT TNGGGAAGGN     450
AAANTTTTNN TTNTCCCCCC AAACATTCCC CCCCTTGGNC CNNNNTNNNA     500
NCTNNACTTN CNNNCGGCCN TNTCCTNANN AAANCNNATT TTTTCNNNTN     550
CCC       SEQ ID NO. 26                                    553
```

Plasmid: 21

```
GAGCTCGAAT GAGATCACGA TGATCCGTGG NGTTCACCAC GACAGGCCAT      50
TCCGAGTAAA CCATGGAATC CGATACCCCG TAGGCCGAGT CCAGAAACAC     100
CGAGGCGAAA CTGAACCCCA GCTCGCAGAT CACGGNGTCG CTGAGCATTA     150
AGTGGTCTTT TTCCAGANTG GTCAGCTTCT GGGTCGTGTA CCCGAAGTAC     200
TTCTTGTGCG GAGNCAGCTT GACGGACTGC TGGNTGTCGN TCACGAACTG     250
NTTCAGGGNC GNTTCGATCA AGCANCTTGG GTCTCTGAGT AAGGGNAGGG     300
GTTTGGCACC ACGAANGTTN TTNAACNATA ATAGAANAGG GTTTTCCGTT     350
CANCCCNAAG GNAAGGTCNA ATCCCCCGNN GATTCCANGA ANCGANNTTG     400
GGTTTTTCCA GAGAAAAGTT NANCCCNATT CCNAAATCGG CCTNNAAANA     450
ACAAAGAGGT GGGNNGGGTN AAANNNNNNA NGNNNACCNN TCGANTTCTC     500
CAANNNNNTT TGNNCCCCCC CNCCNNAGAA GGGTTNANTT NCCCNATTAT     550
TAATTTTNTT      SEQ ID NO. 27                              560
```

Plasmid: 22

```
NTNNTNNNNN NNNNNGTTTT NNAACTCTTA AGCTCTACTA CCCGCGGAGA      50
GACGNGTTCG CGACGGAAAA ATTCCGGTCC CCTTTGTGGA TCGCGATAGC    100
CTGTTGGCCA ACGTTATTCC CGTCGCCCCC ACTCCCAATC CGGAAACTGA     150
AGGANGACCG GAGAAGAAAG CACTGACACG ACAGTGTTCG CTCCCTACCC     200
CCCACCCTAA GAAGCTCGGA GTCCAGCCTG ATTCCNATAG CGACAGCGAT     250
ACGATTATCG ATTTAACTAT GGAAGGCGCG GGATCTCTGT AGATTTGTTT     300
TTTGNTGAAT TGTGCAACCC GCATTGCTTG GTGTCACTGT AGACACGCCT     350
TCTGTCAATC ACTAGTGTGC TTTTGGTAAT AAACGGNTNT GGTTGGTATT     400
AGCCACGCAG NNNGTGTGTC TCATCTTCTT GGCGGGTGAT GGAGNGCCTA     450
CCCGCCTGTG TNAAGGTTAA TGGGNTTCAC AGTTNGGGAG TGTGANTTTG     500
AGATTTGTT NAACCCNAAT TGTTTATTGG NTTAANTCAA GNGTCCTTTN     550
TTNTTGGNNT NTTNTANGNT CTTTNATTNT TNAATTCCNT TNTNTTTTTT     600
ACGGTNNGGC GGTTGGNNTC NTNANTTNNA ANNCCNNNGN AAAANTNANN     650
ANAAANNNNN NNNNTTNTNN ACTTTNNTTC ANCTGNANAA TTTA    SEQ    694
ID NO. 28
```

FIG. 1G

Plasmid: 23

```
TGTTNNNNTG TCCNTAAAAC CCTTGAAGCT CCGGGTNCCC CGGATTTTAT        50
TGACGAGATC GGAAGTTCTA GAAGNNTCCA CCACGCCCCC AATTTCCTGA       100
ACCACGCCCA TTTCGGATTG CAAATCGGAG AGCGGGGGCC GCTGGGTAGA       150
AAACGGGGGA TGGGGAACCC GCAATGCAAC CCTATGGGAG CAGGCCGTCG       200
AGNACCGTGG GGGGAGGGGC GGTNTANCNA ACCCTGCCAT GCACGCTGGT       250
GCGAGGTGGG GGTTGGCCAC TGNAAATGAN TCTGGGGTCT CCTGAATAGG       300
GGGATNNGGC TGNAGCCNCC AACCCNNANT NATTGGTGCA TCATGGNGGA       350
TTNGNNACAC AAACCACCTT TNTTTTTTTT TTNTTNATTG GANGTTTCTN       400
NCAACCANAT NCCTNAACTT CTTTNTTTGC CCCAGNTTNC TCNNGGNCCC       450
NNNTNTNTCC NCCNTCNTTC CTNNANTCCN TNACCTGNGT NTCTTNNNNT       500
TAAAANCCNN TATCCCCNTC NATCANNNGT GGANTNGGNG NNTNNNNCTT       550
NNGNTNNATN NNCTCNTCCC NNNNTTTNNT NTTTTCCTTN NANTNATNCN       600
NTNNNNNTTT NNTNTTTTTN TTTNNTNCCN CTTNNNNNCT CTNNCNTTTN       650
TCNANTTCAN ANCTTNTCNN NNNTNCNTTN TNNTCTTTNN TNNNTNNNNT       700
TTCT      SEQ ID NO. 29                                      704
```

Plasmid: 24

```
TTTTTTTTTG CNTTCTNAAA GCAACNACAC NCAAGGNAAC ANAAGATGGA        50
GNTCCAGCGG NGNATCGGCT CGCGCGACCN GTCGGAAGGT TCGGAAGCCN       100
GGCGGNGTTC AGGGAAACCG ANTCNTTGGA NNCCNANNTN AGNCNCANNN       150
NTTNTTNNAT NTANGNNGGA GACANNAGNN CNTCCCATNT NGNANCATAT       200
NNTTANNTNN NTCCANACNT ACCCCANNAA ANCGGTCNTT TTTTTTTTTT       250
TACANANNNT ACTTAATTTA AAAANCCTCA ATANNNAANC NANNTNNTCC       300
CANGNACCAN NNCGCNNTAT NNCNAANCTA TCNNTTNCCN NGNNNNGCTA       350
TNANCGACAT CATNCATNAA NTATNNAANC NAAANNCATN ATAGAGTTTT       400
NNTNANATTN CNANNNCTAC AGNNANTCAN TCNGNNNTTA ANCANAGNGG       450
NGGATATCTC CNCAANCANN NTANNAANTN GACNCCTANN TATANNTTNN       500
NNTNNTNTAA TNCANNCTAN CANATCNNNN CNCTCTACAT TTNTACNNNA       550
ANACANATAN NCAAANNNTN TNNATNTATN NNTCCNCCNA NNTNATNANT       600
AATTGTNANT ATNTACNAGT GCTNTNCANA ANGNTNANGC NATCNNACTC       650
NCTACTTNAC TTAATNNAAN CACNNNANTT NNTTCACTAT NTTNNCNATA       700
ANTATATATA NTCNNGNACN NNTANCN   SEQ ID NO. 30                727
```

Plasmid: 25

```
GAGCTCGGAC CTGGTCTTCG ATAGCAGGGA ACTCATTATC AGGAACATGA        50
GGGATCATTG ACAACACCTC ATCCTCCAAA ACGTCCCCAT GGCCGNCAC        100
CTCATCCACA GCAGTGGTAC CAGTCGCGTC CAAAATTGAG GTGCTTTGAT       150
CGCAATCCAT GTCCACCAAA CCCATAACTT TCTGAACTTC ACACAGNGCC       200
ACTTGGTCCG TAGAAAACTT ATTCAGCAAC ANCCTCCAGA GTGTCGTCCT       250
CAGACATGGT AATTTCGCCC ACCACCAGTT TTCAAGATCA TATNGTTCCA       300
GAGNCTNCAA TANTCCCGTT GCGCAATTCT GATTCCTCCA CCTCGGAGGT       350
GGGGNGCGCT ANTCGGCTGG CATTTATTCC TCAAAGAAGT NCNTGCAGNA       400
GNNGAAATTT NATCTTGCAC TNNCCNATCN AGGNGGGTTC AAGCTTGGAG       450
CAGNTTCTTC GNNANTTCNT TGTTCCTACC GAAATTTCTT AANAANCNTC       500
GNGCNCCNTC CCAACNTACT TATNTTATCN TCGCNGTNNA NC               542
SEQ ID NO. 31
```

*FIG. 1H*

Plasmid: 26

| | | | | | |
|---|---|---|---|---|---|
| GAGCTCTGCC | GGGGGTGTGG | AGGTGGACNG | TTTGACCGGC | TGCTCCGTGA | 50 |
| CTGATGGCCG | CAGCGGCGGC | CGACGGGTTA | GGATNTTGAC | GACCTAACAG | 100 |
| TTCAGTTATG | TGAGGAGGAT | GAGTGGTGAG | CGGTGAAATC | ATAGTNCACA | 150 |
| GGTACAGGCG | AGGGATATCG | CCGCAGCCGT | NTTCCAGAA | CTCGTCAGCA | 200 |
| TCGGTGGCCA | CGAGATGCAG | AGTTAGTCGA | GGAAAGTCGA | AAGATNNTT | 250 |
| TATTNTTNTN | GGGTCCCNNG | AGCGAAGGTA | CAGACCTNCA | TGGCGANCAG | 300 |
| ATAGTNGGNT | TNANNAGCCA | NNGCCAGAAG | TNGTTTCCGN | NNAATGNTAC | 350 |
| AAGGCACCTT | AACAAGACCC | GNCGCTTTTT | TNGGGNNAAA | GTNTGGCGNA | 400 |
| AGCNCAANNN | NCNNACCNAC | TNTCNNNGNA | TTTNAAANAC | NNNNGCTNTC | 450 |
| CNTCTNACTC | ANTCTNAACC | NATCCCNNCN | GGCTANNNNN | ACTNNNTCNT | 500 |
| CCCNNCCCTT | CTNTANACC | CNNTGGCNN | CCCTCCANAA | NNNCNTTCTC | 550 |
| NCTTAAANTN | CCG | SEQ ID NO. 32 | | | 563 |

Plasmid: 27

| | | | | | |
|---|---|---|---|---|---|
| NNTNTAGGGN | GTTTTNTNGN | NCGGGATNNN | NTAAGCCCNN | NTCTNTTTAG | 50 |
| GNATNNNGGC | CAGTCGTCAC | CNCNNTNCNN | GCNAAGNANT | AATGGGGGNG | 100 |
| NNGGGGGGGC | TANGGNATNT | NGAACNTCAN | NNGTGNACCN | CCANTCCNAG | 150 |
| TCAGCGANNG | CNAGTGANGA | GNCCACACAA | NANCGNNAGT | ANANCGACAT | 200 |
| CNATGNGTCT | ANCCTNACAN | GCNNCTTTTA | TCNNATCCAN | NNGTANATNN | 250 |
| NCAGAAGAGN | TNTCAANCAT | NTCGCTATA | NTNNCNGNAC | ATAATTCGAA | 300 |
| NNANNTCTCT | TCGNANNNNT | CGCTNNNNNG | GCNTNTGTN | GAACTATAGN | 350 |
| CNNCNANNTN | CCTCNCNNAA | CTNGCTNNAA | TNANTTTTTT | NNTTTTATTN | 400 |
| CNNNCTCCGA | CTCGANCNTC | CCCTNNGCNN | TTCNNNNNTN | NTNTNATTTT | 450 |
| NNNNCCACCC | NCTNGCCATN | TCCNACANCN | NCTCNTNNCN | NGCNCCNNNT | 500 |
| TTTNTCANAN | CNNNCTTNTN | NANAANTTCT | CTCCATTNTN | CNNCNCCCNT | 550 |
| TCNANTNTTC | CTATATCCNC | NNANANCAAT | AACTNNTTTN | TNANTTCACC | 600 |
| NTACTTTNNT | NGTATACTTA | AACNNTCCCA | CTCCNTCTCC | ANTTTTNTNA | 650 |
| ANTCCNNCNC | CCNAATCNNC | CACCCNNTNC | NTTTTTNNCT | TTTATA | 696 |
| SEQ ID NO. 33 | | | | | |

Plasmid: 28

| | | | | | |
|---|---|---|---|---|---|
| GTTTGCAACT | CTGAAGCTCA | TAATCCCTCC | AAATCGGTAG | CGTGGCAGTA | 50 |
| GTAACGATGT | CGCCTATGGT | AGCATTCAGA | AAGTAGACGT | CGCTGGCAAA | 100 |
| GGTANGTTTT | CGCCTTTTGA | TTAGGACCAG | TAATNTCAGT | ATGTTTGCTA | 150 |
| TGAGTCCGAC | GCATATGGNG | ATGCTATAGA | AACCGACGCT | GACATCGCGA | 200 |
| GATGCGTCGT | CGATCTTAAA | CACTTGCAGA | AGGTTACAGG | AGGAGTTGTT | 250 |
| CANGTTTGTA | AAAAGTCTGT | TCGCAAATCG | AACAATCTCG | ATTTGCAATG | 300 |
| TCGGGGTTNG | TGACCGGNCT | CAAACATATA | TCGGNTGGTN | GTGTCGTTGC | 350 |
| GCTATCAACG | CGCAATAATT | TAGAACGCGG | ATTCATATTC | CCTGGGCGGA | 400 |
| AGCTCTGGGG | GATCGTCCNT | TCANGCTATT | NGGGAGACAT | NAGCTTTTAC | 450 |
| AACGTTCCCC | AGCTTATGGN | ATGGTTGGGC | ACTCCCATTA | AACANTTCGG | 500 |
| AGGTACCCNC | CTATTGATNT | TACGACTTNA | CACATNTTCN | AACTTNATAG | 550 |
| GACTTAAGGA | CGGGTCTTTN | NNAACANAGA | NGGTTTTACC | CNCCCCCCCA | 600 |
| AAAAAGTTTG | GTCGTTTCCA | ANTTTTCCNA | ACTTTTCNGN | CGCGATCATC | 650 |
| NCCCNNCNC | TCGAAGNTTT | ACGTTGGCAG | CCCNNGAAAA | NATGTAAAGC | 700 |
| CCNTTATNCN | CCACTNCCCC | CTCCNCTTNN | NNCTNCCCNN | CT | 742 |
| SEQ ID NO. 34 | | | | | |

FIG. 1I

Plasmid: 29

```
NNGAGCTCTG CCGGGGGTGT GGAGGTGGAC NGTTTGACCG GCTGCTCCGT    50
GACTGATGGC CGCAGCGGCG GCCGACGGGT TAGGATNTTG ACGACCTAAC   100
AGTTCAGTTA TGTGAGGAGG ATGAGTGGTG AGCGGTGAAA TCATAGTNCA   150
CAGGTACAGG CGAGGGATAT CGCCGCAGCC GTNTTTCCAG AACTCGTCAG   200
CATCGGTGGC CACGAGATGC AGAGTTAGTC GAGGAAAGTC GAGAAGATNN   250
TTTATTNTTN TNGGGTCCCN NGAGCGAAGG TACAGACCTN CATGGCGANC   300
AGATAGTNGG NTTNANNAGC CANNGCCAGA AGTNGTTTCC GNNNAATGNT   350
ACAAGGCACC TTAACAAGAC CCGNCGCTTT TTTNGGGNNA AAGTNTGGCG   400
NAAGCNCAAN NNNCNNACCN ACTNTCNNNG NATTTNAAAN ACNNNNGCTN   450
TCCNTCTNAC TCANTCTNAA CCNATCCCNN CNGGCTANNN NNACTNNNTC   500
NTCCCNNCCC TTCTNTNANA CCCNNTGGCN NNCCCTCCAN AANNNCNTTC   550
TCNCTTAAAN TNCCGNNNTA TNNNNTGTCT TTATTCNCTT CAAGGCCCCC   600
CTCCCAGGTA GAGGTTTCGA TAAGCTTGAT ATCGAATGCC CNCAGCCCGG   650
GGGATCCACT AGTTCTAGAG CGGCCGCCAC CGNGGTGGAG CTCCGTTTTC   700
GCAGCGAGTG CGGCAGATGG TAGCGATTCA ACGTTCAGAT CTGGATGAAT   750
TCACGTACCC CTGTCAAGCT CTTAAAGGA AAGGGATCGC TGTACGTCAC    800
CAACCGTGAC TGATGCACCA AAGCTACCAG GACGCGTTCC GTAGGTCTTT   850
CTCGCGTCGA TTGACTTCGT CCGTTACGAG GCAGTGGAGA CGAGGGCCAG   900
GGTCTTCCTG ATGGGTCGCT GNCTCGNGCT CCGNTGCCTC GACACGAACG   950
AACTTGAGAC TCGANGGACA TAGGTCTTTN TNNGGANCCG TATTCGTAAG  1000
GGGNGGAAGG AACCAGNGTA TTGGNNATCT TAGNTTCTTC CCAGGCTTCC  1050
CCTGATACGG GTCCGGAAGG CGNTCTTTTT AAANAAGAGC CAGTCGGNGG  1100
NNTTTTCTTT AAAAAAGTTN TGGNGGGGNT CTTCCCNNNN NNNNGGGAGC  1150
AANNNNNTTC GNNGNGGGNN ANCCATTTNN NANNNCNNNC CNNNNNGGNN  1200
NTTTTAATNN NTTNCNACCN NNTNNNNNNN TAAGTNNGGC NCNNGGNTT   1249
SEQ ID NO. 35
```

Plasmid: 30

```
GAGCTCCGTT TTCGCAGCGA GTGCGGCAGA TGGTAGCGAT TCAACGTTCA    50
GATCTGGATG AATTCACGTA CCCCTGTCAA GCTCTTAAAA GGAAAGGGAT   100
CGCTGTACGT CACCAACCGT GACTGATGCA CCAAAGCTAC CAGGACGCGT   150
TCCGTAGGTC TTTCTCGCGT CGATTGACTT CGTCCGTTAC GAGGCAGTGG   200
AGACGAGGGC CAGGGTCTTC CTGATGGGTC GCTGNCTCGN GCTCCGNTGC   250
CTCGACACGA ACGAACTTGA GACTCGANGG ACATAGGTCT TTNTNNGGAN   300
CCGTATTCGT AAGGGGNGGA AGGAACCAGN GTATTGGNNA TCTTAGNTTC   350
TTCCCAGGCT TCCCCTGATA CGGGTCCGGA AGGCGNTCTT TTTAAANAAG   400
AGCCAGTCGG NGGNNTTTTC TTTAAAAAAG TTNTGGNGGG GNTCTTCCCN   450
NNNNNNNGGG AGCAANNNNN TTCGNNGNGG GNNANCCATT TNNNANNNCN   500
NNCCNNNNNG GNNNTTTTAA TNNNTTNCNA CCNNNTNNNN NNNTAAGTNN   550
GGCNCNNGGN TT       SEQ ID NO. 36                       562
```

Plasmid: 31

```
GAGCTCCGTT TTCGCAGCGA GTGCGGCANA TGGTAGCGAT TCAACGTTCA    50
GATCTGGATG AATNCACGTA CCCCTGTCAA GCTCTTAAAA GGAAAGGGAT   100
CGCTGTACGT CACCAACCGT GACTGATGCA CCAAAGCTAC CAGGACGCGT   150
TCCGTAGGTC TTTCTCGCGT CGATGGCTCG GTCGTTACGA GGCAGTGGAG   200
ACGAGGGCCA GTGTCTTCCT GATGGCTCGC TGNCTCGCGC TCCGCTGCCT   250
CGACANCGAC GGATCTGAGA CTCGAGGGAC ATAGGTCTTG TTGCAACCNT   300
ATCGTAACGG TGCAGCAACA GCGTATTGGG ATCTTAGCTT CTCCCAGGNT   350
CCCTGATACG GGTCGAAGGC GTCTGTTAAA CAGAGCCAGT CGGNGNGTTT   400
TCTTTAAAAA GTGCTGGCGG NGCTCTTCCC GNNCCGTAGG GAGCAAAAAA   450
GTTCNTGGGG GGGATCCCA NTGNNNATNC GTCCNGGTNN GGGAATNTNA    500
NTNNTNTTCC ATCCGATTTN TTCTTANGNT CCGGCTCGAG GGCCGNACCA   550
AATANTNANA GCCCCAAAA ATTTNNTTTT TNGCCCNCCC ATTTGCATTG    600
NNCCCNTNGN TTNCGGCCAC CC       SEQ ID NO. 37             622
```

FIG. 1J

Plasmid: 32

```
ACCNNNTCNN NANNATTTTT NNNNAGNCNC TTNANNTNCT AAAGCNCATN    50
TANNCCTNAA AAAAATTTAC CGNGNGGNTC TCACTCAGGC CCCNGCCAAA   100
NAGGNTTTGG TGTTTGCGCG GCCGGTCGAG CCCGATGTGG CGGTGCCGGA   150
TNACGTNTCG GTGTGGTGAC GGTGCGGCCG GAGAGGGGGA GGAGNAGACA   200
GACNGNGANC AGNGCGGTCG NGGNCGGACN GAGCCGAGNC GTCTTNTTTT   250
NGGAGCNGCT GTATNTCATG NCCCGACANN NCCGNNGGGA NGNCTTCGGA   300
GCTACGGGTC ANTTCNNCCA CNACNTCATT CNGTNGNCCT NNNANTCNGT   350
NTGGGANATT TATCCCCNGG NTTAANNNAC TNNGNCCCTT TTTTTTTTTT   400
TTTTTTTTTT TTTGCNNNGG CCCCGCACNA NNNCACNCGN AGTTGNTNAG   450
CCCNNNNCCC CANCNNCTCC CTTNNTATNC CTAACNCTCC CGGATGGCCC   500
NTTTTNTTNT CTCNCGCCGC CTCTNTGCTN CTTCTCACAT TANCATAACN   550
TCTACTTTNN TAGCTTNGTC TCCTTTNCNN NTTTTCTNTC TNATAAANNN   600
NCNNNNCNTT CNNNCTNTTN NCNTTACNTT NNCCNTGCTA TCCNCCCNTN   650
NCCNNACCCN TNNCAGTGGN NNCNTCTCCN NNACTTCTTN NNCNATANTN   700
SEQ ID NO. 38
```

Plasmid: 33

```
NNTNTAGGGN GTTTTNTNGN NCGGGATNNN NTAAGCCCNN NTCTNTTTAG    50
GNATNNNGGC CAGTCGTCAC CNCNNTNCNN GCNAAGNANT AATGGGGGNG   100
NNGGGGGGGC TANGGNATNT NGAACNTCAN NNGTGNACCN CCANTCCNAG   150
TCAGCGANNG CNAGTGANGA GNCCACACAA NANCGNNAGT ANANCGACAT   200
CNATGNGTCT ANCCTNACAN GCNNCTTTTA TCNNATCCAN NNGTANATNN   250
NCAGAAGAGN TNTCAANCAT NTNCGCTATA NTNNCNGNAC ATAATTCGAA   300
NNANNTCTCT TCGNANNNNT CGCTNNNNNG GCNTNTNGTN GAACTATAGN   350
CNNCNANNTN CCTCNCNNAA CTNGCTNNAA TNANTTTTTT NNTTTTATTN   400
CNNNCTCCGA CTCGANCNTC CCCTNNGCNN TTCNNNNNTN NTNTNATTTT   450
NNNNCCACCC NCTNGCCATN TCCNACANCN NCTCNTNNCN NGCNCCNNNT   500
TTTNTCANAN CNNNCTTNTN NANAANTTCT CTCCATTNTN CNNCNCCCNT   550
TCNANTNTTC CTATATCCNC NNANANCAAT AACTNNTTTN TNANTTCACC   600
NTACTTTNNT NGTATACTTA AACNNTCCCA CTCCNTCTCC ANTTTTNTNA   650
ANTCCNNCNC CCNAATCNNC CACCCNNTNC NTTTTTNNCT TTTATA SEQ   696
ID NO. 39
```

Plasmid: 34

```
GGTTTNGNAA CTCTTGAAGC TCTCGNTCCC CTAGAAACAA GGCTCAGTAC    50
GTGGAAGGGG TGTGGCNTCA CGCCTACACA CCTGGGCTGC TCGACCATCA   100
TAACGTGTGT GATCTGGAGG GGNTTCTTTA CCTGTTGTGC TGCGGACCCC   150
GNAGTTTCTG CTCGCGGNAC ACGTGTTTCG GGCGGGAGAA GCACGGTTGA   200
CCATTCCCCG CCCTGCTCCC CAAGGATCTT TTACGAGCCC GNTCGCGATT   250
ATATGACGNA TGTGAACCTG GCTGAACTTC TACGTTTATG TGTGGNATCG   300
CGGCTATGAT CGCCCTTCGA CTTCGGATCC NACGCCAGGG GNTGATGACG   350
ACCGANCTNC NGNCNGNCTT TTAATAGANC CGCCCTCNCN TNCNCACCNN   400
TCTCAACAGG ANNTTGCTTA AAAGNCGTGA TCCNANCGNC NGCTTCTTNG   450
GCCGTCNCNA TANTTCNCTC TTCNACNTNC CTNNCTTNNT CCTNACANTC   500
TNNCTTCNTC CNTCNNGCCT CNNTGCACNN CNTATTTCTT CTNCATCTNT   550
TTANCCTCCC NTCNNANTTT NNNTTNNCNA TCACTCCANN CACNNCCNNN   600
TNTTANCCCC CANNTCCCCC CCCATTNTTN NCANCTNCTC CNCTGCCAAN   650
NNCCTNNTTT TTANCCCCNT CTNNCCATNT TTTNCTTNGC TTCNCNTANA   700
TCCANANTCC CCCTNNACCT TACANCTCTN TATCCTCTNA TCCCTCCNAC   750
TATACCCCTT NTTNTATCNT NTCCNCCCC   SEQ ID NO. 40         779
```

FIG. 1K

Plasmid: 35

```
GAGCTCGTCT TGCAGCAGAT TGCGGGTGGA ATACACGTNT TCGCTCACAT      50
CGCACAGCTG CGTCTTTTGA CTGCTGACGG GTTTGACAAC AGAACCCAGG     100
GGTGAGAAGC AANAACGACG CGAGCAGCGA AACCAAAAAG AGCCCTGCCT     150
AATGAATCCC CGCAAAGTCT CGGCGAGTTT GAGCATCACG GTCCCGTNAA     200
TTAAAACGTG TACGCAACCG NNTGATNTCC ATGAACACGG CCCTGTTAAC     250
AAGGCTCCAA CCAGCCAATC ACCGNGTACT TGGNCTTNCT CCAAAAATGC     300
CAATAACGAG GNNGGGNTAG CCTCGNNNGG GNCTCTTNCA ACGGTNCGAG     350
GGATCCCGNN AGTTGAAANN TGNATNANGG GCCNTTCCCC CCCAGGNNNA     400
ACCTTGGNCC CCANNNTTTN GNTNNANANN AANNGGACCN NCGNCTGGGT     450
ACCCCNNCAA GANCTTTNAA ANTTNCCCNC CCANNTGGAA AAANTGTNNT     500
TNTNCCAANN NTTTTCAAAA NTTCNNCCAA ANCGNNNNNC CNNTTNNTTG     550
CAANNAAA       SEQ ID NO. 41                               558
```

Plasmid: 36

```
TTTTGANACT TNTTAAGCTC GATGACACCN TGANCTGATN GCGACAAACC      50
AGGAGCGGCT ACANCCACCG AAGACGATTT ACGCGCGCGC GATGCACAAG     100
CTCTTGGGCT ACCGCCCAAC GCCGGCTGCA ATGCCCCTCT GAGCGACCTG     150
GNTCAGCTGA GTCGTGCTCT ACGTTGCGAT TGGCGATACT GGCGACTCAC     200
TACTGNCCCG GAAGAATNNG NTGATCCCGG CGAAGACGAT TCTTATAACG     250
AGTTACCATA CCGTACGTGG GCCCCACCG ACTATANNCC TCAGNGGGAN      300
CCACAGACCG CATTCGGGGC AANCACAACC NTCGCTCGTC GNTTGTCTCA     350
TCACCGAGCC ANTGCCNTTT TGTTCCCTAC GGCGTCCCTT GGCCCTTNNA     400
GNCCNTCGAT CNNNGTTGNN NGNCANTTTT TCCCNTCTCN AGTACCCNNN     450
GGNGGTGNTT NGNCNNTTCC TNTNNNACGA TTTTNNNAGT NNNNCCANAT     500
TCTTCAGNNT CCCTCTCANT CNCNTCTNNG NANTNTCNCC CCNANTCTGT     550
TTTTTCTTTN GTNNATTTNT TNNTNAATTT TCTTTCTNNN TCCCCCTNAN     600
NACCNTNNNC NTTNTTCTNT TCTTCTNCNC NNNTCTCCNN CNNTNTTNNT    650
CNTNTTNNTN NTNTNCNNTT      SEQ ID NO. 42                   670
```

Plasmid: 37

```
GAGCTCTCCG AAAGCTGGAT GNACGNGAGT CTGGTGAACT GGATCTACAG      50
GTTTCGCTGC ATCGTTTCAA TTTACAGAAA TATTCTCTTC GAACTCGCCG     100
GCACCTTCAG CACTTGNGTG CTTCTCTGGT TTAGTTTCCC AACAGTTGAA     150
ATGTGTCTGC TGTGCACTGT CCCGACGGGA GCCATATTAA TTCCCACCCT     200
GTGCCTCGGA ATAGCCTGTT GNTGTCAGAA AGAGATGNTG CGATACTCGG     250
GATCCTCTAC GCTCGNTTGT GTNTTAATTG ACACTTCAAT AACAAGTTAT     300
GACCGGTTTC TTGTNGTCCN GGGNAAAAAC CTCAACCTCG GGAATNGGCT     350
TGAGGTNGGG TGATGATCCN NTATTTTTNA CNCCCTNGGA ATTTANGCCN     400
NCCNNAAGAA AGGCCCTTGN NAATTTTCCC NTCCNAAGG GGGGGCCCN       450
NCCCCTTTTT NTTNCTTTNN CCNGGNTNGG GCAAAGGGGC CANCANTTAA     500
AATTTTCCAC CNNNTTTCTC CTTCCTANAA GGGGGTTNAA TTNTT    SEQ   545
ID NO. 43
```

FIG. 1L

Plasmid: 38

| | | | | | |
|---|---|---|---|---|---|
| NCNNTTTTNN | NTGTTCTTCT | ACTCTGAAGC | TCGAGATCNC | ACCGATGCAT | 50 |
| TNGNCGTGAT | GGAGATCCAG | GCACACCGTA | TCNATGTTCA | CGGTAAAAAG | 100 |
| CAGNCCCATG | AACTCGTNCT | GAATGTTCTT | GGACGATTTC | CAGACGTGAC | 150 |
| TGTCCGTTCA | AGTAATTGTC | CGGCAGGGTT | CCCTTGAACT | GCGCGGTATA | 200 |
| GCGAGTCATC | TTCTTGTGAC | CGTGACAAGT | GACTCTNTTG | NTTGTCCACG | 250 |
| TAAGCTGTTC | CGCGTGGACG | ATTAAGTGGT | CGTCCTGACG | GGTGAGGGTG | 300 |
| GNCTTGTCAA | ACGGCACTTC | TTCGATCCAA | CAGTAGNNAA | NGTNGNCGGT | 350 |
| CAGGGTTAGG | AAAGGCAACT | CCNTGTNTTN | TNTTTATNNC | CNNNCNGCTA | 400 |
| ACGATNANGN | NTNAACCCTT | ATCTNTTTTG | CNCCANNNNN | CCCCCNTCTT | 450 |
| CTNCNCNNNT | NANANNNNNC | CNCGGNCNTC | TTCNTCCNGG | NGNCCCCNCA | 500 |
| NCNTNNCCCN | CNCTANNCNN | GCCNCCTTCN | NCNANTNNCT | TCTCTNCTNC | 550 |
| TTNCCCCCCA | NCTCCCTTTT | CTCTCNANNC | CNCNCNCCNC | NCTNTNCCTC | 600 |
| NTANNNCTTC | NCNNNNTCAC | CNCTNTCNCC | NNCTTTNCCN | ANCCCCCCCT | 650 |
| CCTTTCCCCC | TNCNTCCTTA | TCTTNTNTTT | TCANNTCN | SEQ ID | 688 |
| NO. 44 | | | | | |

Plasmid: 39

| | | | | | |
|---|---|---|---|---|---|
| TTTTGANACT | TNTTAAGCTC | GATGACACCN | TGANCTGATN | GCGACAAACC | 50 |
| AGGAGCGGCT | ACANCCACCG | AAGACGATTT | ACGCGCGCGC | GATGCACAAG | 100 |
| CTCTTGGGCT | ACCGCCCAAC | GCCGGCTGCA | ATGCCCCTCT | GAGCGACCTG | 150 |
| GNTCAGCTGA | GTCGTGCTCT | ACGTTGCGAT | TGGCGATACT | GGCGACTCAC | 200 |
| TACTGNCCCG | GAAGAATNNG | NTGATCCCGG | CGAAGACGAT | TCTTATAACG | 250 |
| AGTTACCATA | CCGTACGTGG | GCCCCACCG | ACTATANNCC | TCAGNGGGAN | 300 |
| CCACAGACCG | CATTCGGGGC | AANCACAACC | NTCGCTCGTC | GNTTGTCTCA | 350 |
| TCACCGAGCC | ANTGCCNTTT | TGTTCCCTAC | GGCGTCCCTT | GGCCCTTNNA | 400 |
| GNCCNTCGAT | CNNNGTTGNN | NGNCANTTTT | TCCCNTCTCN | AGTACCCNNN | 450 |
| GGNGGTGNTT | NGNCNNTTCC | TNTNNNACGA | TTTTNNNAGT | NNNNCCANAT | 500 |
| TCTTCAGNNT | CCCTCTCANT | CNCNTCTNNG | NANTNTCNCC | CCNANTCTGT | 550 |
| TTTTTCTTTN | GTNNATTTNT | TNNTNAATTT | TCTTTCTNNN | TCCCCCTNAN | 600 |
| NACCNTNNNC | NTTNTTCTNT | TCTTCTNCNC | NNNTCTCCNN | CNNTNTTNNT | 650 |
| CNTNTTNNTN | NTNTNCNNTT | SEQ ID NO. 45 | | | 670 |

Plasmid: 40

| | | | | | |
|---|---|---|---|---|---|
| CNNNNTGTNN | NNNGTCCTTA | ACNCTTAAGC | TCCTTGACCC | CAGNNACGGT | 50 |
| GTCCACGGGC | AGCAGGAATT | TGTCACNGCA | AAGGTATTTC | TTCTCCAAAT | 100 |
| CTCTAATATT | GAGATGGCCA | AAAGCTCCCG | CGCGAAGAAA | ATCAGAAAAG | 150 |
| GTAAAATACC | ATCCAGGAGG | CCAAGCGATA | GGAAAAGTTT | CCCCGTTCAC | 200 |
| CTTCCGAACA | AACTTCATCA | GACGCTTAGG | CGCGTCCTTG | GTGCTCACGG | 250 |
| AGCAGTTAAA | AAATTCACGG | ACAAGCAATT | CGTGACGCTT | CATGTCGGAA | 300 |
| ACAATCATGA | TGGACGGGGT | TACCAGTGTG | GAACGAAGTC | GGGCACGCCC | 350 |
| GGGCTCGCAG | GAAATAGATA | TAGCTCGTGC | CAACCCACAA | AAATCTGCAT | 400 |
| CTGCGTCAAT | ATTTTTAGG | GTACAACTTT | CTTGCTTTTT | NGGGTTGCTA | 450 |
| GGGTNCGGAA | TTCCGNAATT | GGANAGATNC | GTCGNTTTGT | CCGNNCTTCT | 500 |
| TCCTNGGGNN | NNCGNTAAAG | GTANTNAGAN | TTTTNTNTCC | CGGGGNNTNG | 550 |
| GGAACCCCCC | TGGGNTTTTT | AANNTATTGG | NCNNACTTTG | TGTTNANCCN | 600 |
| NCCTTNNCNG | GNNNNNNGGG | GNCGTTTCCN | NNGGNTNTNN | CGNNNGGCAT | 650 |
| CCNTNGNNTT | GGNNCCCNNG | NTNNGGGGGN | NTTCNTTN | SEQ ID NO. | 688 |
| 46 | | | | | |

FIG. 1M

Plasmid: 41

| | | | | |
|---|---|---|---|---|
| GAGCTCTAAA | GTATAANTAA | CTTTTNAGGA | CCCTGACCCT | GTTCAAATGG | 50
| AGCCAACAGG | ATGACACATA | AAGTTATTCC | ACTGATGGGA | AATTTAGTCT | 100
| ATTAGAGCAG | TGGTTCTCAG | ACTTCTACAT | TTCATGANCA | GAACAACAAC | 150
| AATAATAAAT | GGAGAACTTA | CATGGGATTA | ACAATTTTAC | CACCTACCTT | 200
| TTGGTCAGCT | CACTGAAAAA | AAAAGAAACT | GAACAGCAAG | GAAAGAACAG | 250
| NTTACTGCCA | CAACTGCCTT | TCTTGTATTC | CATTTNGNTA | CAGACTGGTT | 300
| AANAAAAAAA | AAAAAANGTC | ACANNTTGGG | NAACANTCCA | CAGACCCATT | 350
| NTTGGGGAAA | AAATGGGTTA | GAGAGTTTTT | TANGGGCCCT | NCTTATTTTT | 400
| NAAANTNGGA | CGNCTTTAAN | TCATNTTTTG | GGGGNCNTNA | CNATGCCNNC | 450
| CTTAANTTTN | NGNTTACATC | TTGNANGNTT | CTCAANGCCA | ANAATNTTTN | 500
| ANTNCCCTNC | NATTNAANCA | ATTNTGCCCA | ATTCCCCTNT | TT  SEQ ID | 542

NO. 47

Plasmid: 42

| | | | | |
|---|---|---|---|---|
| TNGGNAACTC | TCAAGCTCCC | CACCCCATTG | ANAAATATAT | TAACATCACG | 50
| TCATCTACTA | ANCCCCATTC | AAGTTGTGGT | CTATGGATCA | ATATCGGCAT | 100
| CACTGGGGAG | CTTGTAGGAA | ATGCAGACTT | TCAAGNTCGA | TCCCAGATCT | 150
| GCTGCTGAAT | CAGAAGCCGC | ACTTTCACAA | CATCCTAAGT | GATTCGTTTG | 200
| NACACTGCAG | TTTAAGAAGC | ACCCCACATT | TTGTTGGATA | TTCAAAANAA | 250
| TGAGAACCTG | ACTTTAGGGT | CTCCTCTCTC | CCACCCTACC | ACTACCTCCA | 300
| GCAGTCTCCT | TGTCTTCCAG | ATTCCACCTT | AAAATTCAGG | AATCACCATG | 350
| CACTGAGGAC | AGGCCTGCAC | AAACATCTAG | TTCCCCATGC | TTTAGGAAAA | 400
| GTGACAAAAA | CCCACAACCG | CCTTCCCTTT | CCAGGGTCC | CTCCTGCCCC | 450
| CAGGAAAAAT | AGGAANTTCC | CTCAAATCTT | CCCCCAANGG | CCGGGTGNAG | 500
| GNGGGTCAAA | ACCTGGTAAT | CCCAGGACTT | NGGGAGGGTT | TGANGCAGGA | 550
| GGGGTCAACC | NNAGGNCAGG | GNGTCNAAGN | CCAGGCCCGG | CCGAATGGGN | 600
| NAAACCCCNC | CTTTCNAANN | GTCAANANTT | GTGGNGGGGN | NNNNNGNCCN | 650
| NNNGNCCCNN | TTTTCGGGNG | GTTGTT | SEQ ID NO. 48 | | 676

Plasmid: 43

| | | | | |
|---|---|---|---|---|
| NGNCTTANAA | TTNNNNNATA | GCCTTAAAGC | NTNCTAAACT | AGTTTGGNAA | 50
| NTCATTATCA | GGGAACNTNC | CGNTTCANNG | ACAACACCTC | ATCCTCCANA | 100
| ACGTCCCCAT | GGGNCGTCAC | CTCATCCACA | GNAGTGGCAC | CAGNCGCGTC | 150
| CAAAATGGAG | GTGGTTTGNT | CGGAATCCAN | GTCCACCAAG | CCGATAACTT | 200
| NCTGAACTTC | ACACAGNGNC | ACTTGNTNCN | NNGAAAACTT | ATTCAGCAAC | 250
| ACCTCCAGAG | TGTCGTCCNC | AGACATGGNA | NACTCGNCCA | CCACCAGTTT | 300
| CAAGATCATN | NCGTCCAGAG | CCTGNATAAT | CCGCTGCGAC | TTCTGATTCT | 350
| CCACCTCGGC | GGCGGGGTGN | NTTTGTGGTT | GGNANTTATC | CGANANGAAG | 400
| TCCTGCNAGC | AGGACGACAT | CTTCATCTTG | GNANCTGCCG | NTTNNAGNGG | 450
| GATCAGNTTG | GAGCAGGNTG | CTTTCGNTCA | CTTCCTGGAT | CCCTTCGCNA | 500
| TNNGTNTTAN | TTTTCCTNCG | GCTGTTGATC | NCTTNNGTTC | TGAAGTTTTT | 550
| CCTCGCAGGA | AGCAGTGAAT | CTTNTNGAAT | CNTNCATTTT | CTNNGCTAGG | 600
| NNTGTANCAA | GGANATTNCN | CNATTTCTTC | GATTCTCNTC | NTNCNNAATN | 650
| TNNNATNTTC | ATANTAGNNT | CNGNCAAGGN | TNNTTCNCCN | TCGTAANG | 698

SEQ ID NO. 49

*FIG. 1N*

Plasmid: 44

| | | | | | |
|---|---|---|---|---|---|
| GAGCTCCAGA | GGAGATNGGC | TCGCGGGNGC | GGTCGGGAGG | NTCGGAAGCC | 50 |
| TGGGGGNGAC | CAGGGAANCN | ANGCCGTGNA | NCCCGCNATA | GGNCGCGGAC | 100 |
| TGGTTTTTTT | TTTNNTTNAT | GNGGTGCNCG | GACNCAGGGN | CCNGTTCGGN | 150 |
| TCGCAGACTC | NAATAGNNCN | CNATTCANCC | TNGCCTNANN | ATTCANGTAA | 200 |
| ACCCCACNNN | TTTNTAANAA | ANNGCCTANG | TCCCNNCTGN | TAANACGCCC | 250 |
| CCCCGCCTTT | TNTTTTTTTN | TTTTTTTTTT | TTTAATNCCC | NACNCNNAAC | 300 |
| NGAAANCTCN | AAANTTTCNT | TNCAAANTNA | TNANNCTNTT | NNANATANTT | 350 |
| NTNTCTNACT | ANNTACTCNN | NCNAANAATA | ATTNTAAAAT | AANCNATATA | 400 |
| NTNANAATAA | AATTATATAA | NNATNTCCNC | CTAAATTTCC | NTCTTTATAT | 450 |
| ACACTCCANA | TNAANTNAAN | NTTTATCTTT | CTATTATNTN | ACTACANCAA | 500 |
| NATNNTCATA | ATAATATTCA | ACTNCTNATC | ATTNTACATN | CTCTATATCA | 550 |
| TNACNNANA | CAANTCNTAT | TATANNCNNA | NTACAATACA | TTNTTTTNTA | 600 |
| TAAAATATTT | SEQ ID NO. 50 | | | | 610 |

Plasmid: 45

| | | | | | |
|---|---|---|---|---|---|
| GAGCTCGTCC | CTTGCGTACA | AGACAGCTGG | TTCGTGATGT | TCGCAATAAT | 50 |
| GACGGAGCTG | AGCCGTGAAC | ACCAGCTGAT | TGAACAGAGT | GCAGACGTGC | 100 |
| GAGATGGTGG | TTTGGATCTG | CCCGCCGGCT | AGCGGCGGGT | CTTGAGTGTG | 150 |
| CGGTTGCAGT | CGACACTTTA | TATTTTNTGT | AACGTTCACG | ATCTCTGATG | 200 |
| AATCAACTCG | CGTTCGAGTT | CGTTTTAACT | GTATGATGCC | TTGGATGGAA | 250 |
| CTTTCGATAG | TCCCGGTCGT | TATAAAATAT | AAATAAATTA | CTGTTGGGGC | 300 |
| GAGTGCAGCC | GAAAGTGGNA | GGCAGGTTGC | GAATAAGCAG | TTTCTTCTTA | 350 |
| CCTTCCGCGC | GAATCGGACT | CCGGTAAGCT | TTAGAAAGGT | TATTGGACGN | 400 |
| NNGGTTTGNN | GTCCCCGNGC | TCTCTTTACG | GTTCCGCATG | GAGAATCGNG | 450 |
| NNNCGGTATA | TATTTTCANA | GGCATGGGAN | GCGGTNTCNN | CNNGGAAAAG | 500 |
| GCTAACGGGG | GNTCCANNGG | GTTGCCNNCG | GTTCNATANC | CNNNCCCCAC | 550 |
| CACGTGGCCN | ATCCAAANNA | CAATNCTNAA | ANCACT | SEQ ID NO. 51 | 586 |

Plasmid: 46

| | | | | | |
|---|---|---|---|---|---|
| TNATTTGAAG | TCNNNNNATA | CNCTANAGCN | TTNNAAACTA | CATNATCGAT | 50 |
| ATTGAGGCCG | ATATTNCCCT | TCTNGGAAAG | AGCTGNGAGC | GCTTNCACTT | 100 |
| TTGGCAGANG | CTCGTCCATG | ACGCGCNCGC | TCTGCGCGGG | AGCATAACGC | 150 |
| GGGTGCAGTG | CCGAAAGCTT | GATTGAAATA | CCCGGGNCAT | CATAGATGCC | 200 |
| GCGACCGGCC | GACGCGCGAT | CANTCGNGTN | GATCGGANCC | TCATAATCCT | 250 |
| TGTAATAGCG | TTCTGCATCA | GNCGNCGNGG | TNGGCTGGGT | TCACCCAGCA | 300 |
| TATCATAGGA | GTGGCGGAAG | NCGNGTTCTT | CAAGCGACTT | TGNACGNTTG | 350 |
| GANTGCTNCA | TCANTGGTTT | NNNTNATTTT | AAGAGACTGN | TCGGCCGTCA | 400 |
| GGNGCATNGC | CAATATCCAC | GNCACGANGG | GTAACCCCNN | TTCAANCNCA | 450 |
| AGGGAGCAAT | NGAAGGCGCN | TNCANTTNCT | TCCGNACAGG | GCNNNTCNNC | 500 |
| ATTAANGNNN | NTTCCNNCAA | NTTGACNNNT | GNNCAAAAAN | GNCCCANCCC | 550 |
| NNTNGAATCA | GGNCAAANNA | AACGGNCACG | GGGGAANTTN | TAANTNCCNN | 600 |
| TNNCCCTCCC | NNNTNTTTTC | ATNTCNAAAG | CATNCNAANN | NNNNNTCCTT | 650 |
| TCCNNCTGGN | NNCCCCNATC | ATG | SEQ ID NO. 52 | | 673 |

FIG. 10

Plasmid: 47

```
GTTTTGCACA CTCNTGAAGC TCCCACTGCC ATCGAGTGGN GGATAACAAA        50
CTAACAGCCA GANACATGCC ACGATCATTT GTATTTTATT TATTGTTGGA       100
AAATCANCAA CAGTGTACTC TGCAGTTCAA TCGTAACCCC TGCTTATTTT       150
TCAGCGGTGA CGGTCTGAAC AGTCCGCTTC TACACGAGCC CAACCCCTTT       200
CACCTAACAG TCCACGCTCC CTACGACATT AACTTCGGTC ACCACTCCAG       250
NCAGACGGTG GAGATAGACA TCCGCTACGT ACAGACTGGC GGCCGCTGCT       300
TTTTGGTCGN CAACCTGCCA CACGAAGACT CGTTCTACAC CGGGATGTGT       350
CTGTGGCGAA CAGAGGCACT GAAGATCACC CTCTGGTCCC GGNTGCGCAC       400
TACCATTATC CCTCAGGGNA TCCCTATCGC CGCGTTGGTA TCAAATCAAC       450
GACATCGACG GCAATCTTNA CGCGTATAAC CATAACACGG TTTTCCCGNA       500
NAGTTCATCA TNNCCGACAG GAACANCCTT CTTCCCTTAG GGATTTTAAG       550
CTCCCCACCA ATAGTTTCCC TAACCTCATC CTANGGGCAA TTATTCCNCA       600
TCTNAGGGGN ATCTTCCTTA ATTTNTCTTT ATGGATAATG GTAGNCGGGG       650
GNCCNTCCGT CTTCTAGTGG GGNTGANCCC CAANTNGGCG GGGTANCATN       700
CNGTTTTNGG TTGACCTGGT    SEQ ID NO. 53                       720
```

Plasmid: 48

```
CTGNCACCCG TNAAGCTCAN TTACCACTTC TTGGGAGGAG GAAATAGATT        50
TTATCTATCT NTGGAGCAAT ATTTAAAGTT TAGAATTCTT TTGTTTTCAT       100
ATATCATTTG CATCAACTAA TGGAGAGTTA AAATGAGAAC CCCTACTACC       150
TGCCAACATC ACTGCTCTGT GGTGACTATG AAACGAGTAA GAGAAACCAT       200
AGATGCATTT TGACCTTGTG TCTGCCTTGC ACTGCTCCTG TATCCAGCTC       250
TACTTGGAGT TTAATATTGA CTCTTAAGAG GACAAATTAN TTANTGTAAT       300
AGTACATNGA AAATGTAAAA CACACANCAC CACNCANNNG CCTNCTCAGC       350
ATTGGCCTCA TTCCCATTTT TCCTCTGTGA CCCTGTGATA GACATTAGAG       400
GTTTCTGCCT TTCAGAAGCT TCTNCCCTCC CNCNCTCGGA GATGGAGTCT       450
CACTTTGNTT GNCCAGNCTG GAGTGCAGTG GTGTGATCTC GGNTCACTGN       500
AACCACCGNC TCCCAGGTCA AGCAATTCTC CCTGTCTTAG CCTCCCGAGT       550
NNTGGGATAC AGGCANACGC CACACGCCCA GGTAATTGG GTTTTANGNN       600
GAGNTGGANT CCACCAATTG GCAGCTGGTC TT    SEQ ID NO. 54         632
```

Plasmid: 49

```
GAGCTCCCGA CCTCAGTTGA TCCATCCGNC TCTCAGTCTC CCAAAGTGTT        50
GGGATTACAG GCGTGAGCCA CTGTACCCGG CCAAGAAGTG TTTATAAAAT       100
TGTTGAAAAA TCTGCTGTTT GTGGGAGCTT NTACTCAGGC ATTCTAAACT       150
GCTTACCGGT GTCTTTTTGG CCAGTATCGT GGATTGCCTA CTTGAACAAG       200
ACTNGTAGGG GAAGCAGATG GTCTTGTCAC TGGCCATGAG CTGCTTACCA       250
TATATTGAGG AGCCACATTC ANCTAACTGN TTTCCGAGCG ATCATGGAAG       300
TTTCTATTAG CAGCCTGCAG TACATCAGAG AAATGATAGC TTTNCTTTTN       350
TTNTCNTCAA CTTNACGTN CTGGGATACA CGTCTTGAAC ATGNAGGTTT       400
GGTACANAGG TTTTCATATG CATGGAAGTT TGTTNGNTGG CCCTATCAAC       450
CACCATTTNG GTTTAAGCCN NCATCNTAGG AGGTGCCCAA TNCCTCCCCC       500
CTTTCCCCCT ACCCCAA    SEQ ID NO. 55                          517
```

FIG. 1P

Plasmid: 50

```
ANNTTTNNNN TTTCNTGAAC TTNTANAGCT CATGNTCCCC NNAANTGTGG      50
AAGGGGGTGG GCACAGANAG CCTGACCTCC TGNGATGTGT GGGTGGNGGT     100
GACCACGGAA GGCTGAGGTC CACCGNGGTG GCGGTCACTC TANGAACTAG     150
TGGATCCCCC GGCCTGNAGG AATTCGATAT CAANCTTATC GATACCGTCG     200
ACCTCGAGGG GGGGNCCGGT ACCCATTTCG TCNTATAGTG AGTCGTATTA     250
CGTGCGCTCA CTGGGCGGCG GTTTACAACG TCGNGACTGG GAAAACCCTG     300
GNGTNACCCA NCTTAATCGA CTTGNAGNAC ATCCCCCTTT CGCCAGCTGG     350
CGTAATAGCG AAGAGGCCCG CACCNATCGN CCTTCCCAAC AGTTGNGCAG     400
CCTGAATNGC GAATGGGAAA TTGTAAGNGT TCANTATTTN NGTTNAAAAT     450
TNCGNNTTCA ANNTTTNNGN TTAANTCAAC NTCATTTCTT TNACCAATAG     500
GCCCNAAATC GGNAAAATCC CTTATTAAAT TCAACNCAAT AGNCCCANAT     550
AGNNTTNGAN TTTTGGTACG ANTCTGGGNA NAANANTTCC CCNATTCAAN     600
TACCTTCGCN TCCAATNCCA AACGGTCTAA AACCCNNTTC AGNNCNNATC     650
NCNCNTNNNN TNAACCATCA CNCTNTCAAT NTTNA    SEQ ID NO. 56   685
```

Plasmid: 51

```
GAGCTCAGGC TCCGGAGGTC ACCCCNATGC ACACATCCCA GGAGTTCAGG      50
CTTCTNTGGA CACCCCCTTC NACACATCCC AGGAGAAGGA GCTCCAGCTT    100
CTGTTCCCTT NAGTGAGGGT TAATTGCGCG CTTGGCGTAA TCATGGTCAT    150
AGCTGTTTCC TGTGTGAAAT TGTTATCCGC TCACAATTCC ACACAACATA    200
CGAGCCGGAA GCATAAAGTG TAAAGCCTGG GGTGCCTAAT GAGTGAGCTA    250
ACTCACATTA ATTGCGTTGN GCTCAACTGC CCGCTTTCCA GTCGGNAAAC    300
CTGTCGGGCC AGGTTGNATT AATGAATCCG GCCAACGCGC GGNGAGAGGN    350
NGGTTTGGGG TTTTGGGNGN TCTTCCGNTT CCTCGGTCAA TTGATCGTTG    400
GTCGGNNCGT CCGGTTGGGG NAANGGTTNA ANTCACTCAA AGGNGGGATN    450
CGGTNTCCAA GATCANGGGT TCCGAGGNAA NANATTTANN AANGGCANNA    500
AAGGCAAGAC CAAAAGCCNT TNGTTGNTTT TTNNA    SEQ ID NO. 57  535
```

Plasmid: 52

```
GAGCTCTACT AGANGCGGAG AGACGGGTGC GCGACGGAAA AATTCCGGTA      50
CCCTTTGTGG ATCGCGATAG CCTGTTGGCC AACGTTATTC CCGTCGCCCC    100
CANTCNCAAT CCGGAAACTG AAGGAAGACC GGAGAAGAAA GCACTGACAC    150
GACAGTGTTC GCTCCCTACC CCCCACCCTA AGAAGCTCGG AGTCCAGCCT    200
GATTCCGATA GCGACAGNGA TACGATTATC GATTTAACTA TGGAAGGGGC    250
GGTATCTCTG TAGATTNNNN NNNNNGNTGA ATTGTGCAAC CCGNATTGNT    300
TGGGTGTCAC TTGNAGACAA GCCTTCTTGT CAATCANTAG TGTNNTTTTN    350
GTAATAAACG GNTTNGTNGT TTAACAAGAA GNNNGGGTNT CTCATCTTCT    400
NGGGGGTGAT GAGNGNCTAC CCCCCTTNTA AAGNNATCGN TTANANTNGN    450
NGTNTNATTT GAGTTTTTTC ACCCCNATTT TATNNNTATC AANNTCTTNN    500
TTGGNTNTNN NTTCTAATNT CATNCCCN    SEQ ID NO. 58           528
```

FIG. 1Q

Plasmid: 53

```
GAGCTCGTCC TGGGGCTCGA TCCAAGCGNA ATTCACGACG GGGACTTTCA        50
AGTGTCTCTG CATCACAGTG GNGAAATAAC AGTCCTCGGT GGGTGGACTG       100
ATGGGNAAAA CGGTGTTCTC CTCGACGATT TTGTCTTTTG CGGNCCACAC       150
CGAAGGGGTT ACACTCCACA GATGGGCAAC GTCCTCGTCG GGACCGATAG       200
CCAGAAACTG CACATTGCGC GACCCGTATT GTTGCATCTC AGTCCGGAGG       250
GTCTCCCACT GCGTCGTTGG GAGGCGACAG NCGGGGTTT NCGATACAAT        300
TTCANAACTA AACTNGCCCN CCTTTGTCNG ATGGTGCGAT CAAACCCACT       350
CGTAAGGGTC GGNAGACCGN NTCTTTACAC AGGTCCANCG CTNGTGCCGC       400
AGNCNCCGNA TTAGTACATT TTNTNCAAAN ANCCCCTCTC AATTNAACTC       450
CCCAGGAGGC NANATTGGTT NAACCCCCAG ACGCATTAAC ACCNTNTTTA       500
AGNCCCCTTN AACNAAGTT TAANNCCCNC ATTTTANAAA AGCCNCTNTA        550
AAGCCANNTN CAGCCAATCA TGATNCAANC CTTTGGCCAA NCCCCTNCTT       600
CNCATTCCGG AANACTTTAG TCAAANTANC TTTNGTTNCC CCC SEQ ID      643
NO. 59
```

Plasmid: 54

```
GAGCTCCGNG TTTCACCCNC TCCGAGGAGT NTCCCTACTG CCACGNTAAA        50
TATGAAACTT ACCTCAGAGT CATGTCGGAC TTTCGNGAAC TGTTNCTGCG       100
ACAGNNCANC TTCGANGGAG TACGNTCGCG GGTGAGTGAC CACATCGATC       150
AAGTTATGTC ATATAGGAAN CCCCAGGAAC TGGNTCGNGC ACGTCAGGTC       200
CGGTGGACAC ATACCGGNNC TGAGAGATCA GCTGNTGGNC NGACAAANAN       250
CTNTTTTTTT TTTNTCTTNT TNCGNGGCGA CNGGANAATC NTATNCATGN       300
TGGGGTGNGG GACCCTCATG GTGGGAGANN GGGACCCCNN TCGTTNNCAT       350
NGGGGCNNNC CACCAANANT TTCATCTTAC NNCCCCCNTC AACNAATTTC       400
CTATTCAANG NNGGNTTNAN ATTTCCNCCC NACNNGNCNA ANNCCGNNTT       450
CTTCACCCNA ATCCCNTTTA ANNAANNTCN CANCNNCAAA CNCACCNCCC       500
TCACANCANC NCNTNNNTNC CCCTGCNNTN NNNCNCNNCN NANTTTCNNT       550
TT     SEQ ID NO. 60                                        552
```

Plasmid: 55

```
TTTTTGNCAN CCGTGAAGCT CAGGNCACCT TAAATCGTTA CTCTCACCTA        50
AAACGTGTTA GCATCTACGA TCCCCTGAAC ATTGGTGTTA ACTGTTTTGA       100
TTAAACACTT GACTCTTTGT ACCCGCGTGT CATGTGTGGT GTATCTGAGA       150
TGAGGGCCCC GCAACATATT TAGAGGTGTG GGCTCTTCAC GAACGATCGA       200
GAACTATGCG ACTTCGTTCG GAAGAAACGG AGACGGTTCG TTCCATCTTT       250
CTATTACGAG TTTACATTCT CATGTGGATC GAGGGCATGC TCTTGTTGAG       300
CACGTGCGCA CTCTGCTGGC TGGTGTTGCC AGAGCGCTTT GTGCACCTTT       350
TACCGAGTAT TCGTAGGANG TTATTTTGGT TTAATGCTTC CTATTATCTG       400
GNNGGGGAAT ACTTCACTTG GGCCCGAGCC TCCAGTTTCC CAGGGGAGCT       450
TGTACGGTCT TGTTGGANTT ACACGTCCAC ATGGCCNNNG GGGACACCGN       500
GCCGNGGNTT CAATCCGNAA ACCCNTCGAC CCCTTACGCC ATNNGGCTA        550
TATCTTGNTG NNATCNNNCC TNACCNTTTC AAGCTTCNTT NGGCNNAGNC       600
NNNGACCTTC ANCCNNGGN NNNGNCCCNC CNNCCNNATN NTNNCCNNAN       650
CNT    SEQ ID NO. 61                                        653
```

FIG. 1R

Plasmid: 56

```
GAGCTCACGT TAATGGCAAT TTGCAAGGGA ACACATCACC CACTGGCTGA        50
CTGTGGGATT TTTATTGGTC TCTTTACTTT TTAAGCGTTC TCGCCATCTT       100
GTGGCTACTT TCAATATTGC AGTTGAATGA TTGGGCACAG GTTCAACCAC       150
CTTGCAAATC ATTAACTCAT CTATTCAAGT ACTTNGGGAG ACTCTAATAT       200
CTCAAGTACT TACACAGAAA AGCAAGTGGA CAAAAGCAAA TAATAAGAAA       250
AAAGCCTAGG AGGAATTAAT GTAATTATTT TTCACTACAC TTTTAANCCT       300
CAAGTAGNCA GGCTTGTCGC TGCCAGAGGN CATCAAAACT TTTCCATTTG       350
GGNGGGGAAG GNNNGNTTGA CGCCTNTTTC AAAGATTGGG GGGNAAANNN       400
NGGNAGGNAG TCATTTGNGG TNAANNNGTN CNNNACCAGC NNGNCANATN       450
GNANNCCCCN CCTNTTCTNN AANANANATT NNCGNTNTTG NNCAANCNCN       500
NTNNCCCCCC NCNGGNNGGN NNNNATTNNN TCNNNGGG        SEQ ID     538
NO. 62
```

Plasmid: 57

```
GGGTTTTGAA AGCTCTTGAA GCTCACCAAC CCTTGAGGAG ACNAGTCGGC        50
GCTCGGGACT CACATCCCCC GACTCATTGC GCTCTTGGAT CACGACAACC       100
ATCGCGAACT GTGCAATGTG CTGGTCGGGC TGCTACACCA GAACACCCCA       150
CATGTGGGGC CGTTCCATCC GGCTTATCGG GCGATTAAGA AACTATCTAC       200
AACAGAAGTT TCTCAATATC TTGGTGGATA GCGGACTCCA GATCGATAGT       250
CTTTTTGAGG GTTGTTACCA CAGCGAAGCG TACCGCTTGC TGTTCCAGAT       300
CGAAAAAACG AACTCCACGC CTAGCTCTCT ANGCTGTGCA AGCACCGTTT       350
TACCTGTCGG TGAAAACGAA ACTGAAGGNA NACCTGTCCC CGNCGGCGTN       400
TTTTANTGAA ATNCTNAAAT GGCTCTCATG AAATATGACG GCCTTAGTTT       450
CGTNTTNGGA NNGGANAATT NTGNNTCTCC CCCCAAACAT NCCNGNCNTG       500
GNCCCGTGNN TTNGACCCTG AACTTCCGCG GGGNCCNNT NNCCTTNTGA       550
CAAACNGNCA NTTCNTTCNT NGNTCTCGTA NCCCACCNNT TTAGCGGTNT       600
NNTGG    SEQ ID NO. 63                                       605
```

Plasmid: 58

```
GNTTGCAACT TCTCATAGNT CAGACACCCC CTNANACAAN TTGGCGGCTT        50
GTTCGAGTCG TGTCCGCATG GACTGGAGTT CCTCAACGGG CAGGGCAGCC       100
ACTAATGATT TGATTGTATC TTCTTTGCAG CATGGCGGTG NTTTGGCGTT       150
TAAGATCTCC CTGCAGTTCG GTTATTNTTG TGTTTCCTCG NTGCAGTAGT       200
GTCGTCTGCG CCTGACTATC GANTTTCGAT AGGATCTGTT TTGTGTCTTN       250
GTTGTCGAAG GAGATTCTTT CCAGGTCGTG ACTATCGATT CCATAGATGG       300
CGGCAGATAG CTGCTGTAGC GCTAACTGGA CCTGTTTTTG CTGTTGGCTG       350
GTGATCTGTC GNCGACCGNT GACGGCATTC ACTACCGCCG AAAAGTCTTG       400
TNGTNGAAGG CAGACGAACC TTTCGNCGAC GTCAANTGGC TTCTCCTCCN       450
CNTNTTCCCA GCAGNCCCNA NAGGGAAGTN CCGTATTAGN AGGNTTCTNC       500
CTTCCGGCCT TCAAAATCT GNCGAACCCA TTTCAATAAC CTTTNNGCCC       550
CAAAANTGNA ACCTANGTNA ATAAAAACCG CGGCAAAGTN NGCCTATCAT       600
ACACCCCNTT GTACGGTAAA CTTTAAGNTT AAAANTTTCA AANTCTCGCC       650
ACCCANAGTG AATCCNTGCT AGCNANGAAA GGNTNNATCG ATTCNCTCAA       700
ATCCCNANTT CNCCCCCNTT NAATCCANNN TT    SEQ ID NO. 64         732
```

FIG. 1S

Plasmid: 59

```
TNATTGNATA CTCTTAAGCT CTCCGGCCCC GCCNAAAACC ANATTTCTCG       50
TTCGCTAGTT GGCTGNCCAT CANCTNGCTG TCATTCCTTT TTAATCAGTG      100
CAACGAGTTC TGGGGGTGGT TGGAATGGCT CGCCCTCCGA GAGNGAGGAA      150
ACATCGTCGC TATCTCCTAC ACTACCGATG TGTAGCGGAG ACGACGGNTG      200
GGTATGATCG NCGCCATNCN TNTTTTNATC ANNCTCCTCG GNGTCGNNCN      250
CCTCCNCTCC GGTGTCCTCG TATTCATCCN CGGTCTCCTC GACACCTCTC      300
AACGTACTGG NCGNGTNACC TTNAGATACG CNANACACGN NAANGCNCCN      350
AGACTNCGNN GGTGGATTTT NTTTTNTTTT TCTTCCCAAA NCCACTNTTC      400
CGGNGGTCCC NNNCANTCCG NCTCCATAAN TTCATCCCNN CNNTNTNCNN      450
NNCCCATCTN GGGGNNTTCT TTGNAATCAG AACCNGTNNG NAANACACNN      500
TAANNNCNNT TCCNNNTAAN NNGCTNNCCT CTNNTAACCT NTTCCNANNA      550
NNCTNTCCTN NCNCNNTTTT TCNNATNCAT NTCACTCTTC TNCNNTTNTN      600
CCTNCTTCNN NCTNNCCCTT CCNNTTTCNC NACCTNNTNT NANCTCCNCT      650
CNNCCCNCTA TCNNCCNTCT ACANCNACGN CNTTACCTAC ATTNTNCAA       699
SEQ ID NO. 65
```

Plasmid: 60

```
GAGCTCCATC TCTGTAAAAC CGTGGCCGCT CATAATGCGA TGTTGTGCCC       50
TCGTTTCGGG AGCGTTGATC GTTCTAAGCT TAGTTCGGNA AACAGTCTGT      100
CTTATGGTGT GGGTAGTGGA TGTGCACTTG ACGTCATTAT GTGCGAGAAT      150
CGGAGGCGAA CCACCAATTG TACCGATTTA GCTTGAAGGT GAAAAAAGAG      200
GAATGGTTAG TCTGCCAAAA GACGGNATCC GAAAATCATG AGTCCAGTAA      250
TATACAATGA TGAGAATTTC CACGGTACAA AACGAATTAA CAAGGGGAAC      300
GGCTCCACCG AGAAACTCCG TACTTGAGCG GGGGANAGGA AGTCNGNNGG      350
NTAGAAAGTC CCGGGGGAGA AAGTTAACAA GNAGAGCCAA GGTAGCANCC      400
CNNCCCATTT TNTTTAAAAN GATGGACTNT TGGGGAGGGG NATTNNCANN      450
AANNNGTTTG NANAAANATC AAGGGAANAA GCCNCCCNAA ANNTTNACCC      500
CCCCGGAANG GNCNGGTTCC CGNTTTTTAA ACNNTGTTTT CCNAAAATTA      550
AATTANNAAA A    SEQ ID NO. 66                               561
```

Plasmid: 61

```
GAGCTCATGN CACNCTGGAA NAAAGCAGTT TCTTGATCAA TCGTAATGTC       50
ATACACTTTC CTCAACAATT CCTTCTCATT TAGAAAGACA GAGTTGATCT      100
GAATGTGAAA CCACACTGCA GGGCTTATCC TAAGCATAAA GATGTCCTTT      150
GGGAGTCTTT TCAACGCTTA AGCTATTCTC AGTCAACCCA GAAGAGGGTG      200
CAGGCAAACA CACAGTGACT CCAGTACCTG GAAATTGCAG CTTGCCTCTC      250
TTGTCACTGA CTGTTTTATT ACTTAGTGT CTGATTTTA TGAATACTTG       300
CAAGTAACTA CAAGGCACAC CCTTTTAATT ATAGTTTTAT TCATTCACTC      350
AGACAAATTA AAGGAACCCT ATTAGCTGGG CTATTTAAC AAGTTTATGA       400
CATACAGATA TGTCTTGAAA ATTTACATTA ACAGGGTAAA AGGCTGGATN      450
TNTCAACTTN CTCTGGGGGG GCTGGTATTA CTTNATGCCN TNAAANTGAT      500
TATTCCCTCN CTTTNCCCCA TACAACCCCG GATTAGGAAA GTAAACCCNG      550
GTGAAAGGAT TTTCNTTGGC CCCTNACTNT TTNCAAGAAT TTTAAGGNNT      600
GGNAATCAAA ATAGGTGGGC CCCCCGGNGG NGGCAGCCCT NN   SEQ ID     642
NO. 67
```

Plasmid: 3B11 T3
Accession 1: U27475

```
GAATTCAGCG TGTCGGAAAC GCTGTATATA TGCGAGTGGG CCGGGTATCC        50
ATGACGTTGA TTTGCGTGGT TTGTGGTTAC TGATCGGCTG TCGGCGGTCG       100
CATTTCCACG GAAATGTGCA CGTNCTTCGC GTTCCGAATN ACATTTTTTG       150
GTAAANCAAG CNGCTCCAAA GACTNGGCCA CAGGGGNGTA GGTTATGTTC       200
NGTGCGTANG ATCNATNAAA CAATTGGACC GGTNTCCCTG TGGGTTTGNC       250
GGGGGNTTAT TGNNGNAAAN ANGCGGAANC CCCCTNGTTT CNCCAACCCT       300
CTTTNCCCCT TGGAACCCAA AACNCAGGTG NGGGCCCCTC NNNGNTTNTA       350
AACCNTCANA CTTTTTTTTG GNGAAGGCAA NCCNTCTCCG GTTCANTNTN       400
GGGNTTCCCA GGGCTTGGNT CNNANTTTTT CCANNNAAGA AACNGNCCCN       450
AANNTNTTTT AAACNNACAA CCCCNTAAAG GCCCGNNGGT NTCNCCCGGT       500
TTTCCCNTTT TCTTGGNCGC TTTCCNCCCC CCCTNNAAAT TGNTAGTTTA       550
TTANNCAACN ANGTTNGNTT TCANAGNNCA AAGTCAAGCC CTTTCCANNT       600
TGTTTTGGNN GGCAANTTTC GGCANTANTT TTTNGGTNTT NGANGGNCTT       650
TTNANAACCN NNGGGGNCGG TTTTNTNAAA TTTANNNCNN TTTCCCCNAN       700
TTCNTTATTT CTNCCCNCCC GGGGNNCCCC NCCN   SEQ ID NO. 68       734
```

FIG. 2

Plasmid: 3B11 T3

```
GAATTCAGCT TGTCGTAATC TCTGTATATA TGCGAGTTGG CCGGGTATCC        50
ATGACGTTGA TTTGCGTGGT TTGTGGTTAC TGATCGGCTG TTTTAGTGA         99
SEQ ID NO. 69
```

FIG. 3

Plasmid: 3B12 T3
Accession #: U27476

```
CNNCNTTNNN NGACACAAGC TGGAGCTCCA CCNCGGTGGC GGCCGCTCTA        50
GAACTAGTGG ATCCCCCGGG CTGCAGGAAT TCGAAGTGTT GACCAGCGTG       100
ACTGTAGCTA CAGTGCCCGG TAGCCAAATT ACAGGACGCG TGATGAGCCC       150
TAGCTGCGCC ATGTGGCGGG TTCCCACTAC GAGGGCGCAA GTGCTGGGGG       200
CTTGAATAAA GGCGGTGTCA AGGTACACCG TGTGGGTGTA ATTGGGTTGG       250
ATGATAATCC GTTGCTGCAC ACGTAGGGAG AAGAAGTGGT TTTCGTTTGG       300
GGGTGACATG TTCATGAGTT GCCAGGGCTC GGGACGGAAA CAGGGGAAGA       350
TGCAGATGTC GCCCTCGATG GTGCCCGGNG TGATGGCTTG GAACGTGTAG       400
TTAAGATTAA TAACTTCCAT GCTGAGGTTT CGTAAGCCGG GTTCGATGAA       450
TTCTGGCATG NAACAATTTG AGAATCCAAA CATTTATTAA AACGTAATTC       500
CGAAGTNTCC NATGGGATTN TAAGGTTGAT GCCNAGGGTG TTGAAGTNTT       550
GGNTGGTCCG GTAGCAATAT GTTTGGTGGA ATTNATGCTT TCTTGGTTGN       600
GAAAATTGAG GGTCCCTTTC GGATTTNGGC NNGNNAATTT CCNCN   SEQ     645
ID NO. 70
```

FIG. 4

Plasmid: 3B12 T3

```
GAATTCGAAT TGTTGACCAG CGTGACTGTA GCTACAGTTC CCGGTAGCCA   50
AATTACAGGA CTCGTGATGA GCCCTAGCTG CGCCATGTGC GGTTCCCACT  100
ACAGGGCGCA AGTTCTGGGG GCTTGAATAA AGGCGGTGTC AAGGTACACC  150
GTGTGGGTGT AATTGGGTTG GATGATAATC CGTTTGCTGC ACACTAGGGA  200
GAAGAAGTT      SEQ ID NO. 71                            209
```

FIG. 5

Plasmid: 3B12 T7
Accesson #: U27874

```
GAATTCCTAG CCAGCTGTAT GTCCAAAATA CAACCGCGCA ACCACTCTGC   50
TCATGTACCC TGGTGCGGTT GAACTAGCTA ACAGAACTTT AAAAACTAAC  100
GGAGACATCT CCAGCGTCCT CACCGTAGCT CGGCTGGTTT ATGTGTTAGT  150
TAAGCAAAAC CGTCAAGACC TGGTTACGCA CACCGCCATG CAACACGTCC  200
GTGACCTCAT NNTGCGTCTC CATAAATCAC ATATAGCTTC TTTCCTATCA  250
CGGTTTGCTC GCCAGGAACT GTATCTTGCC AGCAGCATTA TTCATTCCAT  300
GCTAAATTAC TCTACCGAAA GACGAGACAT ATTTGTCTTC GAAACAGGAT  350
GTGTTCACTA GCTGAACTCT CACACTGGTC ACAACTCATC GGNGGCCACG  400
AAAACGTCAC ATCAGCGATT TNTCAGTCCA TGCGTTGGAG NGGGGNAGAG  450
ACACGCCTAG ACACTNTNTA CATGTTNCAA AGNACTATCT GGACCTAAAA  500
TGTCTTTTTT TAGACTTAGC AAAATTTCAT CCAGATAATN TCCAGGGAAT  550
TNGGCGTTAA AGTCCNTGAA              SEQ ID NO. 72        570
```

FIG. 6

Plasmid: 3B13 T3
Accession 1: U27610

```
GAATTCCATC CCCCCGATGA ATTTGCGGCG ACTGGCGGCG TGCCGCTGAG   50
CCGCCAGCTG TTTGTGCCGG TGGTGTTCCT GAGCGGCCTG GCGCAGGGTG  100
TTGCCGGTAA AATCAAAAGC GCTGCCCTGC TTCTCTCGAC GCCACAATTG  150
TCCATATCGA ACGAACATGA GTCTAGAAAT GATACACACG TACCGCTTTA  200
GGCGATCGCC GCTCGAGTCC CGGCGAACTA CGCTATGCGT TCGCGCCACC  250
AGGGACGACG ACGCACCGGG AACACCACCG CAGTGGNGAG AGGAGGCAGG  300
AGGGGGATGA TTTTTGTTTA TAGGCTCGGC CTTANCGATT TCATAGTACA  350
CATAGAATAA ATTACGNCAG ACGGTGTCAT GCTCGCCGAA AGCCAGACTC  400
AAGCGCCGGT ANANAGTATT TTCCCNTACA AAACCGNTTG GTNTTGGCGT  450
AGGTGATGNN AGNTTAAGTC AANATTGGNG TTAAACGCCA GGTAAGTNAT  500
GAATGAANGT GGTCCGAGGA ANGCACATAG NTCCCANCCT TAATCCGNGA  550
GAGGTCAAAN CCT                     SEQ ID NO. 73        563
```

FIG. 7

Plasmid: 3B13 T7
Accession 1: U27875

```
GAATTCGTAC AATCTCACCC AAGAGTTGTC GTTAGTGGAG GACGCTCGGT        50
TTTGCCAGAC GCGGCCCGTG AACGCCGAGC GCGTTCGCGG TGTCTTCGGC       100
GCGCTCTATC GCGCCGCGTC CCCGCACATG CGGGAGGAGA GTGACCGCAT       150
CAAGCTGATT TTGGGACGCT TGTTGCTGGG ACCCGTGGCC GTGCCCTGCT       200
ACTGTGACGA ATGGGAGGCG AATGACTACA TGGTGGAGGC GGCGCAGTTT       250
TGCACCGGCC CCCTGCTGTA TGTGNACCGA CGCTGCCACT GTCCCGGTAT       300
GGGGGGCGCG CTCGCTTTCA CCGTGATGGA AGGGCATNTC GCGACGCATN       350
TTTTTAGAGG GNTGCTGTCA CTCACTGAGT GGAACCAGNA CTGCCCCACA       400
TTTTTTGGCC NTGCNGAACG GTGANCAGNG GGATCGGACA NGAATNGCTG       450
TCTNCCCGNN AACTTACGTT TTNTNTAAGG AATATCCTAA TTATGGGGAG       500
ACGGGTTTCT CACCNATAGG GTTATAGTAT NTATACAATC TGGGANCCNA       550
NCCCCNCTAA TTAAAAAATT TNGTGGGTA      SEQ ID NO. 74           579
```

FIG. 8

Plasmid: 3B412 T7
Accession #: U27888

```
GAATTCACGT GTACGGGGAC ATTGACGACC TGGGGTTCCG CCGCCGACTC        50
CACTATTAGA GCGTCCTGGG GCGCGCGACA CTGAAAGACG GTTGGCGAGG       100
AAGCCATCGC CGCACGCCGT CATGGAAAAC TGGACGGCAG TCGAGTTACT       150
CCCGAAAGTC GGGATCCCGG CCGACTTTCT CACGCATGTA AAAACCAGCG       200
CCGGGGAAGA AATGTTCGAC AGTCTGCGCA TTTACTACGG AGATGACCCG       250
GAACGCTACA ACATCCACTT CGAAGCCATC TTCGGCACCT TCTNCAATCG       300
TCTCGAATGG GTTTACTTCC TCCAGACGGA CCTGGCATCG GCNGCGNACG       350
CCATCAAGTT CGATGACCTG AACAAGATGA CAACAGGGAA AATGGTTGTT       400
TCACATCCAG NTTGCCGCGT NTNGGCAGGG NGCCGGAATG CCANCTCGAC       450
CAGACACCAC ATNGTTACCA ATNCAGTAAA AAGCCCCTCA CCNCCCCTC        500
NCCTCANGGC CCCTTTTATG ACCTGGAAAN NTCNGACNCA ACCCGANGTC       550
NTATTTCGAG CNNGAAACCA CTTNNTNTTN NAAANC    SEQ ID. NO. 75    586
```

FIG. 9

Plasmid: 3B413 T3
Accession #: U27622

```
GAATTCTGTA ATCCATGCCA CTTGATTGCG ATACGTTTCA TGCAAGCTGG        50
GTTGCAACTG TTCTTAATCT CGATTGGCCG TCGCGGGCTT CCACTCTCAT       100
TGAAGATGAT TCCGAACGGG TAAAGCGTCA GAAAAAGAG CTGGTGCGGA        150
TGTTTGATGA GGCGTCGGAG CATGGCATCA ATGCCATGAT TTTTCAGGTC       200
TCTCCTGCTG CCGATGCTTT CTATAAATCG GAGTATCTGC CGTGGTCGTC       250
TTATCTCACG GGTACGCTCG GAAAAGATCC GGGCTTCGAT CCACTNCGCT       300
TTGCAATTGC GGAAGCGCAT AAGCGCGGGA TCGAGCTGCA TGCATGGCTC       350
AATCCTTATC GCGTTTCGAT GGATGTGCGA CCAGCAACGC GGAAAGNACT       400
GAAAAAACTC TGCCGGCGAT TCTCCGNCCA GCGTCTATAA AACCAATCCA       450
GGCTGGGTNG NTTATNTCTG CGGATCCNTT ATGTGTTGGA TCCGGGTNTC       500
CCGGATGTTG NCAGTGGNTG AGAATTTAAG GCCGAAGCCG TCANAATTTA       550
TGTCGAGGAT CAGTCC                       SEQ ID NO. 76        566
```

FIG. 10

Plasmid: 3B413 T7
Accession #: U27888

```
GAATTCATTC ATCTTCATGG GGNAGNAGAA AAATGAACAT CAGGACCAGC        50
TTCCACATTG ACACCATGGC TGTCACCATG CTCTTTTTCA ACGGGCTGTT       100
CAACCTTAAC ATCTTTCGAG ACGTAGTGGC CGATGACTCA CAACAAAAAA       150
GTTGTGATTA TATGAAACAA CAACACTTTT TNCGCACGAT GGGTATAGCC       200
TCTGTGTTTC TCAGACCCGT CTTTAGTCCT ATCATTTACA TATGTGTCAG       250
TCGNAAAATC ATACAGGGTA TCTGCAAATT GTTTATAAAA GTACCAAACC       300
ATACCATAAG CTCGGAACGT GTAAAGCTTA TGTCTCCAAA TAGAATGAAC       350
GACGATGCCC CAGAGCTTCC GCCCAGGGGA ATATGAATCC GCGTTCTANA       400
TTATTGCGCG TTGGTAGGGN AACGACACAA CCAGCCGATT TNTGTTTGGG       450
ACCGGTCACA ANCCCCCGAC ATTGGAAATC GACATTGTTC GGTTGGNGAA       500
CAGNCTTTTT ANAACATGAA CAACTCCCCC GTACCCTCTG AAGTGTTAAG       550
ACGCGAGNAT TCGGAGTAGG               SEQ ID NO. 77           570
```

FIG. 11

ISOLATED STEALTH VIRUSES AND RELATED VACCINES

RELATED APPLICATIONS

This application is a continuation-in-part of U.S. patent application Ser. No. 08/157,811, filed Nov. 23, 1993, which is a continuation-in-part of abandoned application Ser. No. 07/887,502, filed May 22, 1992, which is a continuation-in-part application of U.S. abandoned patent applications Ser. No. 07/704,814, filed May 23, 1991; and Ser. No. 07/763,039, filed Sep. 20, 1991. These prior submissions, including any drawings, are incorporated herein by reference in their entirety.

FIELD OF THE INVENTION

The present invention relates generally to the field of virology and relates more particularly to isolated viruses and related vaccines.

BACKGROUND OF THE INVENTION

A. Chronic Fatigue Syndrome

Palca, *Science,* 249:1240–1241 (1990) and Palca, *Science,* 254:1726–1728 (1991) describe attempts to identify a causative agent for chronic fatigue syndrome.

DeFreitas et al., *Chemical Abstracts,* 114: Abstract No. 205331c (1991) describes retroviral sequences related to human T lymphotropic virus type 2 in patients with chronic fatigue immune dysfunction syndrome.

Gupta et al., *Scandinavian Journal of Immunology,* 33:319–327 (1991) describes a comprehensive immunological analysis of chronic fatigue syndrome. The analysis of cell mediated and antibody mediated immunity was performed in 20 patients with chronic fatigue syndrome and 20 age and sex matched healthy controls.

B. Culture Techniques

Werner, *Lancet,* II:258–259 (1979) describes the isolation of foamy viruses from patients with de Quervain Thyroiditis and the detection of a cytopathic effect.

DiLuca et al., *Virology,* 175:199–210 (1990) describes the replication of viral and cellular DNA in human herpesvirus 6-infected cells and the use of medium RPMI 1640 containing 10% fetal calf serum.

Ablashi et al., *International Journal of Cancer,* 42:787–791 (1988) describes the use of human hematopoietic cell lines for the propagation of HBLV (human herpesvirus 6) in RPMI 1640 supplemented with 10% FBS and antibiotics.

Rethwilm et al., *Nucleic Acids Research,* 18:733–738 (1990) describes an infectious molecular clone (pHSRV) of the human spumaretrovirus (HSRV). pHSRV derived virus produced foamy virus typical cytopathic effects in susceptible cultures.

SUMMARY OF THE INVENTION

The present invention provides a novel isolated virus, termed a "stealth virus", and related vaccines. The isolation and in vitro culture of stealth viruses and development of vaccines is described in commonly owned international patent application publication No. WO 92/20787, published Nov. 26, 1992, incorporated herein by reference in its entirety including any drawings.

The invention includes viruses that have been isolated using novel culture techniques and improved methods of isolation are described herein. The novel culture techniques encompass a method for detecting a stealth virus by culturing a sample under conditions that induce a cytopathic effect. Several culture conditions are sufficient to induce a cytopathic effect in a sample containing a stealth virus. These culture conditions include replacing the culture medium every 24 to 72 hours, adding 5% to 10% fetal calf serum to the culture medium, using serum free medium X Vivo-15, using preculture centrifugation and adding viral enhancing medium to the culture.

In one aspect the present invention provides an isolated, purified, or enriched stealth virus corresponding to a virus whose presence in a subject having a disease is positively correlated with the presence of neurological, psychiatric, rheumatological or other symptoms or signs of illness attributed to the viral infection. These illnesses can include cases diagnosed as chronic fatigue syndrome. The terms isolated, enriched, and purified are meant to cover only those situation in which a person has intervened.

By "isolated" is meant that the stealth virus is removed from its normal cellular environment. The stealth virus is preferably the predominate virus present in the sample (at least 10–20% more than any other virus), and more preferably is the only virus present in a homogeneous suspension or sample.

By "enriched" is meant that the stealth virus constitutes a significantly higher fraction (2–5 fold) of the total amount of virus present in the cells or solution of interest than in normal or diseased cells. This could be caused by a person by the preferential decrease in the amount of other viruses present or by the preferential increase in the amount of stealth virus present, or by a combination of the two. Thus, the relative amount of the stealth virus is preferably significantly increased by a useful amount, usually about at least 2 fold and preferably 5–10 fold or more.

By "purified" is meant that the stealth virus is relatively more pure than in the natural environment, preferably by at least one order of magnitude, more preferably 2–5 orders of magnitude, and most preferably the stealth virus is a homogeneous preparation.

Stealth viruses may be isolated from a sample of blood or other biological samples including surgical and fine needle aspiration tissue biopsies, post mortem organ biopsies, throat swabs and saliva, urine, cerebrospinal fluid (CSF), other body fluids, blood and blood products intended for transfusion or for in vitro uses, vaccines, foods, and from the environment.

The term "stealth virus" refers to a virus having all of the following characteristics: (a) the ability to induce a cytopathic effect in fibroblastic cultures, including primary kidney cell cultures, which is characterized by the production of enlarged, foamy appearing cells, including cell syncytia; (b) the ability to produce inhibitory compounds capable of suppressing viral growth; (c) the ability to grow in cells from a plurality of species; (d) the ability of viral-specific typing antisera to distinguish stealth viral infected cells from cells infected with human cytomegalovirus, herpes simplex virus, human herpesvirus-6, varicella zoster virus, Epstein-Barr virus, adenoviruses or human T lymphotropic virus (HTLV); (e) the ability of virus specific nucleic acid probes to distinguish stealth viral infected cells from cells infected with human cytomegalovirus, herpes simplex virus, human herpesvirus-6, varicella zoster virus, Epstein-Barr virus, adenoviruses or HTLV, using stringent hybridization conditions; and (f) the ability to cause disease in an immunocompetent host without evoking an inflammatory response throughout the infected tissues.

The term "cytopathic effect" (CPE) refers to the appearance of rounded, slightly enlarged, refractile cells throughout the culture. In some cultures the CPE progresses to very prominent collections of tightly packed, enlarged, foamy-cell appearing cells, with clearly defined cell syncytia and evidence of considerable cell destruction. Stages between the spindle shape of the normal fibroblasts and the rounded appearance of affected cells can be seen. Several inclusions, consistent with vacuoles, can been seen within the cytoplasm. As their numbers increase, affected cells form several tightly adherent clumps with indistinct cell boundaries. The affected cells continue to proliferate and scatter away from the cell clumps.

The term "chronic fatigue syndrome" (CFS) refers to an illness whose major characteristic is an unexplained fatigue lasting beyond 6 months which results in greater than 50% reduction in an individual's normal level of activity (Holmes et al., "Chronic fatigue syndrome: A working case definition," *Ann. Intern. Med.*, 108:387–389 (1988); Holmes, "Defining the chronic fatigue syndrome", *Rev. Inf. Dis.*, 13 (Suppl. I):S53-5 (1991); Shafan, "The chronic fatigue syndrome" *Am. J. Med.*, 90:731–738 (1991)). To establish a clinical diagnosis, the patients should show evidence of suffering at least eight of the following minor symptoms: fever, sore throat, myalgia, muscle weakness (which may be exacerbated by exercise), arthralgia, lymphadenopathy, sleep disturbance, headaches, acute or subacute onset, and neuropsychological symptoms. The neuropsychological symptoms include a difficulty in thinking, dysnomia, confusion, forgetfulness, irritability, depression, photophobia and transient visual scotomata.

In preferred embodiments the disease is selected from the group consisting of multiple sclerosis, unexplained encephalopathy, acute encephalopathy, psychiatric disorder, Alzheimer's disease, fibromyalgia, myositis, muscle neuritis, chronic pain syndrome, salivary gland enlargement, autoimmune disease, unexplained hepatitis, vasculitis, including arteriosclerosis, autism, attention deficit disorder and chronic fatigue like syndrome occurring in both humans and animals including domestic cats and dogs. Preferably, the virus has similar growth characteristics, but not necessarily molecular relatedness to the stealth virus contained in the MRC-5 cell line deposited with the ATCC and assigned accession no. VR 2343 and/or is in an infected human or animal cell having all of the identifying characteristics of the MRC-5 cell line deposited with the ATCC and assigned accession no. VR 2343.

The stealth virus preferably has a nucleic acid sequence corresponding to any of the plasmid sequences as set forth in the figures attached hereto or at least 9 contiguous nucleic acids thereof, preferably 12 or 15 contiguous nucleic acids thereof, more preferably 18 or 27 contiguous nucleic acids thereof, most preferably 50%, 100%, 150% or more contiguous nucleic acids thereof. Especially preferred are those with at least 60%, 80%, 90%, 95% or more similarity or identity to the sequences shown in the figures.

In another aspect the invention provides a vaccine comprising an immunogenic amount of a stealth virus antigen or fragment thereof containing an epitope, in a suitable vaccine carrier.

In preferred embodiments the vaccine has an isolated attenuated stealth virus such as an attenuated derivative of the virus as contained in MRC-5 cells deposited with the ATCC, and assigned accession no. VR2343.

In another aspect, a method of detecting a stealth virus is provided by culturing a sample under conditions in which any stealth virus in the sample is able to induce a cytopathic effect.

In preferred embodiments the presence of the stealth virus is detected by (1) inoculating a permissive cell line with a sample, and (2) detecting in vitro a CPE in the permissive cell line; the cell line is maintained in culture medium that is replaced every 24 to 72 hours; the cell line is an insect cell line e.g., the cell line is derived from a plurality of species and may even include Spodoptera fruiperdo insect derived ovarian cell line Sf9; and the sample is from a patient suspected of having neurological, psychiatric, rheumatological or other illness including the chronic fatigue syndrome (CFS) based upon other recognized criteria well known to physicians in the art.

A cell is "permissive" if a particular virus causes a productive infection in it. A productive infection is a viral infection of a cell that produces progeny with the vegetative or lytic cycle. A productive infection by a stealth virus is characterized by the appearance of a cytopathic effect. Using appropriate conditions, stealth viruses infect and propagate in many mammalian cells in vitro, especially cultures of fibroblastic cells including the fibroblastic component of primary kidney cell cultures, and other cell lines of epidermal, mesodermal, neuroectodermal and lymphoid origin, e.g., glial cells, myoblasts, etc. The distinctive CPE is, however, readily observed in fibroblast containing cultures. At present, therefore, these are the preferred cell lines to isolate the virus from clinical and animal samples. Suitable cells include human MRC-5 lung fibroblasts, human foreskin fibroblasts MRHF, primary and low passage rhesus monkey kidney RMK cells, and cynomomgous monkey kidney cells. These well known cell lines are available commercially (e.g., from Whittaker Bioproducts, Walkersville, Md.). It should be noted that not all cell lines are permissive for growth and/or for the expression of a cytopathic effect (CPE). Conversely, other cell lines may be more efficient in promoting the growth of stealth viruses than the fibroblast cell lines currently used. The tissue culture cell lines are maintained in the laboratory using methods well known in the art.

In another aspect a method of detecting a stealth virus is provided by: (1) inoculating a permissive cell line with a sample; (2) neutralizing stealth virus-associated inhibitory and toxic activities; and (3) detecting in vitro a cytopathic effect in the permissive cell line.

The term "stealth virus-associated inhibitor" or "inhibitor" refers to the molecular entity (or entities) that mediates the viral growth inhibitory activity observed in stealth virus cultures in vitro, and which appears capable of suppressing stealth virus growth. Cultures with inhibitor are often more difficult to infect with other stealth viral isolates. The term "stealth virus associated toxin" or "toxin" refers to the molecular entity or entities that mediate the toxic activity that may be observed in stealth virus cultures in vitro. The toxic activity is detectable in serum and cerebrospinal fluid from stealth virus infected patients and may mediate certain symptoms associated with the patient's illness.

In preferred embodiments the inhibitory and toxic activities are neutralized by frequently replacing the culture medium, using medium in which the production of the inhibitor and/or toxin are minimized, or by adding a neutralizing or counteracting agent to the culture; the neutralizing agent is fetal calf serum or retinoic acid, an antibody specific for the inhibitor/toxin, or a chemical or virus derived agent capable of competing with or reversing the toxic activity; and the sample is derived from a human, animal, food, or other environmental substance or object.

The term "neutralized" refers to any amount of inhibition or decrease. Thus, by neutralizing the toxic activity, one actually increases the detection of stealth virus. The term "replacing" refers to removing old culture medium which is suspected of containing inhibitory/toxic activity and transferring new culture medium into the sample being tested to provide a new culture medium.

In yet another aspect, a method for detecting a stealth-virus is provided by: (1) inoculating a permissive cell line with a sample of the virus in a culture; (2) adding serum free medium to the culture; and (3) detecting in vitro the presence of a CPE in the permissive cell line.

In preferred embodiments, the serum free medium is medium X Vivo-15 (BioWhittaker, Inc., Walkersville, Md.). X Vivo-15 is a Iscove's modified Delbecco's medium with the addition of human albumin, human insulin and human transferring. Iscove's modification of Delbecco's medium is intended to support high density cell growth and has additional glucose, salts and vitamins compared to Delbecco's medium (Iscove and Melchers, *J. Experimental Medicine*, 147:923 (1963)). Albumin, insulin and transferring are provided as a replacement for the need for serum. Since these proteins are of human origin, X Vivo-15 is suitable for growing human cells and for producing human cell derived products intended to be injected into human recipients.

Of several serum free media tested, medium X Vivo-15 was superior to medium 199 plus 7% FCS for supporting stealth viral growth. The CPE developed more rapidly and there was less of a general loss of vitality seen with the usual stealth viral cultures. Medium X Vivo-15 was also found to be superior to other serum free media, for example, Aims-V medium from GIBCO BRL, Gaithersburg, Md. Aims-V medium also uses human albumin, insulin and transferring, but the basic salt component is F-10 medium (Ham, *Exp. Cell Res.*, 29:515 (1963)), rather than Iscove's. X Vivo-15 was also superior to medium 199 plus bovine albumin, insulin and transferring, with or without FCS.

In still another aspect a method of detecting a stealth virus is provided by: (1) co-centrifuging a sample of said virus with a permissive cell line of indicator cells; (2) inoculating the cell mixture into culture vessels; and (3) detecting in vitro a CPE in the permissive cell line.

Pre-culture centrifugation (PCC) of patients' lymphoid cells with indicator fibroblast cells refers to co-centrifugation of patients' or animals' lymphocytes with freshly harvested fibroblasts and replacing the cells back into the original tubes containing the fibroblasts.

In preferred embodiments the method involves adding a viral enhancing medium (VEM), including cytomegalovirus (CMV) supernatant, to the stealth virus culture and frequently refeeding the culture medium. Viral enhancing medium (VEM) is derived from the supernatants from actively replicating viruses which are functionally related to the stealth virus. Filtered, boiled medium collected from a CMV positive MRC-5 cell line showing a well defined 2+ CPE was able to supplement the stealth viral growth activity of medium X Vivo-15 used alone and was designated VEM for "viral enhancing medium". Titration of this medium showed that 20%–30% was adequate to provide significant growth enhancement. X Vivo-15 medium containing 20% each of both CMV and HHV-6 supernatants was more effective than medium containing 20% or 30% CMV supernatant.

In another aspect, a method of detecting a stealth virus is provided by: (1) inoculating a permissive cell line with a sample of said virus in a culture; (2) adding viral enhancing medium to the culture; and (3) detecting in vitro a CPE in the permissive cell line.

In preferred embodiments the viral enhancing medium contains 30% boiled, filtered products derived from the supernatant of cultures of cytomegalovirus and 70% medium Vivo-15; and the cell line is maintained in a culture medium, that is frequently replaced.

Another aspect provides culturing a virus by: (a) centrifuging a sample of said virus with a permissive cell line of indicator cells; (b) inoculating the cell mixture into culture vessels; (c) adding viral enhancing medium to the culture; and (d) detecting in vitro a CPE in the permissive cell line.

The PCC step in combination with the use of VEM will also improve the detection of the CPE associated with cytomegalovirus (CMV) and human herpesvirus 6 (HHV-6). The growth of CMV and HHV-6, however, are less dependent on these modifications than that of stealth viruses. Furthermore, frequent refeeding of the cultures is not nearly as important for these viruses as it is for stealth viruses.

In the most preferred embodiments the virus is a stealth virus, but similar culture adaptations can be used to enhance the growth of cytomegalovirus, or human herpesvirus-6.

The summary of the invention described in detail above is not intended to limit in any way the scope of the present invention which is defined in the appended claims.

BRIEF DESCRIPTION OF THE DRAWINGS

FIGS. 1–11 show the nucleic acid sequences of various plasmids obtained from a patient with a stealth viral infection. The techniques used to obtain such sequences are generally described in Appendix A and Martin, et al. *The American Journal of Pathology*, 145(2): 440–451, 1994, incorporated herein by reference of its entirety including any drawings.

DETAILED DESCRIPTION OF THE INVENTION

Preferred embodiments of the present invention are described in detail below. However, the following description of the preferred embodiments is not intended to limit in any way the scope of the present invention, which is defined in the appended claims.

The present invention provides isolated stealth viruses and related vaccines. Several methods for isolating such viruses are producing such vaccines are described herein.

The present invention also provides several culturing conditions that induce a cytopathic effect in a sample containing a stealth virus. These culturing conditions include using approximately 5%–10% fetal calf serum, refeeding the culture medium every 24 to 72 hours using viral enhancing medium and using preculture centrifugation. These conditions are important for inducing a cytopathic effect. For example, the failure to replace the culture medium every 24 to 72 hours often prevents detection of the cytopathic effect. Another example is provided by the fact that not all media are optimal to induce a cytopathic effect. Indeed, the use of a basal medium such as minimal essential medium with 2% fetal calf serum and weekly refeeding of the cultures as is commonly practiced in most clinical virology laboratories will not generally yield a cytopathic effect with primary isolates of a stealth virus. Thus, it can be seen that only a carefully selected specific set of culturing conditions are capable of inducing a cytopathic effect in a sample containing a stealth virus.

Utility

The isolated stealth viruses and related vaccines of the present invention have broad utility, particularly in relation to the diagnosis and treatment of stealth virus related disorders. Those skilled in the art will recognize that in many cases the methods for detecting stealth viruses described herein involve the isolation of stealth viruses and thus the utility of the methods of detecting are also relevant to the isolated viruses themselves.

The present invention provides methods for the detection of a stealth virus. A virus is an infective agent and the stealth virus is associated with disease. The disease may be chronic fatigue syndrome (CFS) or one of several other diseases. Therefore, my invention has broad application to any area in which it is important to detect a stealth virus. Such areas include medical, veterinary, and agricultural diagnostics and industrial and pharmaceutical biological quality control.

Many patients with a stealth viral infection have a stealth virus associated disease. Therefore, the detection of the presence of a stealth virus may allow one to confirm the diagnosis of a particular disease. Thus, those patients may avoid needless treatment, including psychiatric treatment for a functional or psychosomatic as opposed to organic illness. Indeed, it is useful to detect the stealth virus in order to develop a therapy or treatment for patients with a stealth viral associated disease. For example, in order to develop a vaccine or anti-viral therapeutic agent it is useful to first detect the virus.

In contrast, many patients without a stealth viral infection do not have a stealth virus associated disease.

Thus, the failure to detect a stealth virus may indicate a functional or chemical rather than an infectious illness. Therefore, those patients may seek proper treatment, such as psychiatric treatment, rather than pursuing treatment aimed at eliminating or reducing the effects of a stealth virus.

Since the stealth virus is associated with disease, it will often times be useful to detect the virus either in order to eliminate or avoid it. For example, in some circumstances a pure material or sample is desired and it would therefore be useful to detect a stealth virus in the material or sample.

It would be useful to know if a food or beverage contained a stealth virus. One could simply avoid consuming the food or beverage in that case as a matter of prudence in order to reduce the risk of contracting a stealth virus associated disease. Similarly, it would be useful to know if a sample of blood contained a stealth virus. One could then simply avoid that blood in order to reduce the risk of contracting a stealth virus associated disease. Many other potential sources of infection are identified herein. Thus, detecting the virus may allow individuals to avoid the virus and any diseases associated with the virus. In other words, the invention is useful for prevention of disease transmission by identifying potential sources of infection.

Stealth viruses may be isolated by tissue culture from a blood sample obtained from a subject with symptoms associated with the chronic fatigue syndrome or with various atypical neurological psychiatric, rheumatological, glandular or liver diseases. Viruses may also be isolated from blood of animals infected with a stealth virus. In addition to blood, virus may be recovered from other biological samples including surgical and fine needle aspiration tissue biopsies, post mortem organ biopsies, throat swabs and saliva, urine, cerebrospinal fluid (CSF), other body fluids, blood and blood products intended for transfusion or for in-vitro uses, vaccines, foods and from the environment.

In a preferred embodiment, stealth virus is isolated from heparinized blood using a mixture of buffy coat granulocytes and ficoll-hypaque separated lymphocytes. In a particular embodiment lymphocytes and granulocytes are obtained following a Ficoll-Hypaque density centrifugation of blood. Methods known in the art for viral isolation and propagation can be used. In a specific embodiment, isolation of stealth virus from blood and CSF is carried out as described herein.

VACCINE DEVELOPMENT

Once viral antigens are identified by their ability to react with antibody and/or to elicit an immune response is determined, the skilled artisan can proceed with a vaccine development program similar to those being pursued with other viruses. Animal models using the stealth viral isolates as challenge will assist in this development and in its application to humans. The isolated viruses, as well as synthetic peptides and recombinant DNA derived protein, can be used to monitor the development of humoral and cell-mediated immune responses in naturally infected and intentionally immunized individuals.

Preferably, a stealth virus vaccine will elicit a helper-T cell response, which in turn results in a stronger antibody and cellular immune response (see, generally, Ada, 1989, "Vaccines," in *Fundamental Immunology*, 2nd Edition, Paul (ed.), Raven Press, Ltd., New York, pp. 985–1032, incorporated herein by reference in its entirety).

Immunopotency of the stealth virus product can be determined by monitoring the immune response of test animals following immunization with the purified protein, synthetic peptide or protein or attenuated stealth virus. In cases where the stealth virus protein is expressed by an infectious recombinant virus, the recombinant virus itself can be used to immunize test animals. Test animals can include but are not limited to mice, rats, cats, dogs, rabbits, primates, and eventually human subjects. Methods of introduction of the immunogen can include oral, intradermal, intramuscular, intraperitoneal, intravenous, subcutaneous, intranasal or any other standard routes of immunizations. The immune response of the test subjects can be analyzed by one or more of the following four approaches: (a) the reactivity of the resultant immune serum to authentic viral antigens, as assayed by known techniques, e.g., enzyme linked immunoabsorbant assay (ELISA), immunoblots, radioimmunoprecipitations, etc. (See Section 5.3., supra); (b) the ability of the immune serum to neutralize viral infectivity in vitro; (c) stimulation of cell mediated immune response, including the production of cytokines; and (d) protection from stealth virus infection.

Many methods can be used to administer the vaccine formulations described herein to an animal or a human. These include, but are not limited to: oral, intradermal, intramuscular, intraperitoneal, intravenous, subcutaneous and intranasal routes. Since stealth virus transmission is likely to occur via the respiratory system, the secretary IgA antibodies produced by the mucosal associated lymphoid tissue can play a major role in protection against stealth virus infection by preventing the initial interaction of the pathogens with the mucosal surface, or by neutralizing the important epitopes of the pathogens that are involved in infection/ or spreading of the disease. Stimulation of mucosal immune responses, including production of secretary IgA antibodies, can be of major importance in conferring protection against transmission via lower and upper respiratory tract. When a live recombinant virus vaccine formulation is used, it may be administered via the natural route of infection of the parent wild-type virus which was used to make the recombinant virus in the vaccine formulation.

The proteins and polypeptides of the present invention that are related to neutralizing epitope(s) of the stealth virus are useful immunogens in a subunit vaccine to protect against stealth virus infection. Subunit vaccines comprise solely the relevant immunogenic material necessary to immunize a host. Vaccines prepared from genetically engineered immunogens of stealth virus proteins or fragments thereof, which are capable of eliciting a protective immune response, are particularly advantageous because there is no risk of infection to the recipients.

Thus, the stealth virus proteins and polypeptides can be purified from recombinant cells that express the neutralizing epitopes. Such recombinant cells include but are not limited to any of the previously described bacteria or yeast transformants, cultured insect cells infected with recombinant stealth virus protein(s) in baculoviruses or cultured mammal stealth virus express stealth virus protein epitopes.

The stealth virus proteins or polypeptides are adjusted to an appropriate concentration and can be formulated with any suitable vaccine and adjuvant. The polypeptides and proteins may generally be formulated at concentrations in the range of 0.1 mg to 100 mg per kg/host. Physiologically acceptable media may be used as carriers. These include, but are not limited to: sterile water, saline, phosphate buffered saline and the like. Suitable adjuvants include, but are not limited to: surface active substances, e.g., hexadecylamine, octadecylamine, actadecyl amino acid esters, lysolecithin, dimethyl-dioctadecylammonium bromide, N,N-dioctadecyl-NI-Nlbis(2-hydroxyethylpropane diamine), methoxyhexadecyglycerol, and pluronic polyols; polyamines, e.g., pyran, dextransulfate, poly IC, polyacrylic acid, carbopol; peptides, e.g., muramyl dipeptide, dimethylglycine, tuftsin; oil emulsions; and mineral gels, e.g., aluminum hydroxide, aluminum phosphate, etc. The immunogen may also be incorporated into liposomes or conjugated to polysaccharides and/or other polymers for use in a vaccine formulation.

In yet another embodiment of this mode of the invention, the related protein or polypeptide is a hapten, i.e., a molecule which is antigenic but that cannot independently elicit an immune response. A hapten comprises an epitope, as defined in Section 5.3., supra. In such case, the hapten may be covalently bound to a carrier or immunogenic molecule; for example, a large protein such as protein serum albumin will confer immunogenicity to the hapten coupled to it. The hapten-carrier may be formulated for use as a subunit vaccine.

In a specific embodiment, the polypeptides and proteins of the present invention may be used when linked to a soluble macromolecular carrier. Preferably, the carrier and the polypeptides and proteins of the present invention are in excess of five thousand daltons after linking. More preferably, the carrier is in excess of five kilodaltons. Preferably, the carrier is a polyamino acid, either natural or synthetic, which is immunogenic in animals, including humans. The manner of linking is conventional. Many such linking techniques are disclosed in U.S. Pat. No. 4,629,783 which is incorporated herein by reference. Many cross-linking agents that can be used are disclosed in 1986-87 Handbook And General Catalog, Pierce Chemical Company, (Rockford, Illinois) pages 311 to 340, which pages are incorporated herein by reference.

Another embodiment of the present invention provides either a live recombinant viral vaccine or an inactivated recombinant viral vaccine, which is used to protect against disease symptoms of stealth virus. To this end, recombinant viruses are prepared that express stealth virus protein related epitopes. Where the recombinant virus is infectious to the host to be immunized but does not cause disease, a live vaccine is preferred because multiplication in the host leads to a prolonged stimulus, therefore, conferring substantially long-lasting immunity. The infectious recombinant virus when introduced into a host can express the stealth virus related protein or polypeptide fragments from its chimeric genes and, thereby, elicit an immune response against stealth virus antigens. In cases where such an immune response is protective against subsequent stealth virus infection, the live recombinant virus, itself, can be used in a preventative vaccine against stealth virus infection. Production of such recombinant virus may involve both in vitro (e.g., tissue culture cells) and in vivo (e.g., natural host animal) systems. For instance, conventional methods for preparation and formulation of smallpox vaccine may be adapted for the formulation of live recombinant virus vaccine expressing stealth virus proteins or polypeptides. Multivalent live virus vaccines can be prepared from a single or a few infectious recombinant viruses that express epitopes of organisms that cause disease in addition to the epitopes of stealth virus. For example, a vaccinia virus can be engineered to contain coding sequences for other epitopes in addition to those of stealth virus. Such a recombinant virus itself can be used as the immunogen in a multivalent vaccine. Alternatively, a mixture of vaccinia or other viruses, each expressing a different gene encoding for an epitope of stealth virus and an epitope of another disease causing organism can be formulated in a multivalent vaccine.

In yet another embodiment, stealth virus particles or proteins isolated from tissue culture may be used to prepare a vaccine. These particles should be attenuated to prevent infectivity, e.g., by heating. Where stealth virus-associated toxin is found in the culture, this toxin should be purified away from the vaccine components. Purification of viral components for vaccine use may be accomplished by ultracentrifugation, solvent extraction, or other means known in the art.

In pursuing this goal, it is recognized that while the establishment of immunity prior to exposure to stealth virus infection may be beneficial in preventing disease transmission, the occurrence of a cellular immune response in an already infected individual or animal could have deleterious effects. The various assays described above could be employed to detect such deleterious immune responses and allow for the development and the monitoring of means to reestablish the desired lack of cell mediated immunity against the resident virus.

The present invention is also useful in a variety of other ways readily apparent to those skilled in the art.

EXAMPLES

This invention will be more fully understood with reference to the examples which follow. The following examples are intended to illustrate the invention, but not to limit its scope which is defined in the claims appended hereto. The following examples are presented to illustrate the advantages of the present invention and to assist one of ordinary skill in the art in making and using the same, but are not intended in any way to otherwise limit the scope of the disclosure or the protection granted by a letters patent hereon.

Examples of cloning and sequencing of isolated stealth viruses are described in international patent application, publication No. WO 92/20787, published Nov. 26, 1992.

Examples showing cytomegalovirus-related sequence in an atypical cytopathic virus repeatedly isolated from a patient with CFS is described in Martin et al., *American*

*Journal of Pathology*, 145 (2):440–451, 1994, incorporated herein by reference in its entirety, including any drawings.

Additional sequence data and comparisons provided in Appendix A attached hereto as part of the specification and incorporated herein by reference in its entirety, including any drawings, suggest the probable origin of the stealth virus from the prototype CFS patient as being African green monkey and indicate further vaccine development techniques.

Stealth viruses are molecularly heterogeneous and there are multiple potential sources of these viruses from among the various human and animal herpes viruses and possibly other viruses. Analysis of the sequence data of individual isolates can help identify its probable origin and lead to an understanding of the original source of the stealth virus isolate.

In the following examples, the detection of the cytopathic effect was recorded as follows. This minimal level of CPE has to be transferable to secondary cultures for the culture to be recorded as a true positive (+). A + (one plus) positive effect indicates the presence of multiple enlarged refractable cells forming small clumps with indistinct cell borders are clearly seen in the cultures. A ± (plus/minus) or equivocal effect refers to a minimal change in the culture in which the rounded cells are either not enlarged or non-refractile (possibly dead). Less than 4% of cultures from CFS patients have been recorded as equivocal, either because the CPE has been restricted to only a small region of the culture, or because it has failed to recur on secondary passage. These cultures have been excluded from analysis.

A ++ (two plus) strong positive response is recorded when vacuoles are clearly identified within enlarged, rounded, refractile cells and/or when multiple foci of cell clumping and/or destruction are apparent which are ringed by cells described as having a positive effect. A +++ (three plus) very strong positive effect refers to extensive ++ cellular changes throughout much of the culture and/or the appearance of large refractile vacuolated, foamy syncytial cell formation. Typical CPE's are shown in Patent Cooperation Treaty publication number WO 92/20787.

A benefit of using multiple indicator cell lines, is that the CPE appearances in the different cell lines sometime complement each other. For example, cell syncytia are usually best observed in monkey kidney cells. The smaller rounded retractile cells are usually best observed in the human fibroblasts. In positive cultures, the CPE is clearly observable in or transmissible to at least 2 cell lines. As with any viral induced CPE, it is important to confirm transmission to fresh cultures. In recipient cultures, the stealth virus induced CPE generally develops more rapidly than in the primary culture with at least the same level of intensity.

Although the appearances of the CPE share some features in common with those associated with cytomegalovirus (CMV) and herpes simplex virus (HSV) infection, stealth virus cultures can be readily distinguished from cultures harboring these viruses. The CPE from HSV is much more rapid, occurring in a matter of days. The destruction is greater with large masses of dead cells. The CPE from CMV tends to initially develop in smaller, looser clusters and evolves more slowly than observed with stealth viruses. The intracytoplasmic vacuolization and syncytia formation are far less prominent with CMV than with stealth viruses. The stealth virus infected cells give more the appearance of "foamy cells" than does CMV. Indeed, with some stealth viral cultures, there appears to be a marked accumulation of lipid-like material attaching itself to the wall of the culture tube. Human CMV does not infect monkey derived cells.

Example 1

Culture Of Stealth Viruses—7% FCS and Frequent Refeeding

Culture tubes containing human fibroblast (MRC-5), primary human foreskin fibroblast (MRHF) and rhesus monkey kidney (RMK) cells are each inoculated with a cellular mixture of the buffy coat granulocytes and ficoll-hypaque separated lymphocytes derived from approximately the equivalent of one milliliter (ml) of heparinized blood. Typically, 5 ml of blood collected into a "green top" heparinized tube, are layered onto 3 mls of a ficoll-hypaque lymphocyte separation medium. Following 20 minutes centrifugation at 1,500 rpm, the lymphocyte, which collect at the plasma:ficoll hypaque interface, and the "buffy coat", present on the top of the erythrocyte layer, are collected into approximately 1 ml. An effort is made to minimize the number of erythrocytes in collecting all of the visible buffy coat.

The cell mixture is washed once in 1 ml of 199 medium containing 7% FCS and resuspended into 1 ml. Aliquots of 0.2 ml of the cells are added to culture tubes containing 1 ml of 199 medium plus FCS. The tubes are placed in an incubator at 37° C. for 45–60 minutes. The are then rinsed to remove macroscopically visible erythrocytes and other non-adherent cells. Rinsing (washing) consists of emptying the fluid content of the culture tube by decanting or by aspiration; adding 2 mls of medium or phosphate buffer saline; rocking the tube for several seconds to suspend erythrocytes; decanting the tube again. This important step is performed 2–10 times or until there are no macroscopically visible erythrocytes.

Two mls of medium with 7% FCS, are added and the tubes returned to a 37° C. incubator. Cultures are maintained in the incubator at 37° C., with refeeding (replacement of old medium with medium) at 24, 48 and 72 hours. The tubes are examined microscopically after the 24 hour refeeding and, if residual erythrocytes are present, the tubes are rinsed in a manner similar to that performed at the 45–60 min. step. The tubes are refed three times each week by replacing the old medium with 2 mls of fresh medium. This procedure is designed to reduce the accumulation of a inhibitory/toxic component in the culture medium which tends to suppress viral growth. The tubes are examined three times per week for evidence of CPE (CPE). CPE is generally recognizable between 2–3 weeks after culturing.

A lack of regular refeeding of the cultures can result in a tendency for the CPE to abort and not to progress. This effect is not seen with CMV infected cultures. In unfed stealth virus cultures and even with regular refeeding, one can observe a toxic effect on many of the remaining cells. Culture cells appear to lose a degree of vitality and become duller in appearance compared to control cultures. The fibroblasts can assume somewhat of a pavement appearance, instead of the elongated shape. Some of these changes can be mimicked using 5 nM of the polyether marine toxin okadaic acid (Cohen et al., "Okadaic acid: A new probe for the study of cellular regulation" *Trends Biochem. Sci.*, 15:98–102 (1990). CMV positive cultures do not demonstrate the toxic activity such as that observed with stealth viruses.

Moreover, the detection of CPE from CMV is readily seen in cultures containing only minimal essential medium and 2% FCS even without regular refeeding of cultures. This is the routine medium used in most virology laboratories and can be contrasted with the more enriched medium 199 and 7% FCS that is used to culture stealth viruses. The more enriched medium and the higher concentration of FCS, help to neutralize the toxic, stealth virus growth inhibiting effects, which would otherwise occur in the cultures.

Although presumptive of stealth virus infection, the CPE appearance may require additional confirmation for a definitive conclusion of stealth virus infection.

Example 2

Viral Enhancing Medium (VEM)

In preparing viral enhancing medium a known positive CMV culture was passaged into a flask of MRC-5 cells and fed with X Vivo-15 medium. The cultures were observed for the development of CPE. The culture medium was changed at 1 week when approximately 50% of the cells showed signs of CPE, but before there was marked cellular destruction. This newly added medium was collected 48 hours later. It was centrifuged at 800 g for 20 minutes to remove cellular debris.

The medium was transferred to new tubes which were placed in a beaker containing water. The water was heated to boiling for 20 minutes. After cooling, the medium was filtered through a 0.45 micron Millipore filter. This material was diluted 30:70 into regular X Vivo-15 medium to constitute a "lot" of CMV derived VEM. Each lot of VEM is tested to confirm: i) that it does not contain any residual live CMV by adding the medium to MRC-5 cells; and ii) that it can promote the development of the CPE induced by the prototype stealth virus by comparing the growth of the stealth virus in RMK cells containing VEM with that of similarly inoculated cells containing X Vivo-15 medium without supplement.

VEM has been tested on ten additional stealth viral isolates and clearly enhanced the growth of all of them. Two of these isolates are known to share CMV related sequences with the prototype stealth virus. Another isolate (from patient G.P.) shares antigens with HHV-6, rather than CMV, and is considered an HHV-6 related stealth virus. The use of VEM also reduced the time for a discernible CPE using fresh blood from two newly cultured CFS patients. It enhances the intensity of the CPE and reduces the tendency for weekly positive cultures to revert to near normal appearance. VEM has also worked well in the cultures from the tissues of cats inoculated with the prototype stealth virus from patient D.W. allowing for clearly positive culture results. VEM obtained from HHV-6 (strain GS) infected fibroblasts was similarly tested for its ability to promote the growth of CMV and HHV-6 associated stealth viruses. It worked well with both viral types with a discernable advantage on the HHV-6 related stealth virus from patient G.P., compared to the CMV related stealth virus from patient D.W.

As a specific example, cultivation of a prototype stealth virus isolated from a CFS patient (initials D.W.) can be greatly enhanced by the addition to the culture of VEM comprising a 30% concentration of boiled, filtered supernatants from cytomegalovirus (CMV) infected cultures. This addition helps remedy a deficiency of viral growth enhancing components coded for by the immediate-early (I-E) and probably other CMV related genes which are not detectable in the stealth virus from this patient.

Example 3

Viral Enhancing Medium and Pre-Culture Centrifugation

Human fibroblast (MRC-5), rhesus monkey kidney (RMK) and rabbit kidney (RK) cell lines were obtained from BioWhittaker, Inc., Walkersville, Maryland. The tubes were placed in a 370 incubator. The next day, the Delbecco's modified Eagles medium containing 2% FCS is replaced by medium 199 plus 7% FCS. The tubes were used to provide indicator cells for stealth viral cultures within the next 7 days. To establish the viral cultures, the contents of a single test tube of each of the indicator cell lines to be used were scraped from the tubes and washed once in X Vivo-15 medium.

The cells were gently resuspended into approximately 0.5 ml of medium and transferred to 2 ml Eppendorf tubes. Prior to this step, ficoll-hypaque separated lymphocytes from either heparinized or citrate treated whole blood, were obtained by layering 5 mls of anti-coagulated blood onto 3 mls of ficoll-hypaque solution in 12 ml conical tubes. The tubes were centrifuged for 20 min at 800 g. The banded lymphocytes were aspirated and transferred to a fresh tube for washing in 10 mls of medium. The lymphocytes were resuspended in approximately 1 ml. Aliquots of 0.2 ml of the lymphocytes were added to each of the Eppendorf tubes containing the harvested fibroblast indicator cells with a final aliquot stored for future studies.

The lymphocyte-fibroblast cell mixture was centrifuged at high speed for 3 minutes. The tightly-packed cell pellet was gently resuspended and transferred back to the tube from which the fibroblasts were originally obtained. Two mls of VEM (X Vivo-15 medium supplemented with 30% CMV supernatant) were added and the tubes are placed in an incubator at 37° C. The tubes were refed with VEM at 48 and 72 hours and thereafter 3 times per week.

Control cultures in which either lymphocytes from other individuals are used, or the fibroblasts were processed but with the exception of no added lymphocytes, were fed in parallel with the test cultures. Note, in this revised protocol, buffy coat granulocytes are no longer routinely used since the contaminating erythrocytes tended to clump about the fibroblasts during the centrifugation step and were difficult to remove in subsequent washing of the cultures. Granulocytes may be an important source of virus in some patients. If this proves to be so, leucocyte rich plasma will be obtained by dextran precipitation or ammonium chloride lysis of the erythrocytes from anti-coagulated blood, or as an alternative, modifications of the ficoll-hypaque separation method can be used which will separate both lymphocytes and granulocytes away from the erythrocytes. For example by using PMN isolation medium from Robbins Scientific Corp., Sunnyvale Calif. CSF and tissue extracts can be used in place of the lymphocytes.

The cultures were observed for a CPE which characteristically consists of rounding and swelling of the cells, formation of cell clumps which tend to disperse, appearance of intracellular granules/vacuoles and an overall foamy cell appearance often with prominent accumulation of lipid-like material.

TABLE 3

Examples of the Enhanced Recovery and More Intense Development of CPE by a Stealth Virus from a CFS Patient Using Pre-Culture Centrifugation (PCC) and Viral Enhancing Medium (VEM).*

| Method of Culturing | Time to CPE** | Intensity of CPE |
|---|---|---|
| Patient 1 | | |
| Medium 199 + 7% FCS | 45 days | 1–2+ |
| PCC and VEM | 12 days | 3+ |
| Patient 2 | | |
| Medium 199 + 7% FCS | 28 days | 1–2+ |
| PCC and VEM | 16 days | 3+ |

*Medium X Vivo-15 containing 30% supplement of boiled filtered supernatant from a CMV culture also grown in medium X Vivo-15.

**Results are in RMK cells. Enhanced growth was also seen in MRC-5 cells.

Growth of Stealth Virus in Insect Cell Line

The *Spodoptera frugiperdo* derived ovarian cell line Sf9 that is used routinely for the propagation of recombinant insect baculovirus was obtained from PharMigen, San Diego. It was maintained at 27° C. in Grace's medium with 10% fetal calf serum. The stealth viruses from patients D.W., G.P., K.E. and B.B. were passaged into the insect cell line using 0.1 ml of cell-free supernatant from an infected MRC-5 human fibroblast culture. CPE was clearly seen within two days and progressed over the next several days.

The infected cultures showed enlarged foamy cell syncytia. Virus infectious for MRC-5 and for insect cell cultures was recoverable from the insect cell cultures to a dilution of $10^{-3}$ ml. Electron microscopic examination of the insect cultures infected with the virus from patient D.W. showed abundant herpes-like viral particles. In control studies, neither cytomegalovirus, human herpes virus 6, varicella zoster virus or Epstein-Barr virus induced CPE in the insect cell line; nor was infectious virus recoverable from these cultures.

Example 5
CLONING AND SEQUENCING OF DNA IN STEALTH VIRUS ISOLATED FROM CFS PATIENT D.W.

5.1 MATERIALS AND METHODS

PCR is performed on tissue culture cells as follows: Cells from a single culture test tube are scraped into PBS, washed once and digested with 100 ug proteinase K. The subsequent procedures are identical to those used for proteinase K digested whole blood. Labeling of PCR products was performed using the random primer method described by Feinberg A. P. and Vogelstein B.; A technique for radiolabeling DNA restriction endonuclease fragment to high specific activity. Anal Biochem. 137: 266–269, 1984; using reagents from U.S. Biochemical Cleveland, Ohio, to a specific activity of approximately 109 dpm/ug.) Coning of PCr products is achieved as follows: The PCR products are blunt-ended, phosphorylated and cloned as follows: Following completion of the PCR, 2 units of Klenow enzyme and 1 uM of each DNTP are added to the reaction mixture. After 30 minutes incubation at 14° C., the DNA is extracted using 100 uL of phenol and of chloroform. The DNA is precipitated using ethanol in the presence of KOAC and gylcogen, washed once in ethanol and dried. The 51 end is phosphorylated using T4 kinase and ATP. Following a 37° C. incubation for 30 min., the kinase is inactivated by heating the mixture at 65° C. for 10 min. The reaction products are run in 0.8% low melting point agarose and the band of interest excised. A T4 ligase reaction is performed using purified pbluescript vector, previously cut with EcoRV and treated with calf intestinal phosphatase. The ligation reaction is allowed to proceed during an overnight incubation at 14° C. The enzyme is inactivated by heat (65° C. for 10 min.). Transformation into XL-1 competent cells is achieved by a 40 min. incubation on ice followed by a heat shock at 42° C. for 90 sec. The bacteria are plated on LB agar containing ampicillin, IPTG and X-gal. Colorless colonies are screened for an insert using the PCR product as probed and confirmed using the bacteria as template in the PCR. Sequencing of PCR products is performed according to the dideoxy/deoxy nucleotide termination method of Sanger F. Milklen S and Coulson AR. 1977. Proc. Natl. Acad. Sci. USA 74; 5463–5467.

5.2 RESULTS

PCR assays, using the HTLV tax gene primers SK43' and SK44", were performed on virus infected MRC-5 and MRHF cultures derived from CFS patient D.W. The HTLV primers consistently yielded an unexpectedly large band when examined by ethidium bromide stained agarose electrophoresis. The band had an apparent size of 1.5 kbp. The 1.5 kbp band was clearly distinct from several smaller products generated in the same PCR and from the 158 bp product obtained using the tax primers on HTLV-I infected cultures (FIG. 4). The individual HTLV tax primers SK43' and SK44" were tested in PCR assays on viral infected cultures. As has been noted in other PCR assays using single primers (Wang WP, Myers RL Chiu IM. Single primer-mediated polymerase chain reaction: application in cloning of two different 51-untranslated sequences of acidic fibroblast growth factor MRNA. DNA Cell Biol. 10:771–7, 1991.), the SK44" primer used as a single primer was as effective in generating the 1.5 kbp band as was the combination of the two primers. Similarly, the SK43' primer set used alone could generate a discrete PCR product from the stealth virus infected culture from patient D.W. (see infra).

The 1.5 kbp PCR product(s) generated from the virus infected culture was excised from the agarose gel, labeled with alpha-32P DCTP and used as a probe. It hybridized with extracts from infected cultures from the patient and with extracts from a positive culture from a patient (B.H.) who is described infra. It did not hybridize with material extracted from uninfected MRC-5 cells or cells infected with CMV, HSV, HHV-6, HTLV-I or HTLV-II. As expected, PCR generated products using the tax primers on the infected cultures hybridized strongly to the labeled probe.

Cloning and sequencing of individual recombinant plasmids showed that there were two distinct PCR products generated in virus infected cultures using the SK44" tax gene reactive primer. One product cloned into plasmid number 15-5-2 contains 1484 bases while the other product, cloned into plasmid number 15-5-4, contains 1539 bases. The sequences of the plasmid inserts are shown in Tables 1 and 2. Both inserts are flanked by the EcoRV cloning site (GAT/ATC) and the SK44" primer used in the PCR. Computer assisted analysis (FastA Program available from Genetic Computer Group, Wisconsin) showed no apparent homology between the sequence in plasmid 15-5-2 with any viral or nonviral sequence contained in the entire GenBank data base (updated as of 12/91). Analysis of the sequence of plasmid 15-5-4, however, showed highly significant, partial, homology with the AD169 strain of human cytomegalovirus (GenBank Accession number: X17403). FastA analysis revealed a 58% identity over a 1,201 bp overlap. The overlapping regions extended from nucleotide 140 to 1,311 of the insert and nucleotide 44,705 to 45,891 of the CMV genome. This region of the CMV genome is contained within the transcripts of both the UL33 and UL34 genes and is part of the protein coding sequence of the UL34 gene which extends from nucleotide 44,500 to 46,011 (Chee MS, Bankier AT, Beck AT, et al. Analysis of the protein coding content of the sequence of human cytomegalovirus strain AD169. 1990 Curr. Topics Micro. Immunol. 154: 126–169. Welch A. R., McGregor L. M., Gibson W. Cytomegalovirus homologs of cellular G protein-coupled receptor genes are transcribed. 1991. J Virol 65: 3915–3918). No significant sequence homologies were identified for the sequence beyond the region of overlap with the UL34 coding gene. In particular, the flanking regions adjacent to where the primer had been incorporated bore no significant relationship to the sequence of HTLV.

The sequences of the two plasmids were used to design sets of virus specific primers and detecting probe for use in the PCR. The regions used are indicated in Tables 1 and 2. These primers gave no detectable products when the PCR was performed on blood samples from normal individuals or on uninfected cultures or cultures infected with CMV, HSV, HTLV-I or HTLV-II. Strongly positive PCR responses, shown by a well defined band of the expected size on agarose electrophoresis and by Southern blot hybridization with labeled probe, occurred when the PCR was performed on viral cultures derived from the patient D.W. even over a 3 log dilution. All six independently derived cultures from patient D.W. gave strong positive PCR. Moreover, frozen blood samples collected from patient D.W. over an 18 month period tested positive. FIG. 6 shows the banding pattern of the PCR products obtained using seven stored blood samples. These data establish that the virus was derived from patient D.W.

The SK43' primer used by itself was also able to generate a PCR product of 660 bp. The sequence of this product, which shows no significant homology with known viruses is shown in Table 3.

It is possible to screen multiple primer sets for such cross-reactivity. As a further example, a positive PCR can be obtained from the stealth viral culture of patient D.W. using a primer that corresponds to a region of the Epstein-Barr virus. This product has been isolated, cloned and sequenced. Its sequence is shown in Table 4.

5.3 CONCLUSION

The available sequence data confirm that I have isolated a novel virus with at least some homology with a herpesvirus. To date, I have not identified known retroviral sequences in the virus. Using the available virus-specific plasmids, I am currently proceeding to isolate additional regions of the viral genome for sequencing. The example shows the use of PCR primers, which fortuitously bound to the viral template DNA, to derive clones and sequence data from stealth virus infected cultures. The same approach can be taken in using paraffin-embedded tissue sections or other non-viable samples containing stealth viral genomes.

TABLE 1

Sequence of PCR amplified product obtained from
virally infected cells and cloned into plasmid 15-5-2.

5'-GATGAGCTGACAACGCGTCCATCGGAACATGACAGCACGGAAAC
TACCCCTATCTTGTCCGCCTCGCACAAACCCAGCACGAACACACCCCCGG
CTGTCTCACCTAAGCCAACCATCTCCAACGGCACCAAAAAGCCCATTGTT
CCACCAAAACCTAAACCGAAGCCAAAGCCGACGATGCTCCAGTTCCCCGC
ACCCAAAAGCGCCAGACCACGCCCAAGAACACTCAAAGTCCCAAAGTGTT
TACTTTTAACGAGCGTGACATAAGAAAGCACAAAGAAGAGATGGGCGCGG
AGGCCACGAAACCTAGAATCATCCATCACACAGAAGACAGAACCACCGTT
GACAGCGTCCTAACGCCGCTACTGCCACCTCCACCGCCAGCTCCCCGACG
GTATCAACATCGCGGGTGCCAGTGATGATTCCCTGGGACAACACGCAATC
TCCCGCGAAGATGAGTCCCTGGAAAGACACTTGCGAATCCCTGCCCACGG
AGCTGGACCCTTGGGAGTTTAGGCCCCGCCGTGGTTGTAGTAAAAAGAAC
TTGGACTGTCAATCAAACTGCAGATTGTATAGCTATTTAAACTTTATTTC
TGTATATATGTGTAAATAATAAATTTATTCCTCGTATCACACATCTGCAT
CCTGGTCATTCACATCTAGTATTCGCAGCGCAATTCGGGGCCCGGGAGGG
TGCATCATGGCGTCCGGGGCTATCTCTTCCATGATTAAGATAATCTCATC
TCCCAACGGAGGCCTGTTTTCCTGGTCCTCAGCCTGTATTTCCATAGCGA
TCTCTACCACCTCAGCCACCTCGGGAGGAAACTGCAACGGCTGGATCTGC
AGTTGAAGCTGCTGTCGTTGCAGATAGTTCTGAAACAGTCTCCGCCGAGC
CCGAGGAGCATACATGCCTAGAGGGCGATGGGCAGGTTGGTTTAAACGAT
AAAACGAAGCCCGGATAGAAGGCATGAGACCGCGGACGGCCTCTGATAAG
AGGGGATCGGTGCTGCCTCCCATAGTGCCAGTAAGATTCTGGGAGAGTAG
ACATTCCTAAATACTAGCCTGGATCTGACGTCAACACTATGATTCACGCC
CAATTCCACCCACAAAGCCCGTTAGAATACCAGACAACGTCCCCGTTAGT
GATGCCACCCACACAAGATATTTAATGATAACAGAGTTTCAGACCGCCTT
TGTTGAATCGATTCCAATACCGGCATCATGAGGAATCTACAGCTGATCGC
AACTTTGCTAGTTATCGGTTTGGTGGCAGTTCATGCCATCCCCAGGTTGG
AATATGTAACCATATATATCGCGCCCTAGTTATAACCATATTTGACCTGA
AATACTAATGATTCTTTCCTCTCACATGTGCAGGAGAACCACAGATGATA
ATAAAAAGACAACAAACTCAGACTTAAGCAACCAGACCGACGGTGGCGCT
GGCTTCGGCAGCACATACGATGGACGCGTTGTCAGCTCATC-3'SEQ ID NO: 1

The sequence is shown as read from the T3 sequencing primer of the plasmid. SK44" primer sequences are indicated by bold type. The underlined segments show the positions of the primers and the detecting probe which were synthesized to enable plasmid-specific PCR amplification. A second plasmid (15-5-1) gave essentially identical results, as did sequencing of a cloned Pst I digest of the PCR products.

TABLE 2

Sequence of PCR amplified product obtained from
virally infected cells and cloned into plasmid 15-5-4 and
comparison with the sequence of CMV.

10
5'-GATGAGCTGACAACGCGTCCATCGGCCAGATACATAAGTTTACACTCACTGGTACTTGTC
5'-GTGGCGCCCCGGCTTCATTATAACGCCACGTCGGAGCCCCTGCGCGCCACAACGCCGTCC
44570

70
ACTCACTTGATCACTTTGCTGCGGACGTGACGGCCAATCGTTTCGGGCAGGAGTGGCCAA
GGCGCAACTTCTGTCTCGGCACGGTACGATAAAAACAACGTCCCCCGTCGACGTTGTTTT
44630

TABLE 2-continued

Sequence of PCR amplified product obtained from
virally infected cells and cloned into plasmid 15-5-4 and
comparison with the sequence of CMV.

```
         130
ACGGCATTATAACGAAACGCCGACCGGGGCCACACGCCAC-TTGGAAACGCCGCCGTTAG
CTCCGAGCGGTGATCGTTCCCGTCCCTCTCCTCCCTCCGCGGCCCCCACGGCGGCGGCCT
44690

190
TCCTTTTTTCAACGGTACGATATCGG--CAATCCCCAT-GAC--TATGAACATAATTATA
GCTCGCACGGACCTATACTATTACCGCCCGACCGCCGTCGTCGTCATGAACTTCATCATC
44750

240
ACCACCCGCGAATTCTCCAATGACGAATCCGTCACAGAGAG-CACGGAACCGCAAGACAA
ACCACCCGAGACTTCTTCAACGACGATTCAGTC-CTGCGAGCCGCCGAGATGCGTGACAA
44810

300
CGTTGCCAATAACCTTTCTAAAGCTTACCGAGGTACGATTCGCGCGGAAGGTAAGAAGAA
CGTGGCAGGCTCGATTTCCAAAGCTTACCGAGGTACGATTCGCGCGGAAGGTAAGAAGAA
44870

360
ACTGCTTATTCGCAACCTG--CCTGCC-ACTTTCGGCTGCACTCGCCGCAACAGTAATTT
GCTGCTGCTGAAGCACTTGCCCGTGCCGCCCGGCGGCTGCTCGCGCCGCAACAGCAACCT
44930

420
ATTTATATTTTATAACGACCGGGACTATCGAAAGTTCCATCAAGGCATCATACAGTTAAA
CTTCGTTTTCTGCACCGAGCGCGACTACCGCAAGTTCCACCAGGGCATCGCACAGCTCAA
44990

480
ACGAACTCGCACGCGAGTTGATTCATCACAGATCGTGAACGTTACAAAAAAATATAAAGTC
GCGCGCGCCGGCCGAACTGGACCGCCACGAGATCCAGCAAGTCACGGCCAGTATCCGCTG
45050

540
TCGACTGCAACCGCACAACT-CAAGACCCGCCGCTAGCCGGCGGGC-AGATCCAAACCACC
CCGCCTGCAGCC-CAGTCTCCGCGAGCCGCC-CACGCCGGCCGACGAGCTGCAGACGGCT
45110

600
ATCTCGCACGTCTGCACTCTGTTCAATCACCTCGTGTTCACGGCTCAGCTCCGTCATTAT
GTGTCGCGCGTGTGCGCGCTCTTGAACCAGCTGGTTTTCACGGCCCAGCTGCGCCACTAC
45170

660
TGCGAAACTCACGAACAAGTTGTCTTGTACGCAAGGGACGAGCTCACCAAACGTTGCGGA
TGCAGACACCAGGACAAGGTGGTGAGCTACGCGCGCGACGAGCTGACTAAACGCTGCGGC
45230

720
GACAAGTCGGCGCTCGGGACTCACACTCACCGACTCATTCCGCTCTTGGATCACGACAAC
GAAAAATCGGCGCTGGGCGTGGAAGTGCATCAACTGGTAGCCCTGCTGCCACACGAGCGC
45290

780
CATCGCGAACTGTGCAATGTGCTGGTCGGCCTGCTACACCAAACACCCCACATCTGGGCC
CACCGCGAACTGTGCCACGTCCTCATCGGCTTGTTGCACCAGACGCCGCACATGTGGGCG
45350

840
CGTTCCATCCGTCTTATCGGCCGATTAAGAAACTATCTACAACAGAAGTTTCTCAATATC
CGCTCCATCCGTCTCATCGGACACCTGCGCCACTACCTCCAGAACAGCTTCCTACACCTG
45410

900
TTGGTGGATAGCGGACTCCAGATCGATAGTCTTTTTGAGGCTTGTTACCACAGCGAACGG
TTCATCAACTCAGGTTTGGATATCGCACAAGTTTTCGACGGCTGTTACCACAGCGAGGCC
45470

960
TACCGCTTGCTGTTCCAGATCGAAAAAACGAACTCCACCCCTAGCTCTCTAGCCTGTGCA
TACCGCATGCTCTTCCAGATCGGTCATACGGACTCGGTGTCGGCGGCCCTGGAACTCTCA
45530

1020
AGCACCGTTTTACCTGTCGGTGAAAACGAAACTGAAGGCACACCTGTCCCGCCGTGTATT
```

TABLE 2-continued

Sequence of PCR amplified product obtained from
virally infected cells and cloned into plasmid 15-5-4 and
comparison with the sequence of CMV.

CACGGCG---CGGCGGCCGGGCCGCCCGAGGCCG-ATGAAAACAACGACGAGGGAGAGGA
45590

1080
TAATGAAATAATAAAATGGTTCTCATGAATAAGACGGTCTTAGTTTCGTTTTTGAA--AG
GGACG--ACGACGAGCTCCGTCACAGCGACCCGGCGCCGCTTCACGAGTCCAAGAAGCCC
45650

1130
GACAAGTATGAGTGTCCCCCCACAC-ATCCCCGCCT---TGGCCGTGGACTCGAG----C
CGCAACGCCCGTCGTCCCCGCACACGCGTCCCGCCTCACGAGCAAAAGCCCGAAGAAAAC
45710

1190
CTGAACTTTCGTGCGCACCTGTTT----TCTG-ACCACAACCGACACTTTCTAGTCGATT
GACCAGCAAGAAGACGACCTGTTTCCCTCCTGCAAGGCAACCGCACCATTCCTG-CG-CC
45770

1240
TAGTAACCCAAAGCTGCAGCGGCTATGTGGGACTG--TGTAACGCCGGAATTCCCATCCC
CAGAACCCTCCGTCTCCAACGACGACG-GCAACGGCGGCGAACGCTGCGACACGC-TAGC
45820

1300
CACCTATGTACTGGAAACGCTAATTGACTTTCAGGTTCCAACCACATACACGAAAATTAA
GACCGCCCTGC-GGCATCGCGCCGACGAAGAAGACGGACCTCTAGCCAGCCAGACCGCTG
45880

1360
GCCCATTGCCGTAAAAGTGCTAAAAATCTGTATTCTGGCTAACTACCTAAAAAACAGTAA
TGCGGGTCGCCGCGACCCCCTCACCTTCAGTCACCCCAGCCCTTACCCCCGTCACGTCCC
45940

1420
AGAATTATGGATTGATTTCAAAGCTAACCTAGACGAGATTAATTCTGGTGCAAATAAGCA
CCATAACCCCGTTGTGTATTTAACGTCACTGGAGGACAATAAAGCGTTGATTTCTCAACT
46000

1480
AAGACTGTACAGAGGCTTTTACAAACTATGTCGTGATAAAAACTCGATGCACGCGTTGTC
TCCGCTCTGGTTTTGGTTTCGTTTTCAAAGGGAGCCCCATCATGGCCCAACGATCGCGAG
46060

AGCTCATC-3
CCCCATCC-3

The upper row in each pair of sequence is that of plasmid 15-4-4 read from the T7 primer. The lower row in each pair is that of human CMV (Genbank accession number X17403). The nucleotide numbers are shown. The SK4411 primer sequences incorporated into the plasmid are indicated by bold type. The underlined segments show the positions of the primers and the detecting probe which were synthesized to enable plasmid-specific PCR amplification. A second plasmid (15-6-1) gave essentially identical results, as did sequencing of a cloned Xho I digest of the PCR products. Note The sequences identified in this viral isolate are present in some but not in the majority of other cultured stealth viral isolates.

TABLE 3

Sequence of PCR amplified product obtained
using SK43' primer on viral culture from patient D.W.

5-
GGAATTCGATCGGATACCCCGTCTACGTGTATTAATATTACATAAAATAGGCTTTTTTTT
AAAAAAAAGAAAAGACATTTTTCACTAATGGTGTCATATCATTATAATAAACCTTGTTTT
CATCAGGAAGGTATAAAAACAAATTCATATGCACTAAATAATATAGATTCAAAACAAATA
AGGCAAAAATCAATGGCAACAGAATAAGCATATATATAAACATGGTGAAAAATTACATAT
AAACACCAAGAATGTGGAAGATTTAGCTGTGATTAGCAAATTTTGCCTAATGGATATATA
TGTATAAACTTGTCCCAATATCTACAGAGTACTCATTCCTATCAAACACAAATAAAACAG
TTCTTAAAAATTCAGTACATATTGTGTCAATTTTAAAAATAAGCTTCAAAGTTTTGATAC
TATAATTTAGAAACTATCTCGAGGGAAATAATATAAATAGTTTAAATAAAAGTGAGGTGA
AACTAATGTATATTTAGATGAAGCAGTATAGTTTTAAATTTACATATTATAAAAGAAGAA
TATTAATGAACTAAACATACATCCTAAGAAGTTAGAAATAGAATAGCAAAATAAACTCAA
AGAAAGCATAAAAAAAGAAACTGGTGGAACGGGAAACACACGTAGACGGGGTATCCGATC
AAGCTT-3

23
EXAMPLE

EVIDENCE BASED ON VIRAL CULTURE OF STEALTH VIRUS INFECTION IN BLOOD OF ADDITIONAL CFS PATIENTS

A large number of patients diagnosed with CFS have been tested for stealth virus infection using the culture method described in detail in this Section. Table 4. Sequence for PCR amplified product derived from stealth virus from patient D.W. The product was amplified using a single EBV reactive primer, cloned into pbluescript and sequenced as describe above. The plasmid is designated number 7.

24
6.2 RESULTS

The SK43'and SK44" primers generated PCR products from the various stealth viral cultures. When examined on agarose gels, however, only the culture from patient B.H. gave a banding pattern similar to that seen with the viral culture from patient D.W. This finding was consistent with the previously observed cross-hybridization seen with labeled PCR products between these two cultures. PCR products could also be generated on the culture from patient B.H., using the primers based on the sequences of the cloned plasmids obtained from the virus infecting patient D.W. In spite of this molecular similarity, at least in the regions so far examined, the fine details of the CPE associated with the

TABLE 4

Sequence of PCR amplified product derived from stealth virus from patient D.W. The product was amplified using a single EBV reactive primer, cloned into pbluescript and sequenced as described above. The plasmid is designated number 7.

5'-
TATCGATAAGCTTGATTTCGCGTTGCTAGGCCACCACTAATGCATGATTTTTCTTTCAAA
TATACCAACACATAAAATACGATAGTAGCCACACAGCAACAAATAATGAAATCATGTACC
GAAGAGGTTCAGGTCCAGTTAAAAATAGAAAAGTATGAATAAAGTGCCTCCATCCCTTAG
GGAATTCGATTTCGCGTTGCTAGGCCACCGCTTTGTTTTTTGCAATCTCCTACGGTAAAA
GTAATACAAGGGAATGGAGAGCCGCCGCTCGATACGCACTAGCACTGCAATTGGAAATTC
GATCCAAAGAAGAACCGTGGACGCCACTTGAACCTCGCATATTTCAGCGCGTGTATTTGG
AACACGACACGACTTCCCAACTCAACAATGATCAACTACATGTCAGCGGAACTGTGATTG
GAAATTTTACAAATACAGCTTGGATGCATGTTAGTCTGAGTTATCCTAAGTTCAAGGAAA
TGTTCGTCATGTCTACCAACCCAGACATCACAGTGA. A-31

6.1 EXAMPLE EVIDENCE OF MOLECULAR HETEROGENEITY AMONG DIFFERENT ISOLATES OF STEALTH VIRUSES

Partial sequencing of the stealth virus from patient D.W. has been completed and virus specific primers made. The question was raised whether these viral sequences were detectable in other stealth viral isolates. The viral cultures isolated from patients B.H., J.T., T.R., G.P. and two CFS patients (N.R. and L.B.) were analyzed using, PCR assays. The primers included the HTLV tax gene primers (SK43' and SK44" and the specific primers based on the sequences in plasmids 15-5-2 and 15-5-4 containing PCR products amplified from cultures from patient D.W.

6.1 MATERIALS AND METHODS

PCR assays and the cloning and the sequencing of PCR products was as described supra.

viruses from patients D.W. and B.H. show clear differences. For example, the size of the cell syncytia is larger in cultures from patient D.W.

A PCR product of about 600 bp which was generated using the SK43' and SK44" primer set on the culture of the patient L.B. was cloned and sequenced (Clone 18). The PCR product contained both the SK43' and the SK44" primer sequences. This: is in contrast to the situation with the cloned PCR products generated from the cultures from patient D.W., which contain either the SK43' or the SK44" primer, but not both. The sequence of the product derived from the L.B. culture is shown in Table. It shows no relationship to known viruses or to the previously sequenced PCR products from patient D.W. In spite of this, the electron microscopic appearance is quite similar to that of the virus from both patients D.W. and B.H.

TABLE 5

Sequence of PCR Product Generated Using the SK43' and SK44" Primers Stealth Virus Culture from Patient L.B.

AAGCTTGATCGGATACCCCGTCTACGTGTAACACCTGGAAAGTTAATGTT
CAGTGAAGCGCCCCAATGTCGCTGAATCCACCCAGCTCCTCACCTGCAAG
TTGGCCAACATGATGTGTCAAGTTGGGGACATGAATGCTTGTCCCACCTG
CCCTGGGAGAAAAGATCATAGAAGTGAAATGACCTTGTAAACAGCAAAGT
CCTGTGCAAATATAATGGTCCTTGTTGAGTCTTTTCCACATTCATAATCG
ATGTTTGTCTGACGCTGACCCCTGCTCCAGAACCACCCCCCCCACTCCCC
GGTCTGCTGTCGGGGAGCGCCAGGACACACTTGGCTCTTGGGCAGTTTTA
AGTAGGTTTAACGTTCTCACACTGATAGAAGTGGTGTACTTTAAAGATGA
ATTAAAATGAATACTTTATTAGTAACTCAGCTGTGCTTACTGCTAGATTC
CTTAAAATAATGCCCCTGCCTTTCCCACAATGACAGGGCTTGAATTTCTT
TTTTTGCGAAGTGTGGTGGTGAGTCACAATCATTTCCGATGGACGCGTTG
TCAGCTCATCGAATTCC SEQ ID NO: 6

6.3 CONCLUSION

These findings establish that various stealth viruses may differ in their genetic composition. In spite of this difference, the viruses show common characteristics when cultured in fibroblasts. A homologous genetic region responsible for the common biological property, such as the induction of foamy cells in vitro, is anticipated to be found with additional sequencing. An advantage of sequence heterogeneity among isolates is that it can be used to trace disease transmission.

Deposit Of Microorganisms

The stealth virus isolated from patient D.W. (virus-X infected MRC-5 cells) was deposited with the American Type Culture Collection (ATCC)—12301 Parklawn Drive, Rockville, Md. 20852, under the provisions of the Budapest Treaty on the International Recognition of the Deposit of Microorganisms for the Purposes of Patent Procedures on 9-17-91, and were assigned accession no. VR-2343.

The present invention is not to be limited in scope by the microorganisms deposited or the specific embodiments described herein since such embodiments are intended as but single illustrations of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entirety. In particular Martin, et al. *The American Journal of Pathology*, 145(2): 440–451, 1994 and Appendix A attached hereto as part of the specification are both incorporated herein by reference in their entirety, including any drawings.

What is claimed is:

1. An isolated, purified or enriched stealth virus contained in the MRC-5 cell line, ATCC accession number VR2343.

* * * * *

SEQUENCE LISTING ( 1 ) GENERAL INFORMATION:

( i i i ) NUMBER OF SEQUENCES: 104

( 2 ) INFORMATION FOR SEQ ID NO:1:

( i ) SEQUENCE CHARACTERISTICS:
( A ) LENGTH: 1485 base pairs
( B ) TYPE: nucleic acid
( C ) STRANDEDNESS: single
( D ) TOPOLOGY: linear ( x i ) SEQUENCE DESCRIPTION: SEQ ID NO:1:

```
GATGAGCTGA  CAACGCGTCC  ATCGGAACAT  GACAGCACGG  AAACTACCCC  TATCTTGTCC        60

GCCTCGCACA  AACCCAGCAC  GAACACACCC  CCGGCTGTCT  CACCTAAGCC  AACCATCTCC       120

AACGGCACCA  AAAAGCCCAT  TGTTCCACCA  AAACCTAAAC  CGAAGCCAAA  GCCGACGATG       180

CTCCAGTTCC  CCGCACCCAA  AAGCGCCAGA  CCACGCCCAA  GAACACTCAA  AGTCCCAAAG       240

TGTTTACTTT  TAACGAGCGT  GACATAAGAA  AGCACAAAGA  AGAGATGGGC  GCGGAGGCCA       300

CGAAACCTAG  AATCATCCAT  CACACAGAAG  ACAGAACCAC  CGTTGACAGC  GTCCTAACGC       360

CGCTACTGCC  ACCTCCACCG  CCAGCTCCCC  GACGGTATCA  ACATCGCGGG  TGCCAGTGAT       420

GATTCCCTGG  GACAACACGC  AATCTCCCGC  GAAGATGAGT  CCCTGGAAAG  ACACTTGCGA       480

ATCCCTGCCC  ACGGAGCTGG  ACCCTTGGGA  GTTAGGCCC  CGCCGTGGTT  GTAGTAAAAA       540

GAACTTGGAC  TGTCAATCAA  ACTGCAGATT  GTATAGCTAT  TTAAACTTTA  TTTCTGTATA       600

TATGTGTAAA  TAATAAATTT  ATTCCTCGTA  TCACACATCT  GCATCCTGGT  CATTCACATC       660

TAGTATTCGC  AGCGCAATTC  GGGGCCCGGG  AGGGTGCATC  ATGGCGTCCG  GGGCTATCTC       720

TTCCATGATT  AAGATAATCT  CATCTCCCAA  CGGAGGCCTG  TTTTCCTGGT  CCTCAGCCTG       780

TATTTCCATA  GCGATCTCTA  CCACCTCAGC  CACCTCGGGA  GGAAACTGCA  ACGGCTGGAT       840

CTGCAGTTGA  AGCTGCTGTC  GTTGCAGATA  GTTCTGAAAC  AGTCTCCGCC  GAGCCCGAGG       900

AGCATACATG  CCTAGAGGGC  GATGGGCAGG  TTGGTTTAAA  CGATAAAACG  AAGCCCGGAT       960

AGAAGGCATG  AGACCGCGGA  CGGCCTCTGA  TAAGAGGGGA  TCGGTGCTGC  CTCCCATAGT      1020

GCCAGTAAGA  TTCTGGGAGA  GTAGACATTC  CTAAATACTA  GCCTGGATCT  GACGTCAACA      1080

CTATGATTCA  CGCCCAATTC  CACCCACAAA  GCCCGTTAGA  ATACCAGACA  ACGTCCCCGT      1140

TAGTGATGCC  ACCCACACAA  GATATTTAAT  GATAACAGAG  TTTCAGACCG  CCTTTGTTGA      1200
```

| ATCGATTCCA | ATACCGGCAT | CATGAGGAAT | CTACAGCTGA | TCGCAACTTT | GCTAGTTATC | 1260 |
| GGTTTGGTGG | CAGTTCATGC | CATCCCCAGG | TTGGAATATG | TAACCATATA | TATCGCGCCC | 1320 |
| TAGTTATAAC | CATATTTGAC | CTGAAATACT | AATGATTCTT | TCCTCTCACA | TGTGCAGGAG | 1380 |
| AACCACAGAT | GATAATAAAA | AGACAACAAA | CTCAGACTTA | AGCAACCAGA | CCGACGGTGG | 1440 |
| CGCTGGCTTC | GGCAGCACAT | ACGATGGACG | CGTTGTCAGC | TCATC | | 1485 |

( 2 ) INFORMATION FOR SEQ ID NO:2:

( i ) SEQUENCE CHARACTERISTICS:
        ( A ) LENGTH: 1540 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

| GATGAGCTGA | CAACGCGTCC | ATCGGCCAGA | TACATAAGTT | TACACTCACT | GGTACTTGTC | 60 |
| ACTCACTTGA | TCACTTTGCT | GCGGACGTGA | CGGCCAATCG | TTTCGGGCAG | GAGTGGCCAA | 120 |
| ACGGCATTAT | AACGAAACGC | CGACCGGGGC | CACACGCCAC | TTGGAAACGC | CGCCGTTAGT | 180 |
| CCTTTTTTCA | ACGGTACGAT | ATCGGCAATC | CCCATGACTA | TGAACATAAT | TATAACCACC | 240 |
| CGCGAATTCT | CCAATGACGA | ATCCGTCACA | GAGAGCACGG | AACCGCAAGA | CAACGTTGCC | 300 |
| AATAACCTTT | CTAAAGCTTA | CCGAGGTACG | ATTCGCGCGG | AAGGTAAGAA | GAAACTGCTT | 360 |
| ATTCGCAACC | TGCCTGCCAC | TTTCGGCTGC | ACTCGCCGCA | ACAGTAATTT | ATTTATATTT | 420 |
| TATAACGACC | GGGACTATCG | AAAGTTCCAT | CAAGGCATCA | TACAGTTAAA | ACGAACTCGC | 480 |
| ACGCGAGTTG | ATTCATCACA | GATCGTGAAC | GTTACAAAAA | ATATAAAGTC | TCGACTGCAA | 540 |
| CCGCACAACT | CAAGACCCGC | CGCTAGCCGG | CGGGCAGATC | CAAACCACCA | TCTCGCACGT | 600 |
| CTGCACTCTG | TTCAATCACC | TCGTGTTCAC | GGCTCAGCTC | CGTCATTATT | GCGAAACTCA | 660 |
| CGAACAAGTT | GTCTTGTACG | CAAGGGACGA | GCTCACCAAA | CGTTGCGGAG | ACAAGTCGGC | 720 |
| GCTCGGGACT | CACACTCACC | GACTCATTCC | GCTCTTGGAT | CACGACAACC | ATCGCGAACT | 780 |
| GTGCAATGTG | CTGGTCGGCC | TGCTACACCA | AACACCCCAC | ATCTGGGCCC | GTTCCATCCG | 840 |
| TCTTATCGGC | CGATTAAGAA | ACTATCTACA | ACAGAAGTTT | CTCAATATCT | TGGTGGATAG | 900 |
| CGGACTCCAG | ATCGATAGTC | TTTTTGAGGC | TTGTTACCAC | AGCGAACGGT | ACCGCTTGCT | 960 |
| GTTCCAGATC | GAAAAAACGA | ACTCCACCCC | TAGCTCTCTA | GCCTGTGCAA | GCACCGTTTT | 1020 |
| ACCTGTCGGT | GAAAACGAAA | CTGAAGGCAC | ACCTGTCCCG | CCGTGTATTT | AATGAAATAA | 1080 |
| TAAAATGGTT | CTCATGAATA | AGACGGTCTT | AGTTTCGTTT | TTGAAAGGAC | AAGTATGAGT | 1140 |
| GTCCCCCAC | ACATCCCCGC | CTTGGCCGTG | GACTCGAGCC | TGAACTTTCG | TGCGCACCTG | 1200 |
| TTTTCTGACC | ACAACCGACA | CTTTCTAGTC | GATTAGTAA | CCCAAAGCTG | CAGCGGCTAT | 1260 |
| GTGGGACTGT | GTAACGCCGG | AATTCCCATC | CCCACCTATG | TACTGGAAAC | GCTAATTGAC | 1320 |
| TTTCAGGTTC | CAACCACATA | CACGAAAATT | AAGCCCATTG | CCGTAAAAGT | GCTAAAAATC | 1380 |
| TGTATTCTGG | CTAACTACCT | AAAAAACAGT | AAAGAATTAT | GGATTGATTT | CAAAGCTAAC | 1440 |
| CTAGACGAGA | TTAATTCTGG | TGCAAATAAG | CAAAGACTGT | ACAGAGGCTT | TTACAAACTA | 1500 |
| TGTCGTGATA | AAAACTCGAT | GCACGCGTTG | TCAGCTCATC | | | 1540 |

( 2 ) INFORMATION FOR SEQ ID NO:3:

( i ) SEQUENCE CHARACTERISTICS:
        ( A ) LENGTH: 1554 base pairs
        ( B ) TYPE: nucleic acid ( C ) STRANDEDNESS: single
( D ) TOPOLOGY: linear ( x i ) SEQUENCE DESCRIPTION: SEQ ID NO:3:

| | | | | | |
|---|---|---|---|---|---|
| GTGGCGCCCC | GGCTTCATTA | TAACGCCACG | TCGGAGCCCC | TGCGCGCCAC | AACGCCGTCC | 60 |
| GGCGCAACTT | CTGTCTCGGC | ACGGTACGAT | AAAAACAACG | TCCCCCGTCG | ACGTTGTTTT | 120 |
| CTCCGAGCGG | TGATCGTTCC | CGTCCCTCTC | CTCCCTCCGC | GGCCCCACG | GCGGCGGCCT | 180 |
| GCTCGCACGG | ACCTATACTA | TTACCGCCCG | ACCGCCGTCG | TCGTCATGAA | CTTCATCATC | 240 |
| ACCACCCGAG | ACTTCTTCAA | CGACGATTCA | GTCCTGCGAG | CCGCCGAGAT | GCGTGACAAC | 300 |
| GTGGCAGGCT | CGATTTCCAA | AGCTTACCGA | GGTACGATTC | GCGCGGAAGG | TAAGAAGAAG | 360 |
| CTGCTGCTGA | AGCACTTGCC | CGTGCCGCCC | GGCGGCTGCT | CGCGCCGCAA | CAGCAACCTC | 420 |
| TTCGTTTTCT | GCACCGAGCG | CGACTACCGC | AAGTTCCACC | AGGGCATCGC | ACAGCTCAAG | 480 |
| CGCGCGCCGG | CCGAACTGGA | CCGCCACGAG | ATCCAGCAAG | TCACGGCCAG | TATCCGCTGC | 540 |
| CGCCTGCAGC | CCAGTCTCCG | CGAGCCGCCC | ACGCCGGCCG | ACGAGCTGCA | GACGGCTGTG | 600 |
| TCGCGCGTGT | GCGCGCTCTT | GAACCAGCTG | GTTTCACGG | CCCAGCTGCG | CCACTACTGC | 660 |
| AGACACCAGG | ACAAGGTGGT | GAGCTACGCG | CGCGACGAGC | TGACTAAACG | CTGCGGCGAA | 720 |
| AAATCGGCGC | TGGGCGTGGA | AGTGCATCAA | CTGGTAGCCC | TGCTGCCACA | CGAGCGCCAC | 780 |
| CGCGAACTGT | GCCACGTCCT | CATCGGCTTG | TTGCACCAGA | CGCCGCACAT | GTGGGCGCGC | 840 |
| TCCATCCGTC | TCATCGGACA | CCTGCGCCAC | TACCTCCAGA | ACAGCTTCCT | ACACCTGTTC | 900 |
| ATCAACTCAG | GTTTGGATAT | CGCACAAGTT | TTCGACGGCT | GTTACCACAG | CGAGGCCTAC | 960 |
| CGCATGCTCT | TCCAGATCGG | TCATACGGAC | TCGGTGTCGG | CGGCCCTGGA | ACTCTCACAC | 1020 |
| GGCGCGGCGG | CCCGGGCCGCC | CGAGGCCGAT | GAAAACAACG | ACGAGGGAGA | GGAGGACGAC | 1080 |
| GACGAGCTCC | GTCACAGCGA | CCCGGCGCCG | CTTCACGAGT | CCAAGAAGCC | CCGCAACGCC | 1140 |
| CGTCGTCCCC | GCACACGCGT | CCCGCCTCAC | GAGCAAAAGC | CCGAAGAAAA | CGACCAGCAA | 1200 |
| GAAGACGACC | TGTTTCCCTC | CTGCAAGGCA | ACCGCACCAT | TCCTGCGCCC | AGAACCCTCC | 1260 |
| GTCTCCAACG | ACGACGGCAA | CGGCGGCGAA | CGCTGCGACA | CGCTAGCGAC | CGCCCTGCGG | 1320 |
| CATCGCGCCG | ACGAAGAAGA | CGGACCTCTA | GCCAGCCAGA | CCGCTGTGCG | GGTCGCCGCG | 1380 |
| ACCCCCTCAC | CTTCAGTCAC | CCCAGCCCTT | ACCCCCGTCA | CGTCCCCCAT | AACCCCGTTG | 1440 |
| TGTATTTAAC | GTCACTGGAG | GACAATAAAG | CGTTGATTTC | TCAACTTCCG | CTCTGGTTTT | 1500 |
| GGTTTCGTTT | TCAAAGGGAG | CCCCATCATG | GCCCAACGAT | CGCGAGCCCC | ATCC | 1554 |

( 2 ) INFORMATION FOR SEQ ID NO:4:

( i ) SEQUENCE CHARACTERISTICS:
        ( A ) LENGTH: 666 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| | | | | | |
|---|---|---|---|---|---|
| GGAATTCGAT | CGGATACCCC | GTCTACGTGT | ATTAATATTA | CATAAAATAG | GCTTTTTTTT | 60 |
| AAAAAAAGA | AAAGACATTT | TTCACTAATG | GTGTCATATC | ATTATAATAA | ACCTTGTTTT | 120 |
| CATCAGGAAG | GTATAAAAAC | AAATTCATAT | GCACTAAATA | ATATAGATTC | AAAACAAATA | 180 |
| AGGCAAAAAT | CAATGGCAAC | AGAATAAGCA | TATATATAAA | CATGGTGAAA | AATTACATAT | 240 |
| AAACACCAAG | AATGTGGAAG | ATTTAGCTGT | GATTAGCAAA | TTTTGCCTAA | TGGATATATA | 300 |
| TGTATAAACT | TGTCCCAATA | TCTACAGAGT | ACTCATTCCT | ATCAAACACA | AATAAAACAG | 360 |

| TTCTTAAAAA | TTCAGTACAT | ATTGTGTCAA | TTTAAAAAT | AAGCTTCAAA | GTTTTGATAC | 420 |
| TATAATTTAG | AAACTATCTC | GAGGGAAATA | ATATAAATAG | TTTAAATAAA | AGTGAGGTGA | 480 |
| AACTAATGTA | TATTTAGATG | AAGCAGTATA | GTTTTAAATT | TACATATTAT | AAAAGAAGAA | 540 |
| TATTAATGAA | CTAAACATAC | ATCCTAAGAA | GTTAGAAATA | GAATAGCAAA | ATAAACTCAA | 600 |
| AGAAAGCATA | AAAAAGAAA | CTGGTGGAAC | GGGAAACACA | CGTAGACGGG | GTATCCGATC | 660 |
| AAGCTT | | | | | | 666 |

( 2 ) INFORMATION FOR SEQ ID NO:5:

( i ) SEQUENCE CHARACTERISTICS:
        ( A ) LENGTH: 517 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

| TATCGATAAG | CTTGATTTCG | CGTTGCTAGG | CCACCACTAA | TGCATGATTT | TTCTTTCAAA | 60 |
| TATACCAACA | CATAAAATAC | GATAGTAGCC | ACACAGCAAC | AAATAATGAA | ATCATGTACC | 120 |
| GAAGAGGTTC | AGGTCCAGTT | AAAAATAGAA | AAGTATGAAT | AAAGTGCCTC | CATCCCTTAG | 180 |
| GGAATTCGAT | TTCGCGTTGC | TAGGCCACCG | CTTTGTTTTT | TGCAATCTCC | TACGGTAAAA | 240 |
| GTAATACAAG | GGAATGGAGA | GCCGCCGCTC | GATACGCACT | AGCACTGCAA | TTGGAAATTC | 300 |
| GATCCAAAGA | AGAACCGTGG | ACGCCACTTG | AACCTCGCAT | ATTTCAGCGC | GTGTATTTGG | 360 |
| AACACGACAC | GACTTCCCAA | CTCAACAATG | ATCAACTACA | TGTCAGCGGA | ACTGTGATTG | 420 |
| GAAATTTTAC | AAATACAGCT | TGGATGCATG | TTAGTCTGAG | TTATCCTAAG | TTCAAGGAAA | 480 |
| TGTTCGTCAT | GTCTACCAAC | CCAGACATCA | CAGTGAA | | | 517 |

( 2 ) INFORMATION FOR SEQ ID NO:6:

( i ) SEQUENCE CHARACTERISTICS:
        ( A ) LENGTH: 567 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| AAGCTTGATC | GGATACCCCG | TCTACGTGTA | ACACCTGGAA | AGTTAATGTT | CAGTGAAGCG | 60 |
| CCCCAATGTC | GCTGAATCCA | CCCAGCTCCT | CACCTGCAAG | TTGGCCAACA | TGATGTGTCA | 120 |
| AGTTGGGGAC | ATGAATGCTT | GTCCACCTG | CCCTGGGAGA | AAAGATCATA | GAAGTGAAAT | 180 |
| GACCTTGTAA | ACAGCAAAGT | CCTGTGCAAA | TATAATGGTC | CTTGTTGAGT | CTTTTCCACA | 240 |
| TTCATAATCG | ATGTTTGTCT | GACGCTGACC | CCTGCTCCAG | AACCACCCCC | CCCACTCCCC | 300 |
| GGTCTGCTGT | CGGGGAGCGC | CAGGACACAC | TTGGCTCTTG | GGCAGTTTTA | AGTAGGTTTA | 360 |
| ACGTTCTCAC | ACTGATAGAA | GTGGTGTACT | TTAAAGATGA | ATTAAAATGA | ATACTTTATT | 420 |
| AGTAACTCAG | CTGTGCTTAC | TGCTAGATTC | CTTAAAATAA | TGCCCCTGCC | TTTCCCACAA | 480 |
| TGACAGGGCT | TGAATTTCTT | TTTTTGCGAA | GTGTGGTGGT | GAGTCACAAT | CATTTCCGAT | 540 |
| GGACGCGTTG | TCAGCTCATC | GAATTCC | | | | 567 |

( 2 ) INFORMATION FOR SEQ ID NO:7:

( i ) SEQUENCE CHARACTERISTICS:
        ( A ) LENGTH: 160 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | | | |
|---|---|---|---|---|---|
| GAATTCTGGT | ATGAGACGGA | CGGCACGCCG | GTTCAATCCC | GGAAATTATT | ACAATGTCGG | 60
| CGGCAATTCC | AAATTCTATG | GCGCAGTGCT | GGTGCGCTAT | CGGCGAAGAT | TTTGAGGAGC | 120
| TTGCGCATCT | TGAAGGCGTG | TCTCCGGCAT | GGCCTTTTGG | | | 160

( 2 ) INFORMATION FOR SEQ ID NO:8:

( i ) SEQUENCE CHARACTERISTICS:
        ( A ) LENGTH: 784 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:8:

| | | | | | |
|---|---|---|---|---|---|
| TANGTACACN | CNCTNGAGCT | CTCGCTNTCT | AGTAACAAAG | GCTCAGTACG | TGGNAAGGGG | 60
| TGTNGCGTCA | CGCCTACACA | CCTGGGCTGC | TCGACCATCA | TAACGTGTGT | GATCTGGAGG | 120
| GGCCTTCTAN | ACCTGTCGTN | GNTGNGGACC | CCNCAGNTTT | NTATCNGTAG | CATACTNACN | 180
| NAACGCTCTA | CCNCNTCNAC | ATTTGANNCN | TTCCTATTTT | TTTCCCCCA | CACTTTTTNT | 240
| TTTTCANTTT | ACCTCTNANC | TANTTTCCNA | CATTCTNCNN | NNNNCATNTC | TNCATCCCCC | 300
| ACTAATNTTC | TTCANTCNNT | TATNNATCAA | NCCNCNNTCN | CACNTTNCCA | TTNCAACCAC | 360
| CNANNNTNTT | ANCTCNCTTA | NNNTTTCTCC | TTNNNACTAT | CAATCTTNTN | TNACTNNACA | 420
| CCNANCACTC | NAANCTCCAT | TTTTAAANNN | TNNANNTNTC | NTNNCCNTTN | TNTAACCCNC | 480
| TTNANCNTAC | NTCNNTAATT | NCTTTCCNA | ANATTNANNC | CNCACCNANT | TATNNNTCAC | 540
| CANNCAACAT | NTNNTATNTC | TANNNNANNN | TTNTTTNNCN | TAAACNTCCT | ACTTCTANNT | 600
| NTNCANNTAA | TANAATNCTA | NACTNCTCAC | CTTNAACNNC | TNCACTNCAN | ACNTNACNNN | 660
| NTCNNNTTTT | AAACTNCNNT | NNTNNNTTTT | TANATCCCNT | CTCACTTNAT | CTNATAANNC | 720
| NNATCCATNT | TTGNCCNCTC | ATCTATCNTA | CTNNNNACNC | NTNNCTNCCN | TCTTNCTCAT | 780
| CCAA | | | | | | 784

( 2 ) INFORMATION FOR SEQ ID NO:9:

( i ) SEQUENCE CHARACTERISTICS:
        ( A ) LENGTH: 680 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:9:

| | | | | | |
|---|---|---|---|---|---|
| TGTTTTNCAN | CTTCTCAAGG | GACCCCCCCC | CGAGGAAGAC | GGTATCGATA | AGCTTGATAT | 60
| CGAATGCCCT | GCAGNCCGGG | GGNATCCACT | AGTTCTAGAG | CGGNCGCCAC | CGNGGTGGAG | 120
| CTCGAGACAG | GTGNCGCGAT | ATGCCNCGGC | CTGGCACCGC | GAACACAGCG | GCCCCTGGCC | 180
| GTGACACGTG | AGCTTCAGGA | GTCGCGGGAT | AGTGACGGAG | CGCACCACCA | CGGTGGAATC | 240
| GCACGTCCGC | GCAGAGCACG | GTAGAATGAT | GTCAAACGTG | ACGAGGTGGT | CATAGACCGC | 300
| ACACGCGGTG | TTCANCCCCA | AGACTGNCTT | CCAACCAAAC | CGNAAACAAC | GTTGCCCACA | 360
| NATCGTCTCA | GAGACANCTT | CGTAAACACG | TTCTTTTAAT | GACACGCTGA | CTTCCACAAA | 420

| AGAGAACAGT | GCANCAGTTC | GGCGTTAGTA | TTGAAANTGA | CACTCTTTTC | TTGGCGGTCT | 480 |
| CTATANTAGA | ACATAGAGTT | AAGGGGGGAA | TTCTGCTCGC | AGNGNAGGTT | CTCCTGGCCA | 540 |
| AGTTCAAGCA | GGGGNCGAAT | TTCGGANAAC | ACGGNGACAG | GATCTTGGTT | TAGTGGNGTC | 600 |
| NACTCAGNGA | AAAGCACAGG | NGGTTTATAC | GTTCTTTNTC | CCGAGNCNCC | ATCTATATTT | 660 |
| GGTGTCNGGC | CCNTTTTTTT | | | | | 680 |

( 2 ) INFORMATION FOR SEQ ID NO:10:

( i ) SEQUENCE CHARACTERISTICS:
        ( A ) LENGTH: 521 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:10:

| GAGCTCGCCT | CTGGCTGCAC | CTGTGGGGGG | CTCTTTCCAT | GTCCTCACAC | GTCTCTGTCA | 60 |
| CGTCCGCCCT | CGTACAGNAT | CACCGCTCTC | CTAGCTTTCC | CAATTTGNG | GTCAAACACG | 120 |
| TCACAATTAC | ACTGCGTCAA | CCACCTGCCC | GCGAGCCATT | CACACGGTAC | TTATGAGAGC | 180 |
| GACAGGTAGN | CCCTTGNCAG | TCCGTCAGT | CTTGCCCCAA | TAGAAGCCAT | CACAGACACT | 240 |
| GTCCATCACA | GNCCATCTAA | ATTACANCAT | NACATTATTC | ACACCGAGAC | GANCNANNNG | 300 |
| GCTCGTNGTG | ATGATCGAAN | TTTGNGATCG | CNACTGCGGT | GANCAGTTGC | AGATCGAACG | 360 |
| GNTGAGGACG | TCGTNGTAGA | CAGGAGTNTC | GNCAGNGCAA | ANCTTACTGN | TNGGCANCGG | 420 |
| CCGANTGANG | CCGANAGCCA | NAGACCGACG | TCTCGANTCA | ATTCAAACAA | AGACGTCCGG | 480 |
| TAGCAGGGTC | CGTAAATAGG | GCTGCGTTAA | AACNCNTGNC | G | | 521 |

( 2 ) INFORMATION FOR SEQ ID NO:11:

( i ) SEQUENCE CHARACTERISTICS:
        ( A ) LENGTH: 514 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:11:

| GAGCTCCATC | TGTGTGACGT | TAATCTCCAA | ACACCCTTCA | AAGAAATGCA | CGAACAGTTA | 60 |
| AGTTACCTGA | TTACAGGACA | CACCTCAACC | ANCTCCATGT | CCTTTTCCGA | CGAGCTGCTT | 120 |
| CAACTACGCT | CACAGTTCAC | GTACGCTACT | CAGGTAAAGG | AAGACACCGA | AAGCAAAATC | 180 |
| CATGACCTGA | TGCTCAACAT | CGAAACCGNC | ATCCAGGAAC | CTACCACCCG | CAGCTCCAAT | 240 |
| ATCGNCATGG | NCATGGTCCA | AGAACAGCTA | AANGAACTTC | AACAGCTCGG | AGGNGCCANC | 300 |
| ATCCCTGAAA | TAGCTACCCG | TCTGGAAAAG | GTACACAAGG | TGTTGAATTC | CCTCCAACAN | 360 |
| GAAGNACAGG | GGGGCAGAGT | CTTCGTCAAC | GGGCTAAATT | ATGACACTTA | CCAANCGATC | 420 |
| AANCACTCAN | NAGACANGCG | GGCTTTCAGA | CTGNTGGGGA | GGNGGCAGCT | CACGAATTTC | 480 |
| ATCCAGAANT | CNGGTTTTTT | CAAACCTCTG | GCCT | | | 514 |

( 2 ) INFORMATION FOR SEQ ID NO:12:

(i) SEQUENCE CHARACTERISTICS:
  (A) LENGTH: 671 base pairs
  (B) TYPE: nucleic acid
  (C) STRANDEDNESS: single
  (D) TOPOLOGY: linear (ix) FEATURE:
  (D) OTHER INFORMATION:
    "N" represents any base.

(xi) SEQUENCE DESCRIPTION: SEQ ID NO:12:

| | | | | | | |
|---|---|---|---|---|---|---|
| NGNTTGACAC | TNTTAAGCTC | GATGCCNACA | TAAGCTGACG | GNGACAAACC | AGGAGCGGGT | 60 |
| ACAGACACCG | AGGACGATTT | ACGCGCGCGC | GATGCACAAG | CTCTTGGGCT | ACCGGCCAAC | 120 |
| GCCGGCTGCA | ATGCCCGTCN | GAGCGACCTG | GGTCAGCTGA | GTCGTGCTCT | ACGTTGCGAT | 180 |
| TGGCGATACT | GGCGACTCAC | TACTGCCCCG | GAAGAATACG | AAGACCCCGG | TGAAGACGAT | 240 |
| TCTTATAGCG | AGTTACCATA | CCGCACGTNG | GNTCCCANCG | ANTATNACNC | TCAGTGNNAT | 300 |
| CCANAGATCG | TATTCGGNNC | AANCACAACC | GTCGCTNGCC | GACTGTNTCA | TCACCGAGCC | 360 |
| AGNGTCGGTN | GACCCCTNCA | CGCCCCCCCC | CNCNCCCCCT | TTTAGCCNNC | CCTCCCCCCG | 420 |
| NNCNCNTGTC | CACCCCCCCC | CTANCCAAGN | NCCCCCCCGC | CNNCCCTNCN | CCNTNCCCNT | 480 |
| NNTTNAGNTT | CTTTTCAAGT | CTTTCATATT | TCTNNATTNN | CNCCTTTTCA | TTTCGATGNA | 540 |
| GGAANCTNCG | TNNNGNTTTG | NNNTTTCTTC | CNGCCTANGT | TGTTTNANNT | TTTTNTTNNN | 600 |
| CNNTTNNNTA | NAATCCNGAG | NNNNTTNCTC | NCTTTANTNT | CGTATTTNTG | AAANTGTTTT | 660 |
| TCACCCCCCC | A | | | | | 671 |

(2) INFORMATION FOR SEQ ID NO:13:

(i) SEQUENCE CHARACTERISTICS:
  (A) LENGTH: 616 base pairs
  (B) TYPE: nucleic acid
  (C) STRANDEDNESS: single
  (D) TOPOLOGY: linear (ix) FEATURE:
  (D) OTHER INFORMATION:
    "N" represents any base.

(xi) SEQUENCE DESCRIPTION: SEQ ID NO:13:

| | | | | | | |
|---|---|---|---|---|---|---|
| GAGCTCTGCC | GGGCGTTTGG | AGGTGAACAG | TTTGACCGGC | TGCTCCGTGA | CTGATGGCCG | 60 |
| CAGCGGCGGC | CGACGGGTTA | GGATATTGAC | GACCTAACAG | TTCAGTTATG | TGAGGAGGAT | 120 |
| NAGTTGTGAG | CGGTGAAATC | ATAGTACACA | GGTACAGGCG | AGGGATATCG | CCGNAGCCGT | 180 |
| ATTTCCAGAA | CTCGTCAGCA | TCGGTGGNCA | CGAGATGCAG | AGTTAGTCGA | GGAAAGTCGA | 240 |
| GAAGAAAAAC | ACNGAAGTGG | GGTCCNAGAG | CGANGTNCAG | NNCTNCATNN | TGACAGATAG | 300 |
| TTGNTTGANA | NNCANNGCCA | GNAGTNGTTT | CCTTNCACNA | TNCANGNCAA | TNTAANANCC | 360 |
| NCCCANTNCG | TCNTTTTGNT | NNACANTTNN | CCGNANTTCC | AANNTNNNCC | CACCNNTTNN | 420 |
| NCNTTTNCNT | NNCCNNNNNT | TNNTCNTTTC | AATATNACCC | NNCCNNNNCN | TCTATTCANN | 480 |
| NNTNTNNNCN | CCTCTCCCNT | CNNAACNNTT | TNTNNTNNTN | NNTNNTNCNC | TTCNNACNNC | 540 |
| NTCCCTCCCC | ATCCNTCNAN | CNNNNTNCNC | NTTTNNCNNN | NNNTTTTTTT | TTTANTNNTC | 600 |
| CCATTNNTCN | TCNTTA | | | | | 616 |

(2) INFORMATION FOR SEQ ID NO:14:

(i) SEQUENCE CHARACTERISTICS:
  (A) LENGTH: 601 base pairs
  (B) TYPE: nucleic acid
  (C) STRANDEDNESS: single ( D ) TOPOLOGY: linear ( i x ) FEATURE:
 ( D ) OTHER INFORMATION:
  "N"represents any base.

( x i ) SEQUENCE DESCRIPTION: SEQ ID NO:14:

| | | | | | | |
|---|---|---|---|---|---|---|
| GAGCTCTACT | AGACGCGGAG | AGACGCGTTC | GCGACGGAAA | AATTCCGGTA | CCCTTTGTGG | 60 |
| ATCGCGATAG | CCTGTTGGCC | AACGTTATTC | CCGTCGCCCC | CACTCCCAAT | CCGGAAANTN | 120 |
| NAGGAAGACC | GGAGAAGAAA | GCACTGACAC | GACAGTGTTC | GNTCCCTACC | CCCCACCCTA | 180 |
| AGAAGTTCGG | AGTNCAGCCT | GATTCCGATA | GCGACAGNGA | TACGATTATC | GATTCAACTA | 240 |
| TGGAAGGNGC | GGNATCTCTG | TAGATTTTTT | TTTGNTGAA | TTGNGCAACC | CGCANTNGCT | 300 |
| TGGTGTNACT | GTAGACAAGN | CTNCTNTNAA | TCANTAGTNT | TNNTTTNGTA | ATAAAACNGN | 360 |
| TTNGTTTNNT | TTAATCCACN | NAGTNGCNNT | GTNTTAATCT | TNNTTGTGGG | NTGATNAGNN | 420 |
| CCNNCCCNCN | NCTTTNACTA | ANTNNTTNTA | ANTTNGNNNN | TNNACNNNNT | NTNNTNTNTN | 480 |
| TNTTCCCNNT | NTNTNTCCCC | NCTTTNNNNT | TNNNNTTNNN | CNTNNTTNTT | NCNNNCCNTC | 540 |
| TNTNTNTNNN | CNTTTNCNTT | ATCTNNTCTC | NCNTATTNTN | NNCCCCTCNC | NTCNCNNTTN | 600 |
| T | | | | | | 601 |

( 2 ) INFORMATION FOR SEQ ID NO:15:

( i ) SEQUENCE CHARACTERISTICS:
  ( A ) LENGTH: 590 base pairs
  ( B ) TYPE: nucleic acid
  ( C ) STRANDEDNESS: single
  ( D ) TOPOLOGY: linear ( i x ) FEATURE:
  ( D ) OTHER INFORMATION:
   "N"represents any base.

( x i ) SEQUENCE DESCRIPTION: SEQ ID NO:15:

| | | | | | | |
|---|---|---|---|---|---|---|
| GAGCTCCTAC | CCTGTGCCCT | TATACCATTC | TAGGCACTTT | ATTTTTTACA | TGGCTTGCCT | 60 |
| CTGTTAAATG | TCACCGTAAC | TCCCAGATAA | CCTCTTCTGA | TAGCTGGGAA | AACCAAAGCA | 120 |
| CAGATTGGTT | TATAAACTTG | CTCACACAGC | TAGCATCAGA | GAGACCTGGG | ATGTCTCATC | 180 |
| ATTTCTGTTC | TCGTATCAAA | GAGGGCCCTT | GTGAGCCTCT | CAGTTGGCCG | ATCCTAACAC | 240 |
| TGGTCAATTG | GAATCTACTC | CCCAATGTTC | CAAGGAATGG | ATGTCATGAA | CCATGGNAGG | 300 |
| TGGNATGGNT | GCTGGAATCC | AGNNNNGGTC | CAGGTGANGN | CTCAAGCCAT | ATTGNAGGTT | 360 |
| GGCCTCAAGA | NTTTGGCCTC | CCCATNGGGT | TATGATGNNG | GGGGTTNCAT | NTTCACCAA | 420 |
| ATTNGNAANT | TTNGGNCAAN | TCTTTCTTTT | ANNNAAAANT | NTTGGNCTCA | CCNGGNAANA | 480 |
| AANANNAAAG | GGGGGAANNN | TNNNNNNTNN | GGNTTTNGNN | NNNNTTCCCN | NTNCTNTTTT | 540 |
| TANNNNGNNN | NNNNNTGGGG | NNNANNNNNT | NNCCCCNNNN | TCNNNNNAAA | | 590 |

( 2 ) INFORMATION FOR SEQ ID NO:16:

( i ) SEQUENCE CHARACTERISTICS:
  ( A ) LENGTH: 637 base pairs
  ( B ) TYPE: nucleic acid
  ( C ) STRANDEDNESS: single
  ( D ) TOPOLOGY: linear ( i x ) FEATURE:
  ( D ) OTHER INFORMATION:
   "N"represents any base.

( x i ) SEQUENCE DESCRIPTION: SEQ ID NO:16:

```
GAGCTCCTCG  GTGGGACAGA  GCGTANAGGC  TGGAGTGCTC  GGGGCGCTTC  GTGACATTTT    60

ATATCAATAC  GCTGACAACG  ATGAGTATGG  GCTATACGTG  GACTGGTACG  TCACGGTTGG   120

AATCATCCCT  CTGATGGATG  TCAAGTCTAA  ACCCGCCGAC  ATCACGCAGC  GCGCAGGCTT   180

CGTCCGAGCC  GCAATCCACA  GAGCCACAGA  GACTCACCCG  CTAGCTCAAG  ATTTACTGAC   240

CGNTAACCTT  CCCGCTTCTG  CAGNAAGTGN  GTAACGCATC  TTNTNCGCGG  GTCCCCAATC   300

GTTANCTCCC  CCGNAGNTNN  CGGATCTTCA  AACGAATCCC  CTCCGGNAAA  GATTGNNGNG   360

CANCCTANNT  GAAAAGCATA  CCCGCNGCTA  TNTTCTTACA  GANCCNNTTN  GCCTNNNAAC   420

GNNAACANNT  TNTTCTTCAN  CNNCCCCATC  GNCCCACCTT  CAGNAAGANA  TTTNGGCGTT   480

NACGAATNCC  TNTTTNCCTC  ACNAGNAGTT  CTTCCNATTN  CNTNNNAANT  NTTCANTCAA   540

GCCCNCACCN  CNCCCCNTNN  TTTACTTAAA  AATCNCCNNT  CTGNAANCAC  NCCCNGAGCN   600

ATTCNANNNN  NCCCANAACT  NTTTTNTCT  TNTCCNN                               637
```

(2) INFORMATION FOR SEQ ID NO:17:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (ix) FEATURE:
        (D) OTHER INFORMATION:
            "N"represents any base.

(xi) SEQUENCE DESCRIPTION: SEQ ID NO:17:

```
GAGCTCCTCG  GTGNGACAGA  GCGTACAGAC  TGNAGTGTTC  GGCGNGTTNC  GNGACANTTT    60

CTATCAATTN  GCTGACAANG  ATGACTANNG  NNNTATTCNT  TTNCNTGNNA  CNTTATTTTT   120

TNANNTNAAC  CCCACTTATN  NTTCNCATAT  NCTCTNACNN  NNCTNANATC  AACCTNATNA   180

ATCTTCCNAT  ANTNCNTNNT  CTTACTACCA  TTTTNCTNCT  NGATTNTCCN  ATTNCNTTC    240

CACTTNTNTT  ANNNTCCANN  TTTNCTACTN  CNANTNNCNT  TTATNCNCNC  TCCATCTCTN   300

TTTCCCTCAT  NNTCNACTTT  TNATANTNCN  CTTNACNNCT  CNNACNCTAT  NNTTNNACC    360

TTCCANCTAN  NCAATCNTNT  ATNNCTTTNT  ATTAATTNCC  TAANCNCNCC  TTNNCCNNTN   420

NANTCAAAAT  TNCACTATTN  NATTTATNNA  CNCNTNTTNN  TTNCTANTNN  CACTCATCNC   480

TCTAAATTNN  CNNCTANNAN  TTATNTCAAA  TNTANTCTTT  NTNTATTTAA  NATNATCTCA   540

CCNATTTCTC  TTATACNCNA  TNTNNNANNN  CATTTNTANT  TAAAANTANA  NTATTTNTT    600

TNTTNTNNTN  NNTTNTCNCT  CNCATCTNAC  ANNNTTTANA  NTNCAANNTT  TTTNNCCTTC   660

TATCANATN                                                               669
```

(2) INFORMATION FOR SEQ ID NO:18:

(i) SEQUENCE CHARACTERISTICS:
        (A) LENGTH: 715 base pairs
        (B) TYPE: nucleic acid
        (C) STRANDEDNESS: single
        (D) TOPOLOGY: linear (ix) FEATURE:
        (D) OTHER INFORMATION:
            "N"represents any base.

(xi) SEQUENCE DESCRIPTION: SEQ ID NO:18:

```
GNNTTTGACA  AAGCCCGTNG  TCACAAACGT  CNCGGAGACN  AGTCGGCGCT  CGGGACTCAC    60

ATCCACCGAC  TCATTGCGCT  CTTGGATCAC  GACAACCATC  GCGAACTGTG  CAATGTGCTG   120
```

```
GTCGGGCTGC  TACACCAAAC  ACCCCACATG  TGGGNCCGNT  CCATCCGTCT  TATCGGTCGA    180

TTAAGAAACT  ATCTACAACA  GAAGTTTCTC  AATATCTTGG  TGGATAGNGG  NCTCCAGATC    240

GATAGTCTTT  TTGAGGGTTG  GTTACCACAG  CGAAGCGTAC  CGCTTGCTGT  TCCAGATCGA    300

AAAAACGAAC  TCCACGCCTA  GCTCTCTAGC  CTGTGCAAGC  ACCGNNTTAC  CTGTCGGTGA    360

AAACGAAACT  GAAGGNACAC  CTNGNNCCGC  CCNNGTNTTT  ANTGAAATAA  TAATATGGGT    420

NCTCAANGAA  TAAGANGGGG  CTTTTNTTTC  GNNNNNGGTN  NGACAANTNT  NANTCTTCCN    480

CCCNATNCAA  TNCCTNNCTG  GCCCGTNNNN  TTCGNCTCCN  NTTCNTTTNT  CTTNGGTCCT    540

GTNNTTTNCT  CATNNNCNNN  ANNTCCTCCT  NGNNCTNCTC  CCCTATCNTC  NNNCTNNTTT    600

TNNNTNNCTC  NCCNNNNNNT  CNTNTCNCTN  TCNTCNTCTN  TNNCCNNNNT  NTTCNNTCTT    660

NCCCTTCTCT  TNNTNNNTTN  NTTCNNCTCT  NNTNTNTCNT  TTNTNCNTTN  TCTCC         715
```

( 2 ) INFORMATION FOR SEQ ID NO:19:

( i ) SEQUENCE CHARACTERISTICS:
        ( A ) LENGTH: 737 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:19:

```
TTTTTTNNNN  NNTTTTTTTN  CGCACCNNCG  CAATTAACCC  TCACTAAAGG  GAACAAAAGC    60

TGGAGCTCCA  CAGCTTTCCC  TTGGCATGGA  AAGGGCCAGA  AGAGCCAGTG  GAAGGGACCT   120

GCCATGCTAA  GGGGCGAGGT  GACCCCATGA  TGAAGGCCAC  AGAGTGTTTA  ACTTAGTAAG   180

GGTCAGGTGG  AGGGTGCATC  TGAAGCTCAG  AAGGCCGAGC  AGAGCAGTGA  GGAGCTGGGA   240

TGGGGCAAGT  CGGCAAGGGA  AGAAGACAAA  TTTCAGGTTC  ATCTCCATAC  TCCGGGAGAG   300

AAAAGCCAGA  AGTAGNCCAT  GGACCAGGCG  TCTCTGNCTC  TACCTCCTGC  ACCTTCTCCA   360

GTTCCAGNCA  CTCCCGNTCC  CCCTTCACTG  NAGNCACAAC  CAGACTCCAG  NCCTCCAGNN   420

NTGNCTNGNT  GCCTNNGGNC  CACAGNNCTC  CCNNACCTCC  CNTCTCTCCT  CCNNNNTCAN   480

ANTCANNTTC  CNNATCTTC   CTTNNNNTTN  GNNCANNNNC  CNNCTCTCNT  CATNCTCTNT   540

NNNNNTTNNN  NNNTNTTCAN  NNNNCTNNGN  NNNNNNNNTT  CNNNNTTNNN  TNNNNNGNAN   600

NNCNTNNNNA  CCNNTTCCNN  NNNNNNNNNN  NNNNNNTCNN  NNNNGNANNN  NNNNTNNNNN   660

NNNNNTNNNN  TNNNNNNNNN  NNNNCCCNN   NNNNNNNNNN  NNNNNNNNNN  NCNNNNNNNN   720

TNNNNNNNNN  NNNTNTT                                                      737
```

( 2 ) INFORMATION FOR SEQ ID NO:20:

( i ) SEQUENCE CHARACTERISTICS:
        ( A ) LENGTH: 779 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:20:

```
GGTTTNGNAA  CTCTTGAAGC  TCTCGNTCCC  CTAGAAACAA  GGCTCAGTAC  GTGGAAGGGG    60

TGTGGCNTCA  CGCCTACACA  CCTGGGCTGC  TCGACCATCA  TAACGTGTGT  GATCTGGAGG   120
```

```
GGNTTCTTTA  CCTGTTGTGC  TGCGGACCCC  GNAGTTTCTG  CTCGCGGNAC  ACGTGTTTCG      180

GGCGGGAGAA  GCACGGTTGA  CCATTCCCCG  CCCTGCTCCC  CAAGGATCTT  TTACGAGCCC      240

GNTCGCGATT  ATATGACGNA  TGTGAACCTG  GCTGAACTTC  TACGTTTATG  TGTGGNATCG      300

CGGCTATGAT  CGCCCTTCGA  CTTCGGATCC  NACGCCAGGG  GNTGATGACG  ACCGANCTNC      360

NGNCNGNCTT  TTAATAGANC  CGCCCTCNCN  TNCNCACCNN  TCTCAACAGG  ANNTTGCTTA      420

AAAGNCGTGA  TCCNANCGNC  NGCTTCTTNG  GCCGTCNCNA  TANTTCNCTC  TTCNACNTNC      480

CTNNCTTNNT  CCTNACANTC  TNNCTTCNTC  CNTCNNGCCT  CNNTGCACNN  CNTATTTCTT      540

CTNCATCTNT  TTANCCTCCC  NTCNNANTTT  NNNTTNNCNA  TCACTCCANN  CACNNCCNNN      600

TNTTANCCCC  CANNTCCCCC  CCCATTNTTN  NCANCTNCTC  CNCTGCCAAN  NNCCTNNTTT      660

TTANCCCCNT  CTNNCCATNT  TTTNCTTNGC  TTCNCNTANA  TCCANANTCC  CCCTNNACCT      720

TACANCTCTN  TATCCTCTNA  TCCCTCCNAC  TATACCCCTT  NTTNTATCNT  NTCCNCCCC      779
```

(2) INFORMATION FOR SEQ ID NO:21:

(i) SEQUENCE CHARACTERISTICS:
        (A) LENGTH: 682 base pairs
        (B) TYPE: nucleic acid
        (C) STRANDEDNESS: single
        (D) TOPOLOGY: linear (ix) FEATURE:
        (D) OTHER INFORMATION:
          "N"represents any base.

(xi) SEQUENCE DESCRIPTION: SEQ ID NO:21:

```
GAGCTCACAA  AACGGTGCTG  GTTTGGTTTT  TTACTTGGCC  CACGGATACG  GGGGAGAGGT       60

AGACAGGCCC  GACTTCTTTG  TTANTCTCCG  GGTCGTCGGC  GTCCGCCACG  CTGGTCAGCA      120

GGTGTTGTTT  ACTCTGCACC  AATTCCGACA  GCGGTGTACT  CGCCATCGCG  CCCGTGCCCG      180

ACCACATGTN  AAAAAGCAAG  TACGTGAAGC  GCTCGGGGGA  CGGAGTGCTG  TGTTCTGTAA      240

ACATCTGTAG  AAGTTGCTTC  GGNGCCTCTG  GGATTTTCAC  AACGATTGTC  TGTTTGTGGT      300

GGCTAAATCG  CCGGTGTTTG  GTGTACGGTA  CCGTCTCGTC  ACCCATCACC  ATGGCTTTTG      360

GACCACTGCC  ANATGGCTCA  GGGTTATGTT  TTCGGTTCTT  CCACTGAATC  TCCCAACTGC      420

TTTTCGAAGC  AGCGATTAAT  ANAAAAATGN  AGATGGAAAT  CAAACAACNT  CAANGAAATN      480

TTGTCGAAAA  GAGNTNGTCC  ACGTGAAGGT  CCCNANNNTT  CTTGACGCAA  AGTATGATTC      540

AACTCGGNNA  TNGTNANTNG  CAAACTTTAA  GGCGCCCNCN  NGGCCCATTA  NATTANACNA      600

NAGAAACTTC  NCCGNATNGC  AANTTGTCTT  ACTTGTCAAN  AGTTTATNNG  GAGTTTGACG      660

TTNNTCNAGG  GNCAAGTTTT  CT                                                 682
```

(2) INFORMATION FOR SEQ ID NO:22:

(i) SEQUENCE CHARACTERISTICS:
        (A) LENGTH: 680 base pairs
        (B) TYPE: nucleic acid
        (C) STRANDEDNESS: single
        (D) TOPOLOGY: linear (ix) FEATURE:
        (D) OTHER INFORMATION:
          "N"represents any base.

(xi) SEQUENCE DESCRIPTION: SEQ ID NO:22:

```
TGTTTTNCAN  CTTCTCAAGG  GACCCCCCCC  CGAGGAAGAC  GGTATCGATA  AGCTTGATAT       60

CGAATGCCCT  GCAGNCCGGG  GGNATCCACT  AGTTCTAGAG  CGGNCGCCAC  CGNGGTGGAG      120
```

```
CTCGAGACAG GTGNCGCGAT ATGCCNCGGC CTGGCACCGC GAACACAGCG GCCCCTGGCC      180

GTGACACGTG AGCTTCAGGA GTCGCGGGAT AGTGACGGAG CGCACCACCA CGGTGGAATC      240

GCACGTCCGC GCAGAGCACG GTAGAATGAT GTCAAACGTG ACGAGGTGGT CATAGACCGC      300

ACACGCGGTG TTCANCCCCA AGACTGNCTT CCAACCAAAC CGNAAACAAC GTTGCCCACA      360

NATCGTCTCA GAGACANCTT CGTAAACACG TTCTTTTAAT GACACGCTGA CTTCCACAAA      420

AGAGAACAGT GCANCAGTTC GGCGTTAGTA TTGAAANTGA CACTCTTTTC TTGGCGGTCT      480

CTATANTAGA ACATAGAGTT AAGGGGGGAA TTCTGCTCGC AGNGNAGGTT CTCCTGGCCA      540

AGTTCAAGCA GGGGNCGAAT TTCGGANAAC ACGGNGACAG GATCTTGGTT TAGTGGNGTC      600

NACTCAGNGA AAAGCACAGG NGGTTTATAC GTTCTTTNTC CCGAGNCNCC ATCTATATTT      660

GGTGTCNGGC CCNTTTTTTT                                                 680
```

( 2 ) INFORMATION FOR SEQ ID NO:23:

( i ) SEQUENCE CHARACTERISTICS:
        ( A ) LENGTH: 822 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:23:

```
GNNTNTGCAC NTNNTTATAG GTCTNANTCN CGTTNAAAAC ATTTGNGGGT ACAGCGNTGC       60

CACCGNCCGA TGGAGAACGT GTTGTATGNC CATNTTCTNC GNACAGCCNG GGAGATGATC      120

TGATGANACA NGNNCCACTG ANGAGTGGAG GANGATNATA ACGACTACCC GNCNATTCCA      180

CAGGTGCGAC AGGTTCCCCA GTATCGATCG TCCATCAGCN TCGGCTGGNA CCCACTGANG      240

GTGANCGCCC NNATTCACAC AGTTAAGATG GCTGAGCAAN GNNGAGGAAG ATNACGTCTC      300

GCTGCACANN ANCGCCGCAT TGACCCGTCN GAAGNNCGGC ACCATATGGT GCTNACCCTC      360

GNNCCCCAGT CCTGTCGACG GCTATTGANT NNNTNNTTN AANNCCTTGG CTTANTGTTC       420

NTTTGNNCAG NTTCACGATN TTCTNNGCCC CNANTTTTTC NGGATCCCCT CNACATCTTA      480

NATGTTCGNN TCGTTTTTAA NAATCCTNCG GNTTCCCGTT CNTTTANTCC ANTCNNTCNT      540

NCGNNTTNTC ACNATGNCNN ACTCNNGTNN TNTCANTNTA TTNTTACAC GNATCTTTAN       600

NCTTTTCNCN CCCATTCCCC NCNGNCNNCN ANGTNTTNT CANNNNTCCC NTCNNNCGTC       660

NNCNANCTCT NCAANCANNA GCNTCTTTNN TTGCNCATNT NGTCNTTGGA ANCTNTNNCN      720

TTNNAAGNNN ANNGTACNNC CTCTTTNTTT NANNTNACNC CANANACANG NNCATTCTTA      780

AATCNNCNTT ACNCCCTTAC TCCATATCTN TATCTATANT TT                         822
```

( 2 ) INFORMATION FOR SEQ ID NO:24:

( i ) SEQUENCE CHARACTERISTICS:
        ( A ) LENGTH: 655 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:24:

```
GAGCTCATAC TCCGCTGCTG AGATGGTGGC CTGATAGAGT CGTCTTATGG CGGTGACGGG       60
```

-continued

| | | | | | |
|---|---|---|---|---|---|
|TACGGGTAGG|TGTTCCACCG|AGGTGTGCCG|GGAGGTTGGG|CGTNTCTGCA|GATGGGTTAT|120
|ACACANGTTA|CGANTTAAAC|ATTTGGAGTG|AACGTCTCCG|TCCTTTGGCG|CGCGANTCTT|180
|GTAGGGCGGC|ATCGCGCAGC|ATATAGTTCG|CGATTCGCNA|TTCCTCGTTC|CCCGTCTATC|240
|GTCCATTGGN|NGAGGGNACA|CAGANTATAG|TCTCCNAGGA|CACAAAAGCG|TCTAGGTGCC|300
|CTCAACGGCT|CGCAGGNAAA|TCAANAGAGC|CCANNTTNTT|TNCTTCGANG|CAAAGGTTTC|360
|GNCACCCCCG|TCCGTTTATT|TTGTCNCCGA|NAANATGGCT|TCCGCCNGAN|TTTGNTTTGT|420
|TAGTCANTTC|CCGNNGNNGA|GGNGNATTTT|NTNANNTANC|NTTCANATTA|NNTTAANCNT|480
|CNCCAAGCNT|TCTCTTACCT|NTTACNNCNA|ATNCAACCA|AATCATCNGN|TTCCGCTGNT|540
|TAAACTGAAT|NTNACATCNT|TCTCCACTAA|ANCCNNTCNT|NCANACNCNT|NNCCTCCAAT|600
|TCTCCTCANA|ATACCNAATA|NCNCNNCCAT|CCNNCTNANT|TNTGNNTCAC|TCNTT|655

( 2 ) INFORMATION FOR SEQ ID NO:25:

( i ) SEQUENCE CHARACTERISTICS:
        ( A ) LENGTH: 699 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:25:

| | | | | | |
|---|---|---|---|---|---|
|NGTCTTTGNA|CCTTNTCAAA|GATCGAGGCN|CCCCGAAATC|GTTGTGTCGG|GGCTGCGCCT|60
|TGGTGNCCNC|AGACNGNGTG|TCACGGCAGN|AGTCATGTCG|TCTAGCTCGA|GNAACACGGG|120
|TACCAACGTT|ANGAAGGATG|AGGAGNAGCG|GCGCCACGTG|TGTGTGAATG|TATTGGATCT|180
|GCCCCAGGAG|TCCATGGAAC|ACCCCGNGAC|CGGNACCATG|TTGTCCAAGT|ACGTCCGGAT|240
|GTCCAGCTTC|TTTACAGACA|AGTTTGCCTT|TAAGCTGGAC|TTACTGCGCA|TGTTGGCGGT|300
|AGCCAGAACC|CGTCGCTAGC|GGGCGTCTCC|TCGCTACAGT|AGATAGAGGA|AGCGCAGACG|360
|GTTAATNGTT|TCGGTTAACC|GATTTAGCCA|TCGATTGAAG|ATCTACGGCG|CACGGATCGT|420
|NGGATTTGAA|TNGCGTTTAC|AACATTTGA|GTTAGAGTC|NTCAATTGGN|GGGATTTGGN|480
|AAACTNCGAG|CTGGCGGNCN|NAGGGGAGAN|CGGCAATAAA|AACTTCCTCT|ACGANCGATA|540
|GCTTNACAGN|TTNCTNGCGG|AAANAGGTTC|GACCANCNTC|ACACGGAGGG|AGCTTTTNNT|600
|CCTTCCTCTN|NNAAAGCCTT|NAGNCCTCNA|TCNCCNNTA|NNTCGTATTT|CCANCACGAT|660
|ATCCGNNNCC|CCTNNACTCT|CNCTAATCCN|CCCCTNNNC| | |699

( 2 ) INFORMATION FOR SEQ ID NO:26:

( i ) SEQUENCE CHARACTERISTICS:
        ( A ) LENGTH: 553 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:26:

| | | | | | |
|---|---|---|---|---|---|
|GAGCTCACCA|AACGTTGCGG|AGACAGGTGG|GCGCTCGGGA|CTCACATCCA|CCGACTCATT|60
|GCGCTCTTGG|ATCACGACAA|CCATCGCGAA|CTGTGCAATG|TGCTGGTCGG|NCTGCTACAC|120
|CAAACACCCC|ACATGTGGGC|CCGTTCCATC|CGTCTTATCG|GCCGATTAAG|AAACTATCTA|180

```
CAACAGAAGT  TTCTCAATAT  CTTGGTGGAT  AGCGGANTCC  AGATCGATAG  TCTTTGTGAG      240

GGTTGTTACC  ACAGCGAAGC  GTACCGNTTG  NTGGTCCAGA  TCGAAAAAAA  CGAACTCCAC      300

GCCTAGNTCT  CTAGCCTGTG  CAAGNACCGN  NTTCACCTGT  CGGTGAAAAC  GAAANTGNAN      360

GGGACACCTG  TNCCGNCCGT  NTTTTAATN   AAATAATAAA  ATTGGTTCTC  ATNAATTTAN      420

ACGGNCTTAA  NTNTCCGNNT  TNGGGAAGGN  AAANTTTTNN  TTNTCCCCCC  AAACATTCCC      480

CCCCTTGGNC  CNNNNTNNNA  NCTNNACTTN  CNNNCGGCCN  TNTCCTNANN  AAANCNNATT      540

TTTTCNNNTN  CCC                                                             553
```

(2) INFORMATION FOR SEQ ID NO:27:

(i) SEQUENCE CHARACTERISTICS:
　　　　　(A) LENGTH: 560 base pairs
　　　　　(B) TYPE: nucleic acid
　　　　　(C) STRANDEDNESS: single
　　　　　(D) TOPOLOGY: linear (ix) FEATURE:
　　　　　(D) OTHER INFORMATION:
　　　　　　"N"represents any base.

(xi) SEQUENCE DESCRIPTION: SEQ ID NO:27:

```
GAGCTCGAAT  GAGATCACGA  TGATCCGTGG  NGTTCACCAC  GACAGGCCAT  TCCGAGTAAA      60

CCATGGAATC  CGATACCCCG  TAGGCCGAGT  CCAGAAACAC  CGAGGCGAAA  CTGAACCCCA      120

GCTCGCAGAT  CACGGNGTCG  CTGAGCATTA  AGTGGTCTTT  TTCCAGANTG  GTCAGCTTCT      180

GGGTCGTGTA  CCCGAAGTAC  TTCTTGTGCG  GAGNCAGCTT  GACGGACTGC  TGGNTGTCGN      240

TCACGAACTG  NTTCAGGGNC  GNTTCGATCA  AGCANCTTGG  GTCTCTGAGT  AAGGGNAGGG      300

GTTTGGCACC  ACGAANGTTN  TTNAACNATA  ATAGAANAGG  GTTTTCCGTT  CANCCCNAAG      360

GNAAGGTCNA  ATCCCCCGNN  GATTCCANGA  ANCGANNTTG  GGTTTTTCCA  GAGAAAAGTT      420

NANCCCNATT  CCNAAATCGG  CCTNNAAANA  ACAAAGAGGT  GGGNNGGGTN  AAANNNNNNA      480

NGNNNACCNN  TCGANTTCTC  CAANNNNNTT  TGNNCCCCCC  CNCCNNAGAA  GGGTTNANTT      540

NCCCNATTAT  TAATTTTNTT                                                      560
```

(2) INFORMATION FOR SEQ ID NO:28:

(i) SEQUENCE CHARACTERISTICS:
　　　　　(A) LENGTH: 694 base pairs
　　　　　(B) TYPE: nucleic acid
　　　　　(C) STRANDEDNESS: single
　　　　　(D) TOPOLOGY: linear (ix) FEATURE:
　　　　　(D) OTHER INFORMATION:
　　　　　　"N"represents any base.

(xi) SEQUENCE DESCRIPTION: SEQ ID NO:28:

```
NTNNTNNNNN  NNNNNGTTTT  NNAACTCTTA  AGCTCTACTA  CCCGCGGAGA  GACGNGTTCG      60

CGACGGAAAA  ATTCCGGTCC  CCTTTGTGGA  TCGCGATAGC  CTGTTGGCCA  ACGTTATTCC      120

CGTCGCCCCC  ACTCCCAATC  CGGAAACTGA  AGGANGACCG  GAGAAGAAAG  CACTGACACG      180

ACAGTGTTCG  CTCCCTACCC  CCCACCCTAA  GAAGCTCGGA  GTCCAGCCTG  ATTCCNATAG      240

CGACAGCGAT  ACGATTATCG  ATTAACTAT   GGAAGGCGCG  GGATCTCTGT  AGATTTGTTT      300

TTTGNTGAAT  TGTGCAACCC  GCATTGCTTG  GTGTCACTGT  AGACACGCCT  TCTGTCAATC      360

ACTAGTGTGC  TTTTGGTAAT  AAACGGNTNT  GGTTGGTATT  AGCCACGCAG  NNNGTGTGTC      420

TCATCTTCTT  GGCGGGTGAT  GGAGNGCCTA  CCCGCCTGTG  TNAAGGTTAA  TGGGNTTCAC      480
```

| AGTTNGGGAG | TGTGANTTTG | AGATTTTGTT | NAACCCNAAT | TGTTTATTGG | NTTAANTCAA | 540 |
| GNGTCCTTTN | TTNTTGGNNT | NTTNTANGNT | CTTTNATTNT | TNAATTCCNT | TNTNTTTTTT | 600 |
| ACGGTNNGGC | GGTTGGNNTC | NTNANTTNNA | ANNCCNNNGN | AAAANTNANN | ANAAANNNNN | 660 |
| NNNNTTNTNN | ACTTTNNTTC | ANCTGNANAA | TTTA | | | 694 |

( 2 ) INFORMATION FOR SEQ ID NO:29:

( i ) SEQUENCE CHARACTERISTICS:
        ( A ) LENGTH: 704 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:29:

| TGTTNNNNTG | TCCNTAAAAC | CCTTGAAGCT | CCGGGTNCCC | CGGATTTTAT | TGACGAGATC | 60 |
| GGAAGTTCTA | GAAGNNTCCA | CCACGCCCCC | AATTTCCTGA | ACCACGCCCA | TTTCGGATTG | 120 |
| CAAATCGGAG | AGCGGGGGCC | GCTGGGTAGA | AAACGGGGA | TGGGGAACCC | GCAATGCAAC | 180 |
| CCTATGGGAG | CAGGCCGTCG | AGNACCGTGG | GGGGAGGGGC | GGTNTANCNA | ACCCTGCCAT | 240 |
| GCACGCTGGT | GCGAGGTGGG | GGTTGGCCAC | TGNAAATGAN | TCTGGGGTCT | CCTGAATAGG | 300 |
| GGGATNGGC | TGNAGCCNCC | AACCCNNANT | NATTGGTGCA | TCATGGNGGA | TTNGNNACAC | 360 |
| AAACCACCTT | TNTTTTTTT | TTNTTNATTG | GANGTTTCTN | NCAACCANAT | NCCTNAACTT | 420 |
| CTTTNTTTGC | CCCAGNTTNC | TCNNGGNCCC | NNNTNTNTCC | NCCNTCNTTC | CTNNANTCCN | 480 |
| TNACCTGNGT | NTCTTNNNNT | TAAAANCCNN | TATCCCCNTC | NATCANNNGT | GGANTNGGNG | 540 |
| NNTNNNNCTT | NNGNTNNATN | NNCTCNTCCC | NNNNTTTNNT | NTTTCCTTN | NANTNATNCN | 600 |
| NTNNNNNTTT | NNTNTTTTTN | TTTNNTNCCN | CTTNNNNNCT | CTNNCNTTTN | TCNANTTCAN | 660 |
| ANCTTNTCNN | NNNTNCNTTN | TNNTCTTTNN | TNNNTNNNNT | TTCT | | 704 |

( 2 ) INFORMATION FOR SEQ ID NO:30:

( i ) SEQUENCE CHARACTERISTICS:
        ( A ) LENGTH: 727 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:30:

| TTTTTTTTTG | CNTTCTNAAA | GCAACNACAC | NCAAGGNAAC | ANAAGATGGA | GNTCCAGCGG | 60 |
| NGNATCGGCT | CGCGCGACCN | GTCGGAAGGT | TCGGAAGCCN | GGCGGNGTTC | AGGGAAACCG | 120 |
| ANTCNTTGGA | NNCCNANNTN | AGNCNCANNN | NTTNTTNNAT | NTANGNNGGA | GACANNAGNN | 180 |
| CNTCCCATNT | NGNANCATAT | NNTTANNTNN | NTCCANACNT | ACCCCANNAA | ANCGGTCNTT | 240 |
| TTTTTTTTT | TACANANNNT | ACTTAATTTA | AAAANCCTCA | ATANNNAANC | NANNTNNTCC | 300 |
| CANGNACCAN | NNCGCNNTAT | NNCNAANCTA | TCNNTTNCCN | NGNNNNGCTA | TNANCGACAT | 360 |
| CATNCATNAA | NTATNNAANC | NAAANNCATN | ATAGAGTTTT | NNTNANATTN | CNANNNCTAC | 420 |
| AGNNANTCAN | TCNGNNNTTA | ANCANAGNGG | NGGATATCTC | CNCAANCANN | NTANNAANTN | 480 |
| GACNCCTANN | TATANNTTNN | NNTNNTNTAA | TNCANNCTAN | CANATCNNNN | CNCTCTACAT | 540 |

```
TTNTACNNNA  ANACANATAN  NCAAANNNTN  TNNATNTATN  NNTCCNCCNA  NNTNATNANT         600

AATTGTNANT  ATNTACNAGT  GCTNTNCANA  ANGNTNANGC  NATCNNACTC  NCTACTTNAC         660

TTAATNNAAN  CACNNNANTT  NNTTCACTAT  NTTNNCNATA  ANTATATATA  NTCNNGNACN         720

NNTANCN                                                                       727
```

( 2 ) INFORMATION FOR SEQ ID NO:31:

( i ) SEQUENCE CHARACTERISTICS:
        ( A ) LENGTH: 542 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:31:

```
GAGCTCGGAC  CTGGTCTTCG  ATAGCAGGGA  ACTCATTATC  AGGAACATGA  GGGATCATTG          60

ACAACACCTC  ATCCTCCAAA  ACGTCCCCAT  TGGCCGNCAC  CTCATCCACA  GCAGTGGTAC         120

CAGTCGCGTC  CAAAATTGAG  GTGCTTTGAT  CGCAATCCAT  GTCCACCAAA  CCCATAACTT         180

TCTGAACTTC  ACACAGNGCC  ACTTGGTCCG  TAGAAAACTT  ATTCAGCAAC  ANCCTCCAGA         240

GTGTCGTCCT  CAGACATGGT  AATTTCGCCC  ACCACCAGTT  TCAAGATCA   TATNGTTCCA         300

GAGNCTNCAA  TANTCCCGTT  GCGCAATTCT  GATTCCTCCA  CCTCGGAGGT  GGGGNGCGCT         360

ANTCGGCTGG  CATTTATTCC  TCAAAGAAGT  NCNTGCAGNA  GNNGAAATTT  NATCTTGCAC         420

TNNCCNATCN  AGGNGGGTTC  AAGCTTGGAG  CAGNTTCTTC  GNNANTTCNT  TGTTCCTACC         480

GAAATTTCTT  AANAANCNTC  GNGCNCCNTC  CCAACNTACT  TATNTTATCN  TCGCNGTNNA         540

NC                                                                            542
```

( 2 ) INFORMATION FOR SEQ ID NO:32:

( i ) SEQUENCE CHARACTERISTICS:
        ( A ) LENGTH: 563 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:32:

```
GAGCTCTGCC  GGGGGTGTGG  AGGTGGACNG  TTTGACCGGC  TGCTCCGTGA  CTGATGGCCG          60

CAGCGGCGGC  CGACGGGTTA  GGATNTTGAC  GACCTAACAG  TTCAGTTATG  TGAGGAGGAT         120

GAGTGGTGAG  CGGTGAAATC  ATAGTNCACA  GGTACAGGCG  AGGGATATCG  CCGCAGCCGT         180

NTTTCCAGAA  CTCGTCAGCA  TCGGTGGCCA  CGAGATGCAG  AGTTAGTCGA  GGAAAGTCGA         240

GAAGATNNTT  TATTNTTNTN  GGGTCCCNNG  AGCGAAGGTA  CAGACCTNCA  TGGCGANCAG         300

ATAGTNGGNT  TNANNAGCCA  NNGCCAGAAG  TNGTTTCCGN  NNAATGNTAC  AAGGCACCTT         360

AACAAGACCC  GNCGCTTTTT  TNGGGNNAAA  GTNTGGCGNA  AGCNCAANNN  NCNNACCNAC         420

TNTCNNNGNA  TTTNAAANAC  NNNNGCTNTC  CNTCTNACTC  ANTCTNAACC  NATCCCNNCN         480

GGCTANNNNN  ACTNNNTCNT  CCCNNCCCTT  CTNTNANACC  CNNTNGGCNN  CCCTCCANAA         540

NNNCNTTCTC  NCTTAAANTN  CCG                                                   563
```

( 2 ) INFORMATION FOR SEQ ID NO:33:

( i ) SEQUENCE CHARACTERISTICS:
    ( A ) LENGTH: 696 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
        " N"represents any base.

( x i ) SEQUENCE DESCRIPTION: SEQ ID NO:33:

| | | | | | |
|---|---|---|---|---|---|
| NNTNTAGGGN | GTTTTNTNGN | NCGGGATNNN | NTAAGCCCNN | NTCTNTTTAG | GNATNNNGGC | 60
| CAGTCGTCAC | CNCNNTNCNN | GCNAAGNANT | AATGGGGGNG | NNGGGGGGGC | TANGGNATNT | 120
| NGAACNTCAN | NNGTGNACCN | CCANTCCNAG | TCAGCGANNG | CNAGTGANGA | GNCCACACAA | 180
| NANCGNNAGT | ANANCGACAT | CNATGNGTCT | ANCCTNACAN | GCNNCTTTTA | TCNNATCCAN | 240
| NNGTANATNN | NCAGAAGAGN | TNTCAANCAT | NTCGCTATA | NTNNCNGNAC | ATAATTCGAA | 300
| NNANNTCTCT | TCGNANNNNT | CGCTNNNNNG | GCNTNTNGTN | GAACTATAGN | CNNCNANNTN | 360
| CCTCNCNNAA | CTNGCTNNAA | TNANTTTTTT | NNTTTATTN | CNNNCTCCGA | CTCGANCNTC | 420
| CCCTNNGCNN | TTCNNNNNTN | NTNTNATTTT | NNNNCCACCC | NCTNGCCATN | TCCNACANCN | 480
| NCTCNTNNCN | NGCNCCNNNT | TTTNTCANAN | CNNNCTTNTN | NANAANTTCT | CTCCATTNTN | 540
| CNNCNCCCNT | TCNANTNTTC | CTATATCCNC | NNANANCAAT | AACTNNTTTN | TNANTTCACC | 600
| NTACTTTNNT | NGTATACTTA | AACNNTCCCA | CTCCNTCTCC | ANTTTNTNA | ANTCCNNCNC | 660
| CCNAATCNNC | CACCCNNTNC | NTTTTNNCT | TTTATA | | | 696

( 2 ) INFORMATION FOR SEQ ID NO:34:

( i ) SEQUENCE CHARACTERISTICS:
    ( A ) LENGTH: 742 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
        " N"represents any base.

( x i ) SEQUENCE DESCRIPTION: SEQ ID NO:34:

| | | | | | |
|---|---|---|---|---|---|
| GTTTGCAACT | CTGAAGCTCA | TAATCCCTCC | AAATCGGTAG | CGTGGCAGTA | GTAACGATGT | 60
| CGCCTATGGT | AGCATTCAGA | AAGTAGACGT | CGCTGGCAAA | GGTANGTTTT | CGCCTTTTGA | 120
| TTAGGACCAG | TAATNTCAGT | ATGTTGCTA | TGAGTCCGAC | GCATATGGNG | ATGCTATAGA | 180
| AACCGACGCT | GACATCGCGA | GATGCGTCGT | CGATCTTAAA | CACTTGCAGA | AGGTTACAGG | 240
| AGGAGTTGTT | CANGTTTGTA | AAAAGTCTGT | TCGCAAATCG | AACAATCTCG | ATTTGCAATG | 300
| TCGGGGTTNG | TGACCGGNCT | CAAACATATA | TCGGNTGGTN | GTGTCGTTGC | GCTATCAACG | 360
| CGCAATAATT | TAGAACGCGG | ATTCATATTC | CCTGGGCGGA | AGCTCTGGGG | GATCGTCCNT | 420
| TCANGCTATT | NGGGAGACAT | NAGCTTTTAC | AACGTTCCCC | AGCTTATGGN | ATGGTTGGGC | 480
| ACTCCCATTA | AACANTTCGG | AGGTACCCNC | CTATTGATNT | TACGACTTNA | CACATNTTCN | 540
| AACTTNATAG | GACTTAAGGA | CGGGTCTTTN | NNAACANAGA | NGGTTTTACC | CNCCCCCCCA | 600
| AAAAGTTTG | GTCGTTTCCA | ANTTTCCNA | ACTTTTCNGN | CGCGATCATC | NCCCCNNCNC | 660
| TCGAAGNTTT | ACGTTGGCAG | CCCNNGAAAA | NATGTAAAGC | CCNTTATNCN | CCACTNCCCC | 720
| CTCCNCTTNN | NNCTNCCCNN | CT | | | | 742

( 2 ) INFORMATION FOR SEQ ID NO:35:

( i ) SEQUENCE CHARACTERISTICS:
   ( A ) LENGTH: 1249 base pairs
   ( B ) TYPE: nucleic acid
   ( C ) STRANDEDNESS: single
   ( D ) TOPOLOGY: linear ( i x ) FEATURE:
   ( D ) OTHER INFORMATION:
       "N"represents any base.

( x i ) SEQUENCE DESCRIPTION: SEQ ID NO:35:

| | | | | | | |
|---|---|---|---|---|---|---|
| NNGAGCTCTG | CCGGGGGTGT | GGAGGTGGAC | NGTTTGACCG | GCTGCTCCGT | GACTGATGGC | 60 |
| CGCAGCGGCG | GCCGACGGGT | TAGGATNTTG | ACGACCTAAC | AGTTCAGTTA | TGTGAGGAGG | 120 |
| ATGAGTGGTG | AGCGGTGAAA | TCATAGTNCA | CAGGTACAGG | CGAGGGATAT | CGCCGCAGCC | 180 |
| GTNTTTCCAG | AACTCGTCAG | CATCGGTGGC | CACGAGATGC | AGAGTTAGTC | GAGGAAAGTC | 240 |
| GAGAAGATNN | TTTATTNTTN | TNGGGTCCCN | NGAGCGAAGG | TACAGACCTN | CATGGCGANC | 300 |
| AGATAGTNGG | NTTNANNAGC | CANNGCCAGA | AGTNGTTTCC | GNNNAATGNT | ACAAGGCACC | 360 |
| TTAACAAGAC | CCGNCGCTTT | TTTNGGGNNA | AAGTNTGGCG | NAAGCNCAAN | NNNCNNACCN | 420 |
| ACTNTCNNNG | NATTTNAAAN | ACNNNNGCTN | TCCNTCTNAC | TCANTCTNAA | CCNATCCCNN | 480 |
| CNGGCTANNN | NNACTNNNTC | NTCCCNNCCC | TTCTNTNANA | CCCNNTNGGC | NNCCCTCCAN | 540 |
| AANNNCNTTC | TCNCTTAAAN | TNCCGNNNTA | TNNNNTGTCT | TTATTCNCTT | CAAGGCCCCC | 600 |
| CTCCCAGGTA | GAGGTTTCGA | TAAGCTTGAT | ATCGAATGCC | CNCAGCCCGG | GGGATCCACT | 660 |
| AGTTCTAGAG | CGGCCGCCAC | CGNGGTGGAG | CTCCGTTTTC | GCAGCGAGTG | CGGCAGATGG | 720 |
| TAGCGATTCA | ACGTTCAGAT | CTGGATGAAT | TCACGTACCC | CTGTCAAGCT | CTTAAAAGGA | 780 |
| AAGGGATCGC | TGTACGTCAC | CAACCGTGAC | TGATGCACCA | AAGCTACCAG | GACGCGTTCC | 840 |
| GTAGGTCTTT | CTCGCGTCGA | TTGACTTCGT | CCGTTACGAG | GCAGTGGAGA | CGAGGGCCAG | 900 |
| GGTCTTCCTG | ATGGGTCGCT | GNCTCGNGCT | CCGNTGCCTC | GACACGAACG | AACTTGAGAC | 960 |
| TCGANGGACA | TAGGTCTTTN | TNNGGANCCG | TATTCGTAAG | GGGNGGAAGG | AACCAGNGTA | 1020 |
| TTGGNNATCT | TAGNTTCTTC | CCAGGCTTCC | CCTGATACGG | GTCCGGAAGG | CGNTCTTTTT | 1080 |
| AAANAAGAGC | CAGTCGGNGG | NNTTTTCTTT | AAAAAAGTTN | TGGNGGGGNT | CTTCCCNNNN | 1140 |
| NNNNGGGAGC | AANNNNNTTC | GNNGNGGGNN | ANCCATTTNN | NANNNCNNNC | CNNNNNGGNN | 1200 |
| NTTTTAATNN | NTTNCNACCN | NNTNNNNNNN | TAAGTNGGC | NCNNGGNTT | | 1249 |

( 2 ) INFORMATION FOR SEQ ID NO:36:

( i ) SEQUENCE CHARACTERISTICS:
   ( A ) LENGTH: 562 base pairs
   ( B ) TYPE: nucleic acid
   ( C ) STRANDEDNESS: single
   ( D ) TOPOLOGY: linear ( i x ) FEATURE:
   ( D ) OTHER INFORMATION:
       "N"represents any base.

( x i ) SEQUENCE DESCRIPTION: SEQ ID NO:36:

| | | | | | | |
|---|---|---|---|---|---|---|
| GAGCTCCGTT | TTCGCAGCGA | GTGCGGCAGA | TGGTAGCGAT | TCAACGTTCA | GATCTGGATG | 60 |
| AATTCACGTA | CCCCTGTCAA | GCTCTTAAAA | GGAAAGGGAT | CGCTGTACGT | CACCAACCGT | 120 |
| GACTGATGCA | CCAAAGCTAC | CAGGACGCGT | TCCGTAGGTC | TTTCTCGCGT | CGATTGACTT | 180 |
| CGTCCGTTAC | GAGGCAGTGG | AGACGAGGGC | CAGGGTCTTC | CTGATGGGTC | GCTGNCTCGN | 240 |
| GCTCCGNTGC | CTCGACACGA | ACGAACTTGA | GACTCGANGG | ACATAGGTCT | TTNTNNGGAN | 300 |

```
CCGTATTCGT  AAGGGGNGGA  AGGAACCAGN  GTATTGGNNA  TCTTAGNTTC  TTCCCAGGCT     360

TCCCCTGATA  CGGGTCCGGA  AGGCGNTCTT  TTTAAANAAG  AGCCAGTCGG  NGGNNTTTTC     420

TTTAAAAAAG  TTNTGGNGGG  GNTCTTCCCN  NNNNNNNGGG  AGCAANNNNN  TCGNNGNGG      480

GNNANCCATT  TNNNANNNCN  NNCCNNNNNG  GNNNTTTTAA  TNNNTTNCNA  CCNNNTNNNN     540

NNNTAAGTNN  GGCNCNNGGN  TT                                                 562
```

( 2 ) INFORMATION FOR SEQ ID NO:37:

( i ) SEQUENCE CHARACTERISTICS:
        ( A ) LENGTH: 622 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:37:

```
GAGCTCCGTT  TTCGCAGCGA  GTGCGGCANA  TGGTAGCGAT  TCAACGTTCA  GATCTGGATG      60

AATNCACGTA  CCCCTGTCAA  GCTCTTAAAA  GGAAAGGGAT  CGCTGTACGT  CACCAACCGT     120

GACTGATGCA  CCAAAGCTAC  CAGGACGCGT  TCCGTAGGTC  TTTCTCGCGT  CGATGACTTC     180

GTCGTTACGA  GGCAGTGGAG  ACGAGGGCCA  GTGTCTTCCT  GATGGCTCGC  TGNCTCGCGC     240

TCCGCTGCCT  CGACANCGAC  GGATCTGAGA  CTCGAGGGAC  ATAGGTCTTG  TTGCAACCNT     300

ATCGTAACGG  TGCAGCAACA  GCGTATTGGG  ATCTTAGCTT  CTCCCAGGNT  CCCTGATACG     360

GGTCGAAGGC  GTCTGTTAAA  CAGAGCCAGT  CGGNGNGTTT  TCTTTAAAAA  GTGCTGGCGG     420

NGCTCTTCCC  GNNCCGTAGG  GAGCAAAAAA  GTTCNTNGGG  GGGGATCCCA  NTGNNNATNC     480

GTCCNGGTNN  GGGAATNTNA  NTNNTNTTCC  ATCCGATTTN  TTCTTANGNT  CCGGCTCGAG     540

GGCCGNACCA  AATANTNANA  GCCCCCAAAA  ATTTNNTTTT  TNGCCCNCCC  ATTTGCATTG     600

NNCCCNTNGN  TTNCGGCCAC  CC                                                 622
```

( 2 ) INFORMATION FOR SEQ ID NO:38:

( i ) SEQUENCE CHARACTERISTICS:
        ( A ) LENGTH: 700 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:38:

```
ACCNNNTCNN  NANNATTTTT  NNNNAGNCNC  TTNANNTNCT  AAAGCNCATN  TANNCCTNAA      60

AAAAATTTAC  CGNGNGGNTC  TCACTCAGGC  CCCNGCCAAA  NAGGNTTTGG  TGTTTGCGCG     120

GCCGGTCGAG  CCCGATGTGG  CGGTGCCGGA  TNACGTNTCG  GTGTGGTGAC  GGTGCGGCCG     180

GAGAGGGGGA  GGAGNAGACA  GACNGNGANC  AGNGCGGTCG  NGGNCGGACN  GAGCCGAGNC     240

GTCTTNTTTT  NGGAGCNGCT  GTATNTCATG  NCCCGACANN  NCCGNNGGGA  NGNCTTCGGA     300

GCTACGGGTC  ANTTCNNCCA  CNACNTCATT  CNGTNGNCCT  NNNANTCNGT  NTGGGANATT     360

TATCCCCNGG  NTTAANNNAC  TNNGNCCCTT  TTTTTTTTT   TTTTTTTTT   TTTGCNNNGG     420

CCCCGCACNA  NNNCACNCGN  AGTTGNTNAG  CCCNNNNCCC  CANCNNCTCC  CTTNNTATNC     480

CTAACNCTCC  CGGATGGCCC  NTTTTNTTNT  CTCNCGCCGC  CTCTNTGCTN  CTTCTCACAT     540
```

5,753,488

63 64

-continued

| | | | | | |
|---|---|---|---|---|---|
| TANCATAACN | TCTACTTTNN | TAGCTTNGTC | TCCTTTNCNN | NTTTCTNTC | TNATAAANNN | 600 |
| NCNNNNCNTT | CNNNCTNTTN | NCNTTACNTT | NNCCNTGCTA | TCCNCCCNTN | NCCNNACCCN | 660 |
| TNNCAGTGGN | NNCNTCTCCN | NNACTTCTTN | NNCNATANTN | | | 700 |

( 2 ) INFORMATION FOR SEQ ID NO:39:

( i ) SEQUENCE CHARACTERISTICS:
        ( A ) LENGTH: 696 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:39:

| | | | | | |
|---|---|---|---|---|---|
| NNTNTAGGGN | GTTTTNTNGN | NCGGGATNNN | NTAAGCCCNN | NTCTNTTTAG | GNATNNNGGC | 60 |
| CAGTCGTCAC | CNCNNTNCNN | GCNAAGNANT | AATGGGGGNG | NNGGGGGGGC | TANGGNATNT | 120 |
| NGAACNTCAN | NNGTGNACCN | CCANTCCNAG | TCAGCGANNG | CNAGTGANGA | GNCCACACAA | 180 |
| NANCGNNAGT | ANANCGACAT | CNATGNGTCT | ANCCTNACAN | GCNNCTTTTA | TCNNATCCAN | 240 |
| NNGTANATNN | NCAGAAGAGN | TNTCAANCAT | NTNCGCTATA | NTNNCNGNAC | ATAATTCGAA | 300 |
| NNANNTCTCT | TCGNANNNNT | CGCTNNNNNG | GCNTNTNGTN | GAACTATAGN | CNNCNANNTN | 360 |
| CCTCNCNNAA | CTNGCTNNAA | TNANTTTTTT | NNTTTATTN | CNNNCTCCGA | CTCGANCNTC | 420 |
| CCCTNNGCNN | TTCNNNNNTN | NTNTNATTTT | NNNNCCACCC | NCTNGCCATN | TCCNACANCN | 480 |
| NCTCNTNNCN | NGCNCCNNNT | TTTNTCANAN | CNNNCTTNTN | NANAANTTCT | CTCCATTNTN | 540 |
| CNNCNCCCNT | TCNANTNTTC | CTATATCCNC | NNANANCAAT | AACTNNTTTN | TNANTTCACC | 600 |
| NTACTTTNNT | NGTATACTTA | AACNNTCCCA | CTCCNTCTCC | ANTTTNTNA | ANTCCNNCNC | 660 |
| CCNAATCNNC | CACCCNNTNC | NTTTTTNNCT | TTTATA | | | 696 |

( 2 ) INFORMATION FOR SEQ ID NO:40:

( i ) SEQUENCE CHARACTERISTICS:
        ( A ) LENGTH: 779 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:40:

| | | | | | |
|---|---|---|---|---|---|
| GGTTTNGNAA | CTCTTGAAGC | TCTCGNTCCC | CTAGAAACAA | GGCTCAGTAC | GTGGAAGGGG | 60 |
| TGTGGCNTCA | CGCCTACACA | CCTGGGCTGC | TCGACCATCA | TAACGTGTGT | GATCTGGAGG | 120 |
| GGNTTCTTTA | CCTGTTGTGC | TGCGGACCCC | GNAGTTTCTG | CTCGCGGNAC | ACGTGTTTCG | 180 |
| GGCGGGAGAA | GCACGGTTGA | CCATTCCCCG | CCCTGCTCCC | CAAGGATCTT | TTACGAGCCC | 240 |
| GNTCGCGATT | ATATGACGNA | TGTGAACCTG | GCTGAACTTC | TACGTTTATG | TGTGGNATCG | 300 |
| CGGCTATGAT | CGCCCTTCGA | CTTCGGATCC | NACGCCAGGG | GNTGATGACG | ACCGANCTNC | 360 |
| NGNCNGNCTT | TTAATAGANC | CGCCCTCNCN | TNCNCACCNN | TCTCAACAGG | ANNTTGCTTA | 420 |
| AAAGNCGTGA | TCCNANCGNC | NGCTTCTTNG | GCCGTCNCNA | TANTTCNCTC | TTCNACNTNC | 480 |
| CTNNCTTNNT | CCTNACANTC | TNNCTTCNTC | CNTCNNGCCT | CNNTGCACNN | CNTATTTCTT | 540 |
| CTNCATCTNT | TTANCCTCCC | NTCNNANTTT | NNNTTNNCNA | TCACTCCANN | CACNNCCNNN | 600 |

| | | | | | |
|---|---|---|---|---|---|
| TNTTANCCCC | CANNTCCCCC | CCCATTNTTN | NCANCTNCTC | CNCTGCCAAN | NNCCTNNTTT | 660
| TTANCCCCNT | CTNNCCATNT | TTTNCTTNGC | TTCNCNTANA | TCCANANTCC | CCCTNNACCT | 720
| TACANCTCTN | TATCCTCTNA | TCCCTCCNAC | TATACCCCTT | NTTNTATCNT | NTCCNCCCC | 779

( 2 ) INFORMATION FOR SEQ ID NO:41:

( i ) SEQUENCE CHARACTERISTICS:
        ( A ) LENGTH: 558 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:41:

| | | | | | |
|---|---|---|---|---|---|
| GAGCTCGTCT | TGCAGCAGAT | TGCGGGTGGA | ATACACGTNT | TCGCTCACAT | CGCACAGCTG | 60
| CGTCTTTTGA | CTGCTGACGG | GTTTGACAAC | AGAACCCAGG | GGTGAGAAGC | AANAACGACG | 120
| CGAGCAGCGA | AACCAAAAAG | AGCCCTGCCT | AATGAATCCC | CGCAAAGTCT | CGGCGAGTTT | 180
| GAGCATCACG | GTCCCGTNAA | TTAAAACGTG | TACGCAACCG | NNTGATNTCC | ATGAACACGG | 240
| CCCTGTTAAC | AAGGCTCCAA | CCAGCCAATC | ACCGNGTACT | TGGNCTTNCT | CCAAAAATGC | 300
| CAATAACGAG | GNNGGGNTAG | CCTCGNNNGG | GNCTCTTNCA | ACGGTNCGAG | GGATCCCGNN | 360
| AGTTGAAANN | TGNATNANGG | GCCNTTCCCC | CCCAGGNNNA | ACCTTGGNCC | CCANNNTTTN | 420
| GNTNNANANN | AANNGGACCN | NCGNCTGGGT | ACCCCNNCAA | GANCTTTNAA | ANTTNCCCNC | 480
| CCANNTNGGA | AAANTGTNNT | TNTNCCAANN | NTTTCAAAA | NTTCNNCCAA | ANCGNNNNNC | 540
| CNNTTNNTTG | CAANNAAA | | | | | 558

( 2 ) INFORMATION FOR SEQ ID NO:42:

( i ) SEQUENCE CHARACTERISTICS:
        ( A ) LENGTH: 670 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:42:

| | | | | | |
|---|---|---|---|---|---|
| TTTTGANACT | TNTTAAGCTC | GATGACACCN | TGANCTGATN | GCGACAAACC | AGGAGCGGCT | 60
| ACANCCACCG | AAGACGATTT | ACGCGCGCGC | GATGCACAAG | CTCTTGGGCT | ACCGCCCAAC | 120
| GCCGGCTGCA | ATGCCCCTCT | GAGCGACCTG | GNTCAGCTGA | GTCGTGCTCT | ACGTTGCGAT | 180
| TGGCGATACT | GGCGACTCAC | TACTGNCCCG | GAAGAATNNG | NTGATCCCGG | CGAAGACGAT | 240
| TCTTATAACG | AGTTACCATA | CCGTACGTGG | GCCCCACCG | ACTATANCC | TCAGNGGGAN | 300
| CCACAGACCG | CATTCGGGGC | AANCACAACC | NTCGCTCGTC | GNTTGTCTCA | TCACCGAGCC | 360
| ANTGCCNTTT | TGTTCCCTAC | GGCGTCCCTT | GGCCCTTNNA | GNCCNTCGAT | CNNNGTTGNN | 420
| NGNCANTTTT | TCCCNTCTCN | AGTACCCNNN | GGNGGTGNTT | NGNCNNTTCC | TNTNNNACGA | 480
| TTTTNNNAGT | NNNNCCANAT | TCTTCAGNNT | CCCTCTCANT | CNCNTCTNNG | NANTNTCNCC | 540
| CCNANTCTGT | TTTTTCTTTN | GTNNATTTNT | TNNTNAATTT | TCTTTCTNNN | TCCCCCTNAN | 600
| NACCNTNNNC | NTTNTTCTNT | TCTTCTNCNC | NNNTCTCCNN | CNNTNTTNNT | CNTNTTNNTN | 660
| NTNTNCNNTT | | | | | | 670

( 2 ) INFORMATION FOR SEQ ID NO:43:

( i ) SEQUENCE CHARACTERISTICS:
        ( A ) LENGTH: 545 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:43:

```
GAGCTCTCCG AAAGCTGGAT GNACGNGAGT CTGGTGAACT GGATCTACAG GTTTCGCTGC    60
ATCGTTTCAA TTTACAGAAA TATTCTCTTC GAACTCGCCG GCACCTTCAG CACTTGNGTG   120
CTTCTCTGGT TTAGTTTCCC AACAGTTGAA ATGTGTCTGC TGTGCACTGT CCCGACGGGA   180
GCCATATTAA TTCCCACCCT GTGCCTCGGA ATAGCCTGTT GNTGTCAGAA AGAGATGNTG   240
CGATACTCGG GATCCTCTAC GCTCGNTTGT GTNTTAATTG ACACTTCAAT AACAAGTTAT   300
GACCGGTTTC TTGTNGTCCN GGGNAAAAAC CTCAACCTCG GGAATNGGCT TGAGGTNGGG   360
TGATGATCCN NTATTTTTNA CNCCCTNGGA ATTNANGCCN NCCNNAAGAA AGGCCCTTGN   420
NAATTTCCC NTCCCNAAGG GGGGGGCCCN NCCCCTTTTT NTTNCTTTNN CCNGGNTNGG    480
GCAAAGGGGC CANCANTTAA AATTTTCCAC CNNNTTCTC CTTCCTANAA GGGGGTTNAA    540
TTNTT                                                              545
```

( 2 ) INFORMATION FOR SEQ ID NO:44:

( i ) SEQUENCE CHARACTERISTICS:
        ( A ) LENGTH: 688 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:44:

```
NCNNTTTTNN NTGTTCTTCT ACTCTGAAGC TCGAGATCNC ACCGATGCAT TNGNCGTGAT    60
GGAGATCCAG GCACACCGTA TCNATGTTCA CGGTAAAAAG CAGNCCCATG AACTCGTNCT   120
GAATGTTCTT GGACGATTTC CAGACGTGAC TGTCCGTTCA AGTAATTGTC CGGCAGGGTT   180
CCCTTGAACT GCGCGGTATA GCGAGTCATC TTCTTGTGAC CGTGACAAGT GACTCTNTTG   240
NTTGTCCACG TAAGCTGTTC CGCGTGGACG ATTAAGTGGT CGTCCTGACG GGTGAGGGTG   300
GNCTTGTCAA ACGGCACTTC TTCGATCCAA CAGTAGNNAA NGTNGNCGGT CAGGGTTAGG   360
AAAGGCAACT CCNTGTNTTN TNTTTATNNC CNNNCNGCTA ACGATNANGN NTNAACCCTT   420
ATCTNTTTTG CNCCANNNNN CCCCCNTCTT CTNCNCNNNT NANANNNNC CNCGGNCNTC    480
TTCNTCCNGG NGNCCCCNCA NCNTNNCCCN CNCTANNCNN GCCNCCTTCN NCNANTNNCT   540
TCTCTNCTNC TTNCCCCCCA NCTCCCTTTT CTCTCNANNC CNCNCNCCNC NCTNTNCCTC   600
NTANNNCTTC NCNNNNTCAC CNCTNTCNCC NNCTTTNCCN ANCCCCCCCT CCTTTCCCCC   660
TNCNTCCTTA TCTTNTNTTT TCANNTCN                                     688
```

( 2 ) INFORMATION FOR SEQ ID NO:45:

( i ) SEQUENCE CHARACTERISTICS:
        ( A ) LENGTH: 670 base pairs
        ( B ) TYPE: nucleic acid (C) STRANDEDNESS: single
(D) TOPOLOGY: linear (ix) FEATURE:
    (D) OTHER INFORMATION:
        "N"represents any base.

(xi) SEQUENCE DESCRIPTION: SEQ ID NO:45:

| | | | | | |
|---|---|---|---|---|---|
| TTTGANACT | TNTTAAGCTC | GATGACACCN | TGANCTGATN | GCGACAAACC | AGGAGCGGCT | 60
| ACANCCACCG | AAGACGATTT | ACGCGCGCGC | GATGCACAAG | CTCTTGGGCT | ACCGCCCAAC | 120
| GCCGGCTGCA | ATGCCCTCT | GAGCGACCTG | GNTCAGCTGA | GTCGTGCTCT | ACGTTGCGAT | 180
| TGGCGATACT | GGCGACTCAC | TACTGNCCCG | GAAGAATNGG | NTGATCCCGG | CGAAGACGAT | 240
| TCTTATAACG | AGTTACCATA | CCGTACGTGG | GCCCCCACCG | ACTATANNCC | TCAGNGGGAN | 300
| CCACAGACCG | CATTCGGGGC | AANCACAACC | NTCGCTCGTC | GNTTGTCTCA | TCACCGAGCC | 360
| ANTGCCNTTT | TGTTCCCTAC | GGCGTCCCTT | GGCCCTTNNA | GNCCNTCGAT | CNNNGTTGNN | 420
| NGNCANTTTT | TCCCNTCTCN | AGTACCCNNN | GGNGGTGNTT | NGNCNNTTCC | TNTNNNACGA | 480
| TTTTNNNAGT | NNNNCCANAT | TCTTCAGNNT | CCCTCTCANT | CNCNTCTNNG | NANTNTCNCC | 540
| CCNANTCTGT | TTTTTCTTTN | GTNNATTTNT | TNNTNAATTT | TCTTTCTNNN | TCCCCCTNAN | 600
| NACCNTNNNC | NTNTTCTNT | TCTTCTNCNC | NNNTCTCCNN | CNNTNTTNNT | CNTNTTNNTN | 660
| NTNTNCNNTT | | | | | | 670

(2) INFORMATION FOR SEQ ID NO:46:

(i) SEQUENCE CHARACTERISTICS:
        (A) LENGTH: 688 base pairs
        (B) TYPE: nucleic acid
        (C) STRANDEDNESS: single
        (D) TOPOLOGY: linear (ix) FEATURE:
        (D) OTHER INFORMATION:
            "N"represents any base.

(xi) SEQUENCE DESCRIPTION: SEQ ID NO:46:

| | | | | | |
|---|---|---|---|---|---|
| CNNNNTGTNN | NNNGTCCTTA | ACNCTTAAGC | TCCTTGACCC | CAGNNACGGT | GTCCACGGGC | 60
| AGCAGGAATT | TGTCACNGCA | AAGGTATTTC | TTCTCCAAAT | CTCTAATATT | GAGATGGCCA | 120
| AAAGCTCCG | CGCGAAGAAA | ATCAGAAAAG | GTAAAATACC | ATCCAGGAGG | CCAAGCGATA | 180
| GGAAAAGTTT | CCCCGTTCAC | CTTCCGAACA | AACTTCATCA | GACGCTTAGG | CGCGTCCTTG | 240
| GTGCTCACGG | AGCAGTTAAA | AAATTCACGG | ACAAGCAATT | CGTGACGCTT | CATGTCGGAA | 300
| ACAATCATGA | TGGACGGGGT | TACCAGTGTG | GAACGAAGTC | GGGCACGCCC | GGGCTCGCAG | 360
| GAAATAGATA | TAGCTCGTGC | CAACCCACAA | AAATCTGCAT | CTGCGTCAAT | ATTTTTAGG | 420
| GTACAACTTT | CTTGCTTTTT | NGGGTTGCTA | GGGTNCGGAA | TTCCGNAATT | GGANAGATNC | 480
| GTCGNTTTGT | CCGNNCTTCT | TCCTNGGGNN | NNCGNTAAAG | GTANTNAGAN | TTTTNTNTCC | 540
| CGGGGNNTNG | GGAACCCCCC | TGGGNTTTTT | AANNTATTGG | NCNNACTTTG | TGTTNACCN | 600
| NCCTTNNCNG | GNNNNNNGGG | GNCGTTTCCN | NNGGNTNTNN | CGNNGGCAT | CCNTGNNTT | 660
| GGNNCCCNNG | NTNGGGGGN | NTTCNTTN | | | | 688

(2) INFORMATION FOR SEQ ID NO:47:

(i) SEQUENCE CHARACTERISTICS:
        (A) LENGTH: 542 base pairs
        (B) TYPE: nucleic acid
        (C) STRANDEDNESS: single
        (D) TOPOLOGY: linear (ix) FEATURE:
    (D) OTHER INFORMATION:
        "N"represents any base.

(xi) SEQUENCE DESCRIPTION: SEQ ID NO:47:

| | | | | | |
|---|---|---|---|---|---|
| GAGCTCTAAA | GTATAANTAA | CTTTTNAGGA | CCCTGACCCT | GTTCAAATGG | AGCCAACAGG | 60 |
| ATGACACATA | AAGTTATTCC | ACTGATGGGA | AATTTAGTCT | ATTAGAGCAG | TGGTTCTCAG | 120 |
| ACTTCTACAT | TTCATGANCA | GAACAACAAC | AATAATAAAT | GGAGAACTTA | CATGGGATTA | 180 |
| ACAATTTTAC | CACCTACCTT | TTGGTCAGCT | CACTGAAAAA | AAAAGAAACT | GAACAGCAAG | 240 |
| GAAAGAACAG | NTTACTGCCA | CAACTGCCTT | TCTTGTATTC | CATTTNGNTA | CAGACTGGTT | 300 |
| AANAAAAAAA | AAAAAANGTC | ACANNTTGGG | NAACANTCCA | CAGACCCATT | NTTGGGGAAA | 360 |
| AAATGGGTTA | GAGAGTTTTT | TANGGGCCCT | NCTTATTTTT | NAAANTNGGA | CGNCTTTAAN | 420 |
| TCATNTTTTG | GGGGNCNTNA | CNATGCCNNC | CTTAANTTTN | NGNTTACATC | TTGNANGNTT | 480 |
| CTCAANGCCA | ANAATNTTTN | ANTNCCCTNC | NATTNAANCA | ATTNTGCCCA | ATTCCCCTNT | 540 |
| TT | | | | | | 542 |

(2) INFORMATION FOR SEQ ID NO:48:

(i) SEQUENCE CHARACTERISTICS:
      (A) LENGTH: 676 base pairs
      (B) TYPE: nucleic acid
      (C) STRANDEDNESS: single
      (D) TOPOLOGY: linear (ix) FEATURE:
      (D) OTHER INFORMATION:
          "N"represents any base.

(xi) SEQUENCE DESCRIPTION: SEQ ID NO:48:

| | | | | | |
|---|---|---|---|---|---|
| TNGGNAACTC | TCAAGCTCCC | CACCCCATTG | ANAAATATAT | TAACATCACG | TCATCTACTA | 60 |
| ANCCCCATTC | AAGTTGTGGT | CTATGGATCA | ATATCGGCAT | CACTGGGGAG | CTTGTAGGAA | 120 |
| ATGCAGACTT | TCAAGNTCGA | TCCCAGATCT | GCTGCTGAAT | CAGAAGCCGC | ACTTTCACAA | 180 |
| CATCCTAAGT | GATTCGTTTG | NACACTGCAG | TTTAAGAAGC | ACCCCACATT | TTGTTGGATA | 240 |
| TTCAAAANAA | TGAGAACCTG | ACTTTAGGGT | CTCCTCTCTC | CCACCCTACC | ACTACCTCCA | 300 |
| GCAGTCTCCT | TGTCTTCCAG | ATTCCACCTT | AAAATTCAGG | AATCACCATG | CACTGAGGAC | 360 |
| AGGCCTGCAC | AAACATCTAG | TTCCCCATGC | TTTAGGAAAA | GTGACAAAAA | CCCACAACCG | 420 |
| CCTTCCCTTT | CCCAGGGTCC | CTCCTGCCCC | CAGGAAAAAT | AGGAANTTCC | CTCAAATCTT | 480 |
| CCCCCAANGG | CCGGGTGNAG | GNGGGTCAAA | ACCTGGTAAT | CCCAGGACTT | NGGGAGGGTT | 540 |
| TGANGCAGGA | GGGGTCAACC | NNAGGNCAGG | GNGTCNAAGN | CCAGGCCCGG | CCGAATGGGN | 600 |
| NAAACCCCNC | CTTTCNAANN | GTCAANANTT | GTGGNGGGGN | NNNNNGNCCN | NNNGNCCCNN | 660 |
| TTTTCGGGNG | GTTGTT | | | | | 676 |

(2) INFORMATION FOR SEQ ID NO:49:

(i) SEQUENCE CHARACTERISTICS:
      (A) LENGTH: 698 base pairs
      (B) TYPE: nucleic acid
      (C) STRANDEDNESS: single
      (D) TOPOLOGY: linear (ix) FEATURE:
      (D) OTHER INFORMATION:
          "N"represents any base.

(xi) SEQUENCE DESCRIPTION: SEQ ID NO:49:

| | | | | | |
|---|---|---|---|---|---|
| NGNCTTANAA | TTNNNNNATA | GCCTTAAAGC | NTNCTAAACT | AGTTTGGNAA | NTCATTATCA | 60
| GGGAACNTNC | CGNTTCANNG | ACAACACCTC | ATCCTCCANA | ACGTCCCCAT | GGGNCGTCAC | 120
| CTCATCCACA | GNAGTGGCAC | CAGNCGCGTC | CAAAATGGAG | GTGGTTTGNT | CGGAATCCAN | 180
| GTCCACCAAG | CCGATAACTT | NCTGAACTTC | ACACAGNGNC | ACTTGNTNCN | NNGAAAACTT | 240
| ATTCAGCAAC | ACCTCCAGAG | TGTCGTCCNC | AGACATGGNA | NACTCGNCCA | CCACCAGTTT | 300
| CAAGATCATN | NCGTCCAGAG | CCTGNATAAT | CCGCTGCGAC | TTCTGATTCT | CCACCTCGGC | 360
| GGCGGGGTGN | NTTTGTGGTT | GGNANTTATC | CGANANGAAG | TCCTGCNAGC | AGGACGACAT | 420
| CTTCATCTTG | GNANCTGCCG | NTTNNAGNGG | GATCAGNTTG | GAGCAGGNTG | CTTTCGNTCA | 480
| CTTCCTGGAT | CCCTTCGCNA | TNNGTNTTAN | TTTTCCTNCG | GCTGTTGATC | NCTTNNGTTC | 540
| TGAAGTTTTT | CCTCGCAGGA | AGCAGTGAAT | CTTNTNGAAT | CNTNCATTTT | CTNNGCTAGG | 600
| NNTGTANCAA | GGANATTNCN | CNATTTCTTC | GATTCTCNTC | NTNCNNAATN | TNNNATNTTC | 660
| ATANTAGNNT | CNGNCAAGGN | TNNTTCNCCN | TCGTAANG | | | 698

( 2 ) INFORMATION FOR SEQ ID NO:50:

( i ) SEQUENCE CHARACTERISTICS:
        ( A ) LENGTH: 610 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:50:

| | | | | | |
|---|---|---|---|---|---|
| GAGCTCCAGA | GGAGATNGGC | TCGCGGGNGC | GGTCGGGAGG | NTCGGAAGCC | TGGGGGNGAC | 60
| CAGGGAANCN | ANGCCGTGNA | NCCCGCNATA | GGNCGCGGAC | TGGTTTTTTT | TTTNNTTNAT | 120
| GNGGTGCNCG | GACNCAGGGN | CCNGTTCGGN | TCGCAGACTC | NAATAGNNCN | CNATTCANCC | 180
| TNGCCTNANN | ATTCANGTAA | ACCCCACNNN | TTTNTAANAA | ANNGCCTANG | TCCCNNCTGN | 240
| TAANACGCCC | CCCCGCCTTT | TNTTTTTTN | TTTTTTTTT | TTTAATNCCC | NACNCNNAAC | 300
| NGAAANCTCN | AAANTTTCNT | TNCAAANTNA | TNANNCTNTT | NNANATANTT | NTNTCTNACT | 360
| ANNTACTCNN | NCNAANAATA | ATTNTAAAAT | AANCNATATA | NTNANAATAA | AATTATATAA | 420
| NNATNTCCNC | CTAAATTTCC | NTCTTTATAT | ACACTCCANA | TNAANTNAAN | NTTTATCTTT | 480
| CTATTATNTN | ACTACANCAA | NATNNTCATA | ATAATATTCA | ACTNCTNATC | ATTNTACATN | 540
| CTCTATATCA | TNANCNNANA | CAANTCNTAT | TATANNCNNA | NTACAATACA | TTNTTTTNTA | 600
| TAAAATATTT | | | | | | 610

( 2 ) INFORMATION FOR SEQ ID NO:51:

( i ) SEQUENCE CHARACTERISTICS:
        ( A ) LENGTH: 586 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:51:

| | | | | | |
|---|---|---|---|---|---|
| GAGCTCGTCC | CTTGCGTACA | AGACAGCTGG | TTCGTGATGT | TCGCAATAAT | GACGGAGCTG | 60
| AGCCGTGAAC | ACCAGCTGAT | TGAACAGAGT | GCAGACGTGC | GAGATGGTGG | TTTGGATCTG | 120

| | | | | | | |
|---|---|---|---|---|---|---|
|CCCGCCGGCT|AGCGGCGGGT|CTTGAGTGTG|CGGTTGCAGT|CGACACTTTA|TATTTTNTGT|180|
|AACGTTCACG|ATCTCTGATG|AATCAACTCG|CGTGCGAGTT|CGTTTAACT|GTATGATGCC|240|
|TTGGATGGAA|CTTTCGATAG|TCCCGGTCGT|TATAAAATAT|AAATAAATTA|CTGTTGGGGC|300|
|GAGTGCAGCC|GAAAGTGGNA|GGCAGGTTGC|GAATAAGCAG|TTTCTTCTTA|CCTTCCGCGC|360|
|GAATCGGACT|CCGGTAAGCT|TTAGAAAGGT|TATTGGACGN|NNGGTTTGNN|GTCCCCGNGC|420|
|TCTCTTTACG|GTTCCGCATG|GAGAATCGNG|NNNCGGTATA|TATTTTCANA|GGCATGGGAN|480|
|GCGGTNTCNN|CNNGGAAAAG|GCTAACGGGG|GNTCCANNGG|GTTGCCNNCG|GTTCNATANC|540|
|CNNNCCCCAC|CACGTGGCCN|ATCCAAANNA|CAATNCTNAA|ANCACT||586|

(2) INFORMATION FOR SEQ ID NO:52:

(i) SEQUENCE CHARACTERISTICS:
        (A) LENGTH: 673 base pairs
        (B) TYPE: nucleic acid
        (C) STRANDEDNESS: single
        (D) TOPOLOGY: linear (ix) FEATURE:
        (D) OTHER INFORMATION:
          "N"represents any base.

(xi) SEQUENCE DESCRIPTION: SEQ ID NO:52:

| | | | | | | |
|---|---|---|---|---|---|---|
|TNATTTGAAG|TCNNNNNATA|CNCTANAGCN|TTNNAAACTA|CATNATCGAT|ATTGAGGCCG|60|
|ATATTNCCCT|TCTNGGAAAG|AGCTGNGAGC|GCTTNCACTT|TTGGCAGANG|CTCGTCCATG|120|
|ACGCGCNCGC|TCTGCGCGGG|AGCATAACGC|GGGTGCAGTG|CCGAAAGCTT|GATTGAAATA|180|
|CCCGGGNCAT|CATAGATGCC|GCGACCGGCC|GACGCGCGAT|CANTCGNGTN|GATCGGANCC|240|
|TCATAATCCT|TGTAATAGCG|TTCTGCATCA|GNCGNCGNGG|TNGGCTGGGT|TCACCCAGCA|300|
|TATCATAGGA|GTGGCGGAAG|NCGNGTTCTT|CAAGCGACTT|TGNACGNTTG|GANTGCTNCA|360|
|TCANTGGTTT|NNNTNATTTT|AAGAGACTGN|TCGGCCGTCA|GGNGCATNGC|CAATATCCAC|420|
|GNCACGANGG|GTAACCCCNN|TTCAANCNCA|AGGGAGCAAT|NGAAGGCGCN|TNCANTTNCT|480|
|TCCGNACAGG|GCNNNTCNNC|ATTAANGNNN|NTTCCNNCAA|NTTGACNNNT|GNNCAAAAAN|540|
|GNCCCANCCC|NNTNGAATCA|GGNCAAANNA|AACGGNCACG|GGGGAANTTN|TAANTNCCNN|600|
|TNNCCCTCCC|NNNTNTTTTC|ATNTCNAAAG|CATNCNAANN|NNNNNTCCTT|TCCNNCTGGN|660|
|NNCCCCNATC|ATG||||||673|

(2) INFORMATION FOR SEQ ID NO:53:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ix) FEATURE:
        (D) OTHER INFORMATION:
          "N"represents any base.

(xi) SEQUENCE DESCRIPTION: SEQ ID NO:53:

| | | | | | | |
|---|---|---|---|---|---|---|
|GTTTTGCACA|CTCNTGAAGC|TCCCACTGCC|ATCGAGTGGN|GGATAACAAA|CTAACAGCCA|60|
|GANACATGCC|ACGATCATTT|GTATTTATT|TATTGTTGGA|AAATCANCAA|CAGTGTACTC|120|
|TGCAGTTCAA|TCGTAACCCC|TGCTTATTTT|TCAGCGGTGA|CGGTCTGAAC|AGTCCGCTTC|180|
|TACACGAGCC|CAACCCCTTT|CACCTAACAG|TCCACGCTCC|CTACGACATT|AACTTCGGTC|240|
|ACCACTCCAG|NCAGACGGTG|GAGATAGACA|TCCGCTACGT|ACAGACTGGC|GGCCGCTGCT|300|

```
TTTTGGTCGN  CAACCTGCCA  CACGAAGACT  CGTTCTACAC  CGGGATGTGT  CTGTGGCGAA    360

CAGAGGCACT  GAAGATCACC  CTCTGGTCCC  GGNTGCGCAC  TACCATTATC  CCTCAGGGNA    420

TCCCTATCGC  CGCGTTGGTA  TCAAATCAAC  GACATCGACG  GCAATCTTNA  CGCGTATAAC    480

CATAACACGG  TTTTCCCGNA  NAGTTCATCA  TNNCCGACAG  GAACANCCTT  CTTCCCTTAG    540

GGATTTTAAG  CTCCCCACCA  ATAGTTTCCC  TAACCTCATC  CTANGGGCAA  TTATTCCNCA    600

TCTNAGGGGN  ATCTTCCTTA  ATTNTCTTT   ATGGATAATG  GTAGNCNGGG  GNCCNTCCGT    660

CTTCTAGTGG  GGNTGANCCC  CAANTGGCG   GGGTANCATN  CNGTTTTNGG  TTGACCTGGT    720
```

(2) INFORMATION FOR SEQ ID NO:54:

(i) SEQUENCE CHARACTERISTICS:
        (A) LENGTH: 632 base pairs
        (B) TYPE: nucleic acid
        (C) STRANDEDNESS: single
        (D) TOPOLOGY: linear (ix) FEATURE:
        (D) OTHER INFORMATION:
          "N"represents any base.

(xi) SEQUENCE DESCRIPTION: SEQ ID NO:54:

```
CTGNCACCCG  TNAAGCTCAN  TTACCACTTC  TTGGGAGGAG  GAAATAGATT  TTATCTATCT     60

NTGGAGCAAT  ATTTAAAGTT  TAGAATTCTT  TTGTTTTCAT  ATATCATTTG  CATCAACTAA    120

TGGAGAGTTA  AAATGAGAAC  CCCTACTACC  TGCCAACATC  ACTGCTCTGT  GGTGACTATG    180

AAACGAGTAA  GAGAAACCAT  AGATGCATTT  TGACCTTGTG  TCTGCCTTGC  ACTGCTCCTG    240

TATCCAGCTC  TACTTGGAGT  TTAATATTGA  CTCTTAAGAG  GACAAATTAN  TTANTGTAAT    300

AGTACATNGA  AAATGTAAAA  CACACANCAC  CACNCANNNG  CCTNCTCAGC  ATTGGCCTCA    360

TTCCCATTTT  TCCTCTGTGA  CCCTGTGATA  GACATTAGAG  GTTTCTGCCT  TTCAGAAGCT    420

TCTNCCCTCC  CNCNCTCGGA  GATGGAGTCT  CACTTTGNTT  GNCCAGNCTG  GAGTGCAGTG    480

GTGTGATCTC  GGNTCACTGN  AACCACCGNC  TCCCAGGTCA  AGCAATTCTC  CCTGTCTTAG    540

CCTCCCGAGT  NNTGGGATAC  AGGCANACGC  CACACGCCCA  GGTAATTNGG  GTTTTANGNN    600

GAGNTGGANT  CCACCAATTG  GCAGCTGGTC  TT                                     632
```

(2) INFORMATION FOR SEQ ID NO:55:

(i) SEQUENCE CHARACTERISTICS:
        (A) LENGTH: 517 base pairs
        (B) TYPE: nucleic acid
        (C) STRANDEDNESS: single
        (D) TOPOLOGY: linear (ix) FEATURE:
        (D) OTHER INFORMATION:
          "N"represents any base.

(xi) SEQUENCE DESCRIPTION: SEQ ID NO:55:

```
GAGCTCCCGA  CCTCAGTTGA  TCCATCCGNC  TCTCAGTCTC  CCAAAGTGTT  GGGATTACAG     60

GCGTGAGCCA  CTGTACCCGG  CCAAGAAGTG  TTTATAAAAT  TGTTGAAAAA  TCTGCTGTTT    120

GTGGGAGCTT  NTACTCAGGC  ATTCTAAACT  GCTTACCGGT  GTCTTTTGG   CCAGTATCGT    180

GGATTGCCTA  CTTGAACAAG  ACTNGTAGGG  GAAGCAGATG  GTCTTGTCAC  TGGCCATGAG    240

CTGCTTACCA  TATATTGAGG  AGCCACATTC  ANCTAACTGN  TTTCCGAGCG  ATCATGGAAG    300

TTTCTATTAG  CAGCCTGCAG  TACATCAGAG  AAATGATAGC  TTTNCTTTTN  TTNTCNTCAA    360

CTTNAACGTN  CTGGGATACA  CGTCTTGAAC  ATGNAGGTTT  GGTACANAGG  TTTTCATATG    420
```

| CATGGAAGTT | TGTTNGNTGG | CCCTATCAAC | CACCATTTNG | GTTAAGCCN | NCATCNTAGG | 480 |
| AGGTGCCCAA | TNCCTCCCCC | CTTTCCCCCT | ACCCCAA | | | 517 |

(2) INFORMATION FOR SEQ ID NO:56:

(i) SEQUENCE CHARACTERISTICS:
        (A) LENGTH: 685 base pairs
        (B) TYPE: nucleic acid
        (C) STRANDEDNESS: single
        (D) TOPOLOGY: linear (ix) FEATURE:
        (D) OTHER INFORMATION:
          "N" represents any base.

(xi) SEQUENCE DESCRIPTION: SEQ ID NO:56:

| ANNTTTNNNN | TTTCNTGAAC | TTNTANAGCT | CATGNTCCCC | NNAANTGTGG | AAGGGGGTGG | 60 |
| GCACAGANAG | CCTGACCTCC | TGNGATGTGT | GGGTGGNGGT | GACCACGGAA | GGCTGAGGTC | 120 |
| CACCGNGGTG | GCGGTCACTC | TANGAACTAG | TGGATCCCCC | GGCCTGNAGG | AATTCGATAT | 180 |
| CAANCTTATC | GATACCGTCG | ACCTCGAGGG | GGGGNCCGGT | ACCCATTTCG | TCNTATAGTG | 240 |
| AGTCGTATTA | CGTGCGCTCA | CTGGGCGGCG | GTTACAACG | TCGNGACTGG | GAAAACCCTG | 300 |
| GNGTNACCCA | NCTTAATCGA | CTTGNAGNAC | ATCCCCCTTT | CGCCAGCTGG | CGTAATAGCG | 360 |
| AAGAGGCCCG | CACCNATCGN | CCTTCCCAAC | AGTTGNGCAG | CCTGAATNGC | GAATGGGAAA | 420 |
| TTGTAAGNGT | TCANTATTTN | NGTTNAAAAT | TNCGNNTTCA | ANNTTTNNGN | TTAANTCAAC | 480 |
| NTCATTTCTT | TNACCAATAG | GCCCNAAATC | GGNAAAATCC | CTTATTAAAT | TCAACNCAAT | 540 |
| AGNCCCANAT | AGNNTTNGAN | TTTTGGTACG | ANTCTGGGNA | NAANANTTCC | CCNATTCAAN | 600 |
| TACCTTCGCN | TCCAATNCCA | AACGGTCTAA | AACCCNNTTC | AGNNCNNATC | NCNCNTNNNN | 660 |
| TNAACCATCA | CNCTNTCAAT | NTTNA | | | | 685 |

(2) INFORMATION FOR SEQ ID NO:57:

(i) SEQUENCE CHARACTERISTICS:
        (A) LENGTH: 535 base pairs
        (B) TYPE: nucleic acid
        (C) STRANDEDNESS: single
        (D) TOPOLOGY: linear (ix) FEATURE:
        (D) OTHER INFORMATION:
          "N" represents any base.

(xi) SEQUENCE DESCRIPTION: SEQ ID NO:57:

| GAGCTCAGGC | TCCGGAGGTC | ACCCCNATGC | ACACATCCCA | GGAGTTCAGG | CTTCTNTGGA | 60 |
| CACCCCCTTC | NACACATCCC | AGGAGAAGGA | GCTCCAGCTT | CTGTTCCCTT | NAGTGAGGGT | 120 |
| TAATTGCGCG | CTTGGCGTAA | TCATGGTCAT | AGCTGTTTCC | TGTGTGAAAT | TGTTATCCGC | 180 |
| TCACAATTCC | ACACAACATA | CGAGCCGGAA | GCATAAAGTG | TAAAGCCTGG | GGTGCCTAAT | 240 |
| GAGTGAGCTA | ACTCACATTA | ATTGCGTTGN | GCTCAACTGC | CCGCTTTCCA | GTCGGNAAAC | 300 |
| CTGTCGGGCC | AGGTTGNATT | AATGAATCCG | GCCAACGCGC | GGNGAGAGGN | NGGTTTGGGG | 360 |
| TTTTGGGNGN | TCTTCCGNTT | CCTCGGTCAA | TTGATCGTTG | GTCGGNNCGT | CCGGTTGGGG | 420 |
| NAANGGTTNA | ANTCACTCAA | AGGNGGGATN | CGGTNTCCAA | GATCANGGGT | TCCGAGGNAA | 480 |
| NANATTTANN | AANGGCANNA | AAGGCAAGAC | CAAAAGCCNT | TNGTTGNTTT | TTNNA | 535 |

(2) INFORMATION FOR SEQ ID NO:58:

( i ) SEQUENCE CHARACTERISTICS:
   ( A ) LENGTH: 528 base pairs
   ( B ) TYPE: nucleic acid
   ( C ) STRANDEDNESS: single
   ( D ) TOPOLOGY: linear ( i x ) FEATURE:
   ( D ) OTHER INFORMATION:
      "N"represents any base.

( x i ) SEQUENCE DESCRIPTION: SEQ ID NO:58:

| | | | | | |
|---|---|---|---|---|---|
| GAGCTCTACT | AGANGCGGAG | AGACGGGTGC | GCGACGGAAA | AATTCCGGTA | CCCTTTGTGG | 60 |
| ATCGCGATAG | CCTGTTGGCC | AACGTTATTC | CCGTCGCCCC | CANTCNCAAT | CCGGAAACTG | 120 |
| AAGGAAGACC | GGAGAAGAAA | GCACTGACAC | GACAGTGTTC | GCTCCCTACC | CCCCACCCTA | 180 |
| AGAAGCTCGG | AGTCCAGCCT | GATTCCGATA | GCGACAGNGA | TACGATTATC | GATTTAACTA | 240 |
| TGGAAGGGGC | GGTATCTCTG | TAGATTNNNN | NNNNNGNTGA | ATTGTGCAAC | CCGNATTGNT | 300 |
| TGGGTGTCAC | TTGNAGACAA | GCCTTCTTGT | CAATCANTAG | TGTNNTTTTN | GTAATAAACG | 360 |
| GNTTNGTNGT | TTAACAAGAA | GNNNGGGTNT | CTCATCTTCT | NGGGGGTGAT | GAGNGNCTAC | 420 |
| CCCCCTTNTA | AAGNNATCGN | TTANANTNGN | NGTNTNATTT | GAGTTTTTTC | ACCCCNATTT | 480 |
| TATNNNTATC | AANNTCTTNN | TTGGNTNTNN | NTTCTAATNT | CATNCCCN | | 528 |

( 2 ) INFORMATION FOR SEQ ID NO:59:

( i ) SEQUENCE CHARACTERISTICS:
   ( A ) LENGTH: 643 base pairs
   ( B ) TYPE: nucleic acid
   ( C ) STRANDEDNESS: single
   ( D ) TOPOLOGY: linear ( i x ) FEATURE:
   ( D ) OTHER INFORMATION:
      "N"represents any base.

( x i ) SEQUENCE DESCRIPTION: SEQ ID NO:59:

| | | | | | |
|---|---|---|---|---|---|
| GAGCTCGTCC | TGGGGCTCGA | TCCAAGCGNA | ATTCACGACG | GGGACTTTCA | AGTGTCTCTG | 60 |
| CATCACAGTG | GNGAAATAAC | AGTCCTCGGT | GGGTGGACTG | ATGGGNAAAA | CGGTGTTCTC | 120 |
| CTCGACGATT | TTGTCTTTTG | CGGNCCACAC | CGAAGGGGTT | ACACTCCACA | GATGGGCAAC | 180 |
| GTCCTCGTCG | GGACCGATAG | CCAGAAACTG | CACATTGCGC | GACCCGTATT | GTTGCATCTC | 240 |
| AGTCCGGAGG | GTCTCCCACT | GCGTCGTTGG | GAGGCGACAG | NCGGGGGTTT | NCGATACAAT | 300 |
| TTCANAACTA | AACTNGCCCN | CCTTTGTCNG | ATGGTGCGAT | CAAACCCACT | CGTAAGGGTC | 360 |
| GGNAGACCGN | NTCTTTACAC | AGGTCCANCG | CTNGTGCCGC | AGNCNCCGNA | TTAGTACATT | 420 |
| TTNTCAAAN | ANCCCCTCTC | AATTNAACTC | CCCAGGAGGC | NANATTGGTT | NAACCCCCAG | 480 |
| ACGCATTAAC | ACCNTNTTTA | AGNCCCCTTN | AACNAANGTT | TAANNCCCNC | ATTTTANAAA | 540 |
| AGCCNCTNTA | AAGCCANNTN | CAGCCAATCA | TGATNCAANC | CTTTGGCCAA | NCCCTNCTT | 600 |
| CNCATTCCGG | AANACTTTAG | TCAAANTANC | TTTNGTTNCC | CCC | | 643 |

( 2 ) INFORMATION FOR SEQ ID NO:60:

( i ) SEQUENCE CHARACTERISTICS:
   ( A ) LENGTH: 552 base pairs
   ( B ) TYPE: nucleic acid
   ( C ) STRANDEDNESS: single
   ( D ) TOPOLOGY: linear ( i x ) FEATURE:
   ( D ) OTHER INFORMATION:
      "N"represents any base.

( x i ) SEQUENCE DESCRIPTION: SEQ ID NO:60:

| | | | | | | |
|---|---|---|---|---|---|---|
| GAGCTCCGNG | TTTCACCCNC | TCCGAGGAGT | NTCCCTACTG | CCACGNTAAA | TATGAAACTT | 60 |
| ACCTCAGAGT | CATGTCGGAC | TTTCGNGAAC | TGTTNCTGCG | ACAGNNCANC | TTCGANGGAG | 120 |
| TACGNTCGCG | GGTGAGTGAC | CACATCGATC | AAGTTATGTC | ATATAGGAAN | CCCCAGGAAC | 180 |
| TGGNTCGNGC | ACGTCAGGTC | CGGTGGACAC | ATACCGGNNC | TGAGAGATCA | GCTGNTGGNC | 240 |
| NGACAAANAN | CTNTTTTTT | TTTNTCTTNT | TNCGNGGCGA | CNGGANAATC | NTATNCATGN | 300 |
| TGGGGTGNGG | GACCCTCATG | GTGGGAGANN | GGGACCCCNN | TCGTTNNCAT | NGGGGCNNNC | 360 |
| CACCAANANT | TTCATCTTAC | NNCCCCCNTC | AACNAATTTC | CTATTCAANG | NNGGNTTNAN | 420 |
| ATTTCCNCCC | NACNNGNCNA | ANNCCGNNTT | CTTCACCCNA | ATCCNTTTA | ANNAANNTCN | 480 |
| CANCNNCAAA | CNCACCNCCC | TCACANCANC | NCNTNNNTNC | CCCTGCNNTN | NNNCNCNNCN | 540 |
| NANTTTCNNT | TT | | | | | 552 |

( 2 ) INFORMATION FOR SEQ ID NO:61:

( i ) SEQUENCE CHARACTERISTICS:
        ( A ) LENGTH: 653 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:61:

| | | | | | | |
|---|---|---|---|---|---|---|
| TTTTTGNCAN | CCGTGAAGCT | CAGGNCACCT | TAAATCGTTA | CTCTCACCTA | AAACGTGTTA | 60 |
| GCATCTACGA | TCCCCTGAAC | ATTGGTGTTA | ACTGTTTTGA | TTAAACACTT | GACTCTTTGT | 120 |
| ACCCGCGTGT | CATGTGTGGT | GTATCTGAGA | TGAGGGCCCC | GCAACATATT | TAGAGGTGTG | 180 |
| GGCTCTTCAC | GAACGATCGA | GAACTATGCG | ACTTCGTTCG | GAAGAAACGG | AGACGGTTCG | 240 |
| TTCCATCTTT | CTATTACGAG | TTTACATTCT | CATGTGGATC | GAGGGCATGC | TCTTGTTGAG | 300 |
| CACGTGCGCA | CTCTGCTGGC | TGGTGTTGCC | AGAGCGCTTT | GTGCACCTTT | TACCGAGTAT | 360 |
| TCGTAGGANG | TTATTTGGT | TTAATGCTTC | CTATTATCTG | GNNGGGGAAT | ACTTCACTTG | 420 |
| GGCCCGAGCC | TCCAGTTTCC | CAGGGGAGCT | TGTACGGTCT | TGTTGGANTT | ACACGTCCAC | 480 |
| ATGGCCNNNG | GGGACACCGN | GCCGNGGNTT | CAATCCGNAA | ACCCNTCGAC | CCCTTACGCC | 540 |
| ATNNNGGCTA | TATCTTGNTG | NNATCNNNCC | TNACCCNTTC | AAGCTTCNTT | NGGCNNAGNC | 600 |
| NNNGACCTTC | ANNCCNNGGN | NNNGNCCCNC | CNNCCNNATN | NTNNCCNNAN | CNT | 653 |

( 2 ) INFORMATION FOR SEQ ID NO:62:

( i ) SEQUENCE CHARACTERISTICS:
        ( A ) LENGTH: 538 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           " N"represents any base.

( x i ) SEQUENCE DESCRIPTION: SEQ ID NO:62:

| | | | | | | |
|---|---|---|---|---|---|---|
| GAGCTCACGT | TAATGGCAAT | TTGCAAGGGA | ACACATCACC | CACTGGCTGA | CTGTGGGATT | 60 |
| TTTATTGGTC | TCTTTACTTT | TTAAGCGTTC | TCGCCATCTT | GTGGCTACTT | TCAATATTGC | 120 |
| AGTTGAATGA | TTGGGCACAG | GTTCAACCAC | CTTGCAAATC | ATTAACTCAT | CTATTCAAGT | 180 |

| ACTTNGGGAG | ACTCTAATAT | CTCAAGTACT | TACACAGAAA | AGCAAGTGGA | CAAAAGCAAA | 240 |
| CTTNGGGAG | AAAGCCTAGG | AGGAATTAAT | GTAATTATTT | TTCACTACAC | TTTTAANCCT | 300 |
| TAATAAGAAA | AAAGCCTAGG | AGGAATTAAT | GTAATTATTT | TTCACTACAC | TTTTAANCCT | 300 |
| CAAGTAGNCA | GGCTTGTCGC | TGCCAGAGGN | CATCAAAACT | TTTCCATTTG | GGNGGGGAAG | 360 |
| GNNNGNTTGA | CGCCTNTTTC | AAAGATTGGG | GGGNAAANNN | NGGNAGGNAG | TCATTTGNGG | 420 |
| TNAANNNGTN | CNNNACCAGC | NNGNCANATN | GNANNCCCCN | CCTNTTCTNN | AANANANATT | 480 |
| NNCGNTNTTG | NNCAANCNCN | NTNNCCCCCC | NCNGGNNGGN | NNNNATTNNN | TCNNNGGG | 538 |

(2) INFORMATION FOR SEQ ID NO:63:

(i) SEQUENCE CHARACTERISTICS:
        (A) LENGTH: 605 base pairs
        (B) TYPE: nucleic acid
        (C) STRANDEDNESS: single
        (D) TOPOLOGY: linear (ix) FEATURE:
        (D) OTHER INFORMATION:
        " N"represents any base.

(xi) SEQUENCE DESCRIPTION: SEQ ID NO:63:

| GGGTTTTGAA | AGCTCTTGAA | GCTCACCAAC | CCTTGAGGAG | ACNAGTCGGC | GCTCGGGACT | 60 |
| CACATCCCCC | GACTCATTGC | GCTCTTGGAT | CACGACAACC | ATCGCGAACT | GTGCAATGTG | 120 |
| CTGGTCGGGC | TGCTACACCA | GAACACCCCA | CATGTGGGGC | CGTTCCATCC | GGCTTATCGG | 180 |
| GCGATTAAGA | AACTATCTAC | AACAGAAGTT | TCTCAATATC | TTGGTGGATA | GCGGACTCCA | 240 |
| GATCGATAGT | CTTTTTGAGG | GTTGTTACCA | CAGCGAAGCG | TACCGCTTGC | TGTTCCAGAT | 300 |
| CGAAAAAACG | AACTCCACGC | CTAGCTCTCT. | ANGCTGTGCA | AGCACCGTTT | TACCTGTCGG | 360 |
| TGAAAACGAA | ACTGAAGGNA | NACCTGTCCC | CGNCGGCGTN | TTTTANTGAA | ATNCTNAAAT | 420 |
| GGCTCTCATG | AAATATGACG | GCCTTAGTTT | CGTNTTNGGA | NNGGANAATT | NTGNNTCTCC | 480 |
| CCCCAAACAT | NCCNGNCNTG | GNCCCGTGNN | TTNGACCCTG | AACTTCCGCG | GGGGNCCNNT | 540 |
| NNCCTTNTGA | CAAACNGNCA | NTTCNTTCNT | NGNTCTCGTA | NCCCACCNNT | TTAGCGGTNT | 600 |
| NNTGG | | | | | | 605 |

(2) INFORMATION FOR SEQ ID NO:64:

(i) SEQUENCE CHARACTERISTICS:
        (A) LENGTH: 732 base pairs
        (B) TYPE: nucleic acid
        (C) STRANDEDNESS: single
        (D) TOPOLOGY: linear (ix) FEATURE:
        (D) OTHER INFORMATION:
        " N"represents any base.

(xi) SEQUENCE DESCRIPTION: SEQ ID NO:64:

| GNTTGCAACT | TCTCATAGNT | CAGACACCCC | CTNANACAAN | TTGGCGGCTT | GTTCGAGTCG | 60 |
| TGTCCGCATG | GACTGGAGTT | CCTCAACGGG | CAGGGCAGCC | ACTAATGATT | TGATTGTATC | 120 |
| TTCTTTGCAG | CATGGCGGTG | NTTGGCGTT | TAAGATCTCC | CTGCAGTTCG | GTTATTNTTG | 180 |
| TGTTTCCTCG | NTGCAGTAGT | GTCGTCTGCG | CCTGACTATC | GANTTTCGAT | AGGATCTGTT | 240 |
| TTGTGTCTTN | GTTGTCGAAG | GAGATTCTTT | CCAGGTCGTG | ACTATCGATT | CCATAGATGG | 300 |
| CGGCAGATAG | CTGCTGTAGC | GCTAACTGGA | CCTGTTTTTG | CTGTTGGCTG | GTGATCTGTC | 360 |
| GNCGACCGNT | GACGGCATTC | ACTACCGCCG | AAAAGTCTTG | TNGTNGAAGG | CAGACGAACC | 420 |
| TTTCGNCGAC | GTCAANTGGC | TTCTCCTCCN | CNTNTTCCCA | GCAGNCCCNA | NAGGGAAGTN | 480 |

| | | | | | |
|---|---|---|---|---|---|
| CCGTATTAGN | AGGNTTCTNC | CTTCCGGCCT | TCAAAAATCT | GNCGAACCCA | TTTCAATAAC | 540 |
| CTTTNNGCCC | CAAAANTGNA | ACCTANGTNA | ATAAAAACCG | CGGCAAAGTN | NGCCTATCAT | 600 |
| ACACCCCNTT | GTACGGTAAA | CTTTAAGNTT | AAAANTTTCA | AANTCTCGCC | ACCCANAGTG | 660 |
| AATCCNTGCT | AGCNANGAAA | GGNTNNATCG | ATTCNTCAA | ATCCNANTT | CNCCCCCNTT | 720 |
| NAATCCANNN | TT | | | | | 732 |

( 2 ) INFORMATION FOR SEQ ID NO:65:

( i ) SEQUENCE CHARACTERISTICS:
        ( A ) LENGTH: 699 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:65:

| | | | | | |
|---|---|---|---|---|---|
| TNATTGNATA | CTCTTAAGCT | CTCCGGCCCC | GCCNAAAACC | ANATTCTCG | TTCGCTAGTT | 60 |
| GGCTGNCCAT | CANCTNGCTG | TCATTCCTTT | TTAATCAGTG | CAACGAGTTC | TGGGGGTGGT | 120 |
| TGGAATGGCT | CGCCCTCCGA | GAGNGAGGAA | ACATCGTCGC | TATCTCCTAC | ACTACCGATG | 180 |
| TGTAGCGGAG | ACGACGGNTG | GGTATGATCG | NCGCCATNCN | TNTTTTNATC | ANNCTCCTCG | 240 |
| GNGTCGNNCN | CCTCCNCTCC | GGTGTCCTCG | TATTCATCCN | CGGTCTCCTC | GACACCTCTC | 300 |
| AACGTACTGG | NCGNGTNACC | TTNAGATACG | CNANACACGN | NAANGCNCCN | AGACTNCGNN | 360 |
| GGTGGATTTT | NTTTTNTTTT | TCTTCCCAAA | NCCACTNTTC | CGGNGGTCCC | NNNCANTCCG | 420 |
| NCTCCATAAN | TTCATCCCNN | CNNTNTNCNN | NNCCCATCTN | GGGGNNTTCT | TTGNAATCAG | 480 |
| AACCNGTNNG | NAANACACNN | TAANNNCNNT | TCCNNNTAAN | NNGCTNNCCT | CTNNTAACCT | 540 |
| NTTCCNANNA | NNCTNTCCTN | NCNCNNTTTT | TCNNATNCAT | NTCACTCTTC | TNCNNTTNTN | 600 |
| CCTNCTTCNN | NCTNNCCCTT | CCNNTTTCNC | NACCTNNTNT | NANCTCCNCT | CNNCCCNCTA | 660 |
| TCNNCCNTCT | ACANCNACGN | CNTTACCTAC | ATTNTNCAA | | | 699 |

( 2 ) INFORMATION FOR SEQ ID NO:66:

( i ) SEQUENCE CHARACTERISTICS:
        ( A ) LENGTH: 561 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
           "N"represents any base.

( x i ) SEQUENCE DESCRIPTION: SEQ ID NO:66:

| | | | | | |
|---|---|---|---|---|---|
| GAGCTCCATC | TCTGTAAAAC | CGTGGCCGCT | CATAATGCGA | TGTTGTGCCC | TCGTTTCGGG | 60 |
| AGCGTTGATC | GTTCTAAGCT | TAGTTCGGNA | AACAGTCTGT | CTTATGGTGT | GGGTAGTGGA | 120 |
| TGTGCACTTG | ACGTCATTAT | GTGCGAGAAT | CGGAGGCGAA | CCACCAATTG | TACCGATTTA | 180 |
| GCTTGAAGGT | GAAAAAGAG | GAATGGTTAG | TCTGCCAAAA | GACGGNATCC | GAAAATCATG | 240 |
| AGTCCAGTAA | TATACAATGA | TGAGAATTTC | CACGGTACAA | AACGAATTAA | CAAGGGGAAC | 300 |
| GGCTCCACCG | AGAAACTCCG | TACTTGAGCG | GGGGANAGGA | AGTCNGNNGG | NTAGAAAGTC | 360 |
| CCGGGGGAGA | AAGTTAACAA | GNAGAGCCAA | GGTAGCANCC | CNNCCCATTT | TNTTTAAAAN | 420 |
| GATGGACTNT | TGGGGAGGGG | NATTNNCANN | AANNNGTTTG | NANAAANATC | AAGGGAANAA | 480 |

| | | | | | |
|---|---|---|---|---|---|
| GCCNCCCNAA | ANNTTNACCC | CCCCGGAANG | GNCNGGTTCC | CGNTTTTTAA | ACNNTGTTTT | 540 |
| CCNAAAATTA | AATTANNAAA | A | | | | 561 |

( 2 ) INFORMATION FOR SEQ ID NO:67:

( i ) SEQUENCE CHARACTERISTICS:
        ( A ) LENGTH: 642 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:67:

| | | | | | |
|---|---|---|---|---|---|
| GAGCTCATGN | CACNCTGGAA | NAAAGCAGTT | TCTTGATCAA | TCGTAATGTC | ATACACTTTC | 60 |
| CTCAACAATT | CCTTCTCATT | TAGAAAGACA | GAGTTGATCT | GAATGTGAAA | CCACACTGCA | 120 |
| GGGCTTATCC | TAAGCATAAA | GATGTCCTTT | GGGAGTCTTT | TCAACGCTTA | AGCTATTCTC | 180 |
| AGTCAACCCA | GAAGAGGGTG | CAGGCAAACA | CACAGTGACT | CCAGTACCTG | AAATTGCAG | 240 |
| CTTGCCTCTC | TTGTCACTGA | CTGTTTATT | ACTTAGTGT | CTGATTTTA | TGAATACTTG | 300 |
| CAAGTAACTA | CAAGGCACAC | CCTTTAATT | ATAGTTTTAT | TCATTCACTC | AGACAAATTA | 360 |
| AAGGAACCCT | ATTAGCTGGG | CTATTTAAC | AAGTTTATGA | CATACAGATA | TGTCTTGAAA | 420 |
| ATTTACATTA | ACAGGGTAAA | AGGCTGGATN | TNTCAACTTN | CTCTGGGGGG | GCTGGTATTA | 480 |
| CTTNATGCCN | TNAAANTGAT | TATTCCCTCN | CTTTNCCCCA | TACAACCCCG | GATTAGGAAA | 540 |
| GTAAACCCNG | GTGAAAGGAT | TTTCNTTGGC | CCCTNACTNT | TTNCAAGAAT | TTTAAGGNNT | 600 |
| GGNAATCAAA | ATAGGTGGGC | CCCCCGGNGG | NGGCAGCCCT | NN | | 642 |

( 2 ) INFORMATION FOR SEQ ID NO:68:

( i ) SEQUENCE CHARACTERISTICS:
        ( A ) LENGTH: 734 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:68:

| | | | | | |
|---|---|---|---|---|---|
| GAATTCAGCG | TGTCGGAAAC | GCTGTATATA | TGCGAGTGGG | CCGGGTATCC | ATGACGTTGA | 60 |
| TTTGCGTGGT | TTGTGGTTAC | TGATCGGCTG | TCGGCGGTCG | CATTTCCACG | GAAATGTGCA | 120 |
| CGTNCTTCGC | GTTCCGAATN | ACATTTTTTG | GTAAANCAAG | CNGCTCCAAA | GACTNGGCCA | 180 |
| CAGGGGNGTA | GGTTATGTTC | NGTGCGTANG | ATCNATNAAA | CAATTGGACC | GGTNTCCCTG | 240 |
| TGGGTTTGNC | GGGGGNTTAT | TGNNGNAAAN | ANGCGGAANC | CCCCTNGTTT | CNCCAACCCT | 300 |
| CTTTNCCCCT | TGGAACCCAA | AACNCAGGTG | NGGGCCCCTC | NNNGNTTNTA | AACCNTCANA | 360 |
| CTTTTTTTTG | GNGAAGGCAA | NCCNTCTCCG | GTTCANTNTN | GGGNTTCCCA | GGGCTTGGNT | 420 |
| CNNANTTTTT | CCANNNAAGA | AACNGNCCCN | AANNTNTTTT | AAACNNACAA | CCCCNTAAAG | 480 |
| GCCCGNNGGT | NTCNCCCGGT | TTTCCCNTTT | TCTTGGNCGC | TTTCCNCCCC | CCCTNNAAAT | 540 |
| TGNTAGTTTA | TTANNCAACN | ANGTTNGNTT | TCANAGNNCA | AAGTCAAGCC | CTTTCCANNT | 600 |
| TGTTTTGGNN | GGCAANTTTC | GGCANTANTT | TTTNGGTNTT | NGANGGNCTT | TTNANAACCN | 660 |
| NNGGGGNCGG | TTTTNTNAAA | TTTANNNCNN | TTTCCCCNAN | TTCNTTATTT | CTNCCCNCCC | 720 |

```
GGGGNNCCCC  NCCN                                                                                          734
```

( 2 ) INFORMATION FOR SEQ ID NO:69:

( i ) SEQUENCE CHARACTERISTICS:
        ( A ) LENGTH: 99 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

```
GAATTCAGCT  TGTCGTAATC  TCTGTATATA  TGCGAGTTGG  CCGGGTATCC  ATGACGTTGA    60
TTTGCGTGGT  TTGTGGTTAC  TGATCGGCTG  TTTTAGTGA                             99
```

( 2 ) INFORMATION FOR SEQ ID NO:70:

( i ) SEQUENCE CHARACTERISTICS:
        ( A ) LENGTH: 645 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
            " N"represents any base.

( x i ) SEQUENCE DESCRIPTION: SEQ ID NO:70:

```
CNNCNTTNNN  NGACACAAGC  TGGAGCTCCA  CCNCGGTGGC  GGCCGCTCTA  GAACTAGTGG    60
ATCCCCCGGG  CTGCAGGAAT  TCGAAGTGTT  GACCAGCGTG  ACTGTAGCTA  CAGTGCCCGG   120
TAGCCAAATT  ACAGGACGCG  TGATGAGCCC  TAGCTGCGCC  ATGTGGCGGG  TTCCCACTAC   180
GAGGGCGCAA  GTGCTGGGGG  CTTGAATAAA  GGCGGTGTCA  AGGTACACCG  TGTGGGTGTA   240
ATTGGGTTGG  ATGATAATCC  GTTGCTGCAC  ACGTAGGGAG  AAGAAGTGG   TTTCGTTTGG   300
GGGTGACATG  TTCATGAGTT  GCCAGGGCTC  GGGACGGAAA  CAGGGGAAGA  TGCAGATGTC   360
GCCCTCGATG  GTGCCCGGNG  TGATGGCTTG  GAACGTGTAG  TTAAGATTAA  TAACTTCCAT   420
GCTGAGGTTT  CGTAAGCCGG  GTTCGATGAA  TTCTGGCATG  NAACAATTTG  AGAATCCAAA   480
CATTTATTAA  AACGTAATTC  CGAAGTNTCC  NATGGGATTN  TAAGGTTGAT  GCCNAGGGTG   540
TTGAAGTNTT  GGNTGGTCCG  GTAGCAATAT  GTTTGGTGGA  ATTNATGCTT  TCTTGGTTGN   600
GAAAATTGAG  GGTCCCTTTC  GGATTTNGGC  NNGNNAATTT  CCNCN                    645
```

( 2 ) INFORMATION FOR SEQ ID NO:71:

( i ) SEQUENCE CHARACTERISTICS:
        ( A ) LENGTH: 209 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

```
GAATTCGAAT  TGTTGACCAG  CGTGACTGTA  GCTACAGTTC  CCGGTAGCCA  AATTACAGGA    60
CTCGTGATGA  GCCCTAGCTG  CGCCATGTGC  GGTTCCCACT  ACAGGGCGCA  AGTTCTGGGG   120
GCTTGAATAA  AGGCGGTGTC  AAGGTACACC  GTGTGGGTGT  AATTGGGTTG  GATGATAATC   180
CGTTTGCTGC  ACACTAGGGA  GAAGAAGTT                                        209
```

( 2 ) INFORMATION FOR SEQ ID NO:72:

( i ) SEQUENCE CHARACTERISTICS:
        ( A ) LENGTH: 570 base pairs
        ( B ) TYPE: nucleic acid
        ( C ) STRANDEDNESS: single ( D ) TOPOLOGY: linear ( i x ) FEATURE:
  ( D ) OTHER INFORMATION:
    " N"represents any base.

( x i ) SEQUENCE DESCRIPTION: SEQ ID NO:72:

| | | | | | |
|---|---|---|---|---|---|
| GAATTCCTAG | CCAGCTGTAT | GTCCAAAATA | CAACCGCGCA | ACCACTCTGC | TCATGTACCC | 60 |
| TGGTGCGGTT | GAACTAGCTA | ACAGAACTTT | AAAAACTAAC | GGAGACATCT | CCAGCGTCCT | 120 |
| CACCGTAGCT | CGGCTGGTTT | ATGTGTTAGT | TAAGCAAAAC | CGTCAAGACC | TGGTTACGCA | 180 |
| CACCGCCATG | CAACACGTCC | GTGACCTCAT | NNTGCGTCTC | CATAAATCAC | ATATAGCTTC | 240 |
| TTTCCTATCA | CGGTTTGCTC | GCCAGGAACT | GTATCTTGCC | AGCAGCATTA | TTCATTCCAT | 300 |
| GCTAAATTAC | TCTACCGAAA | GACGAGACAT | ATTTGTCTTC | GAAACAGGAT | GTGTTCACTA | 360 |
| GCTGAACTCT | CACACTGGTC | ACAACTCATC | GGNGGCCACG | AAAACGTCAC | ATCAGCGATT | 420 |
| TNTCAGTCCA | TGCGTTGGAG | NGGGGNAGAG | ACACGCCTAG | ACACTNTNTA | CATGTTNCAA | 480 |
| AGNACTATCT | GGACCTAAAA | TGTCTTTTTT | TAGACTTAGC | AAAATTTCAT | CCAGATAATN | 540 |
| TCCAGGGAAT | TNGGCGTTAA | AGTCCNTGAA | | | | 570 |

( 2 ) INFORMATION FOR SEQ ID NO:73:

( i ) SEQUENCE CHARACTERISTICS:
    ( A ) LENGTH: 563 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
      " N"represents any base.

( x i ) SEQUENCE DESCRIPTION: SEQ ID NO:73:

| | | | | | |
|---|---|---|---|---|---|
| GAATTCCATC | CCCCCGATGA | ATTTGCGGCG | ACTGGCGGCG | TGCCGCTGAG | CCGCCAGCTG | 60 |
| TTTGTGCCGG | TGGTGTTCCT | GAGCGGCCTG | GCGCAGGGTG | TTGCCGGTAA | AATCAAAAGC | 120 |
| GCTGCCCTGC | TTCTCTCGAC | GCCACAATTG | TCCATATCGA | ACGAACATGA | GTCTAGAAAT | 180 |
| GATACACACG | TACCGCTTTA | GGCGATCGCC | GCTCGAGTCC | CGGCGAACTA | CGCTATGCGT | 240 |
| TCGCGCCACC | AGGGACGACG | ACGCACCGGG | AACACCACCG | CAGTGGNGAG | AGGAGGCAGG | 300 |
| AGGGGGATGA | TTTTTGTTTA | TAGGCTCGGC | CTTANCGATT | TCATAGTACA | CATAGAATAA | 360 |
| ATTACGNCAG | ACGGTGTCAT | GCTCGCCGAA | AGCCAGACTC | AAGCGCCGGT | ANANAGTATT | 420 |
| TTCCCNTACA | AAACCGNTTG | GTNTTGGCGT | AGGTGATGNN | AGNTTAAGTC | AANATTGGNG | 480 |
| TTAAACGCCA | GGTAAGTNAT | GAATGAANGT | GGTCCGAGGA | ANGCACATAG | NTCCCANCCT | 540 |
| TAATCCGNGA | GAGGTCAAAN | CCT | | | | 563 |

( 2 ) INFORMATION FOR SEQ ID NO:74:

( i ) SEQUENCE CHARACTERISTICS:
    ( A ) LENGTH: 579 base pairs
    ( B ) TYPE: nucleic acid
    ( C ) STRANDEDNESS: single
    ( D ) TOPOLOGY: linear ( i x ) FEATURE:
    ( D ) OTHER INFORMATION:
      " N"represents any base.

( x i ) SEQUENCE DESCRIPTION: SEQ ID NO:74:

| | | | | | |
|---|---|---|---|---|---|
| GAATTCGTAC | AATCTCACCC | AAGAGTTGTC | GTTAGTGGAG | GACGCTCGGT | TTTGCCAGAC | 60 |

```
GCGGCCCGTG  AACGCCGAGC  GCGTTCGCGG  TGTCTTCGGC  GCGCTCTATC  GCGCCGCGTC     120

CCCGCACATG  CGGGAGGAGA  GTGACCGCAT  CAAGCTGATT  TTGGGACGCT  TGTTGCTGGG     180

ACCCGTGGCC  GTGCCCTGCT  ACTGTGACGA  ATGGGAGGCG  AATGACTACA  TGGTGGAGGC     240

GGCGCAGTTT  TGCACCGGCC  CCCTGCTGTA  TGTGNACCGA  CGCTGCCACT  GTCCCGGTAT     300

GGGGGGCGCG  CTCGCTTTCA  CCGTGATGGA  AGGGCATNTC  GCGACGCATN  TTTTTAGAGG     360

GNTGCTGTCA  CTCACTGAGT  GGAACCAGNA  CTGCCCCACA  TTTTTGGCC   NTGCNGAACG     420

GTGANCAGNG  GGATCGGACA  NGAATNGCTG  TCTNCCCGNN  AACTTACGTT  TTNTNTAAGG     480

AATATCCTAA  TTATGGGGAG  ACGGGTTTCT  CACCNATAGG  GTTATAGTAT  NTATACAATC     540

TGGGANCCNA  NCCCNCTAA   TTAAAAAATT  TNGTGGGTA                              579
```

(2) INFORMATION FOR SEQ ID NO:75:

(i) SEQUENCE CHARACTERISTICS:
    (A) LENGTH: 586 base pairs
    (B) TYPE: nucleic acid
    (C) STRANDEDNESS: single
    (D) TOPOLOGY: linear (ix) FEATURE:
    (D) OTHER INFORMATION:
      " N"represents any base.

(xi) SEQUENCE DESCRIPTION: SEQ ID NO:75:

```
GAATTCACGT  GTACGGGGAC  ATTGACGACC  TGGGGTTCCG  CCGCCGACTC  CACTATTAGA     60

GCGTCCTGGG  GCGCGCGACA  CTGAAAGACG  GTTGGCGAGG  AAGCCATCGC  CGCACGCCGT     120

CATGGAAAAC  TGGACGGCAG  TCGAGTTACT  CCCGAAAGTC  GGGATCCCGG  CCGACTTTCT     180

CACGCATGTA  AAAACCAGCG  CCGGGGAAGA  AATGTTCGAC  AGTCTGCGCA  TTTACTACGG     240

AGATGACCCG  GAACGCTACA  ACATCCACTT  CGAAGCCATC  TTCGGCACCT  TCTNCAATCG     300

TCTCGAATGG  GTTTACTTCC  TCCAGACGGA  CCTGGCATCG  GCNGCGNACG  CCATCAAGTT     360

CGATGACCTG  AACAAGATGA  CAACAGGGAA  AATGGTTGTT  TCACATCCAG  NTTGCCGCGT     420

NTNGGCAGGG  NGCCGGAATG  CCANCTCGAC  CAGACACCAC  ATNGTTACCA  ATNCAGTAAA     480

AAGCCCCTCA  CCNCCCCCTC  NCCTCANGGC  CCCTTTTATG  ACCTGGAAAN  NTCNGACNCA     540

ACCCGANGTC  NTATTCGAG   CNNGAAACCA  CTTNNTNTTN  NAAANC                    586
```

(2) INFORMATION FOR SEQ ID NO:76:

(i) SEQUENCE CHARACTERISTICS:
    (A) LENGTH: 566 base pairs
    (B) TYPE: nucleic acid
    (C) STRANDEDNESS: single
    (D) TOPOLOGY: linear (ix) FEATURE:
    (D) OTHER INFORMATION:
      " N"represents any base.

(xi) SEQUENCE DESCRIPTION: SEQ ID NO:76:

```
GAATTCTGTA  ATCCATGCCA  CTTGATTGCG  ATACGTTTCA  TGCAAGCTGG  GTTGCAACTG     60

TTCTTAATCT  CGATTGGCCG  TCGCGGGCTT  CCACTCTCAT  TGAAGATGAT  TCCGAACGGG     120

TAAAGCGTCA  GAAAAAGAG   CTGGTGCGGA  TGTTTGATGA  GGCGTCGGAG  CATGGCATCA     180

ATGCCATGAT  TTTTCAGGTC  TCTCCTGCTG  CCGATGCTTT  CTATAAATCG  GAGTATCTGC     240

CGTGGTCGTC  TTATCTCACG  GGTACGCTCG  GAAAAGATCC  GGGCTTCGAT  CCACTNCGCT     300

TTGCAATTGC  GGAAGCGCAT  AAGCGCGGGA  TCGAGCTGCA  TGCATGGCTC  AATCCTTATC     360
```

| GCGTTTCGAT | GGATGTGCGA | CCAGCAACGC | GGAAAGNACT | GAAAAAACTC | TGCCGGCGAT | 420 |
| TCTCCGNCCA | GCGTCTATAA | AACCAATCCA | GGCTGGGTNG | NTTATNTCTG | CGGATCCNTT | 480 |
| ATGTGTTGGA | TCCGGGTNTC | CCGGATGTTG | NCAGTGGNTG | AGAATTTAAG | GCCGAAGCCG | 540 |
| TCANAATTTA | TGTCGAGGAT | CAGTCC | | | | 566 |

( 2 ) INFORMATION FOR SEQ ID NO:77:

( i ) SEQUENCE CHARACTERISTICS:
        ( A ) LENGTH: 570 base pairs
        ( B ) TYPE: nucleic acid
        ( C ) STRANDEDNESS: single
        ( D ) TOPOLOGY: linear ( i x ) FEATURE:
        ( D ) OTHER INFORMATION:
          " N"represents any base.

( x i ) SEQUENCE DESCRIPTION: SEQ ID NO:77:

| GAATTCATTC | ATCTTCATGG | GGNAGNAGAA | AAATGAACAT | CAGGACCAGC | TTCCACATTG | 60 |
| ACACCATGGC | TGTCACCATG | CTCTTTTTCA | ACGGGCTGTT | CAACCTTAAC | ATCTTTCGAG | 120 |
| ACGTAGTGGC | CGATGACTCA | CAACAAAAAA | GTTGTGATTA | TATGAAACAA | CAACACTTTT | 180 |
| TNCGCACGAT | GGGTATAGCC | TCTGTGTTTC | TCAGACCCGT | CTTTAGTCCT | ATCATTTACA | 240 |
| TATGTGTCAG | TCGNAAAATC | ATACAGGGTA | TCTGCAAATT | GTTATAAAA | GTACCAAACC | 300 |
| ATACCATAAG | CTCGGAACGT | GTAAAGCTTA | TGTCTCCAAA | TAGAATGAAC | GACGATGCCC | 360 |
| CAGAGCTTCC | GCCCAGGGGA | ATATGAATCC | GCGTTCTANA | TTATTGCGCG | TTGGTAGGGN | 420 |
| AACGACACAA | CCAGCCGATT | TNTGTTTGGG | ACCGGTCACA | ANCCCCGAC | ATTGGAAATC | 480 |
| GACATTGTTC | GGTTGGNGAA | CAGNCTTTTT | ANAACATGAA | CAACTCCCCC | GTACCCTCTG | 540 |
| AAGTGTTAAG | ACGCGAGNAT | TCGGAGTAGG | | | | 570 |

( 2 ) INFORMATION FOR SEQ ID NO:78:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

| GCTCGATTCC | ACCGAACTCT | CAATGAACGG | TCTGCATTG | 39 |

( 2 ) INFORMATION FOR SEQ ID NO:79:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

| AATGCGGATA | GAGCTTGCCA | AGTGCTCCGT | CACCAATTG | 39 |

( 2 ) INFORMATION FOR SEQ ID NO:80:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

TGCGCTTCAC AGTAGAAGAG GGACAACTGC TGCAACACAC C    41

( 2 ) INFORMATION FOR SEQ ID NO:81:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

AGGAGCTCCA TTGGAAGAGA CGGATGAGGA ACTCTCCACA G    41

( 2 ) INFORMATION FOR SEQ ID NO:82:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:82:

ATCACACATC TGCATCCTGG GGCGTGAATC ATAGTGTTGA C    41

( 2 ) INFORMATION FOR SEQ ID NO:83:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

ACGAATCCGT CACAGAGAGC CAGCACATTG CACAGTTCGC    40

( 2 ) INFORMATION FOR SEQ ID NO:84:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

GCAACACGAG GCAGAACACT GCTACGCGAG TTGTACCG    38

( 2 ) INFORMATION FOR SEQ ID NO:85:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

CGCTGTCGCT CTCTTCCTTG AGCACGATAC GGTGTTGC    38

( 2 ) INFORMATION FOR SEQ ID NO:86:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

AATGTTCGAC AGTCTGCGCA CAGACAGCAC AGGAACCG    38

( 2 ) INFORMATION FOR SEQ ID NO:87:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

```
ACTCTGCTGG CTGGTGTTGA GGCGAACCAC CAATTGTAC                           39
```

( 2 ) INFORMATION FOR SEQ ID NO:88:

( i ) SEQUENCE CHARACTERISTICS:
        ( A ) LENGTH: 669 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:88:

```
GTGGTGCTAG TGACAGTGAC ATTCTGGCTC AGGCTGTCAA TCAAGCTGGT ATTGACCATA    60
GCTCAGCAGG TACCACCATC ACCACCCCAT CCATCTTCAC CACCACCACT GCTCCCAGTA    120
CCCCCCAAGG TGTTGTTACT CAGCCTGAGA GTCAGCCCAT CCACCACTT GTTTGCAATC     180
CTGAAACCCT GTTCATCCCA CGTAAGAAAT CCCGGAAGAC AGACTGCCCC ACCAAGATCA    240
TTATTAAACC ACCCGTGCCT CCCACGTCCA CCATGATCCC AGCATCCAG ATTAAGAAAG     300
AGCCTGAGGA ATTCTTCAAG CTCCAGTACA AAGACCAGGA CATCCAACCC ACCTCTGGAT    360
GTATTGTGAT CTCAGACAGT GAAGAGGAAG AAGACACTCA GACTCTGATT CCCACAGCTT    420
CCTCCTCCTC TTCCTCAGAG AACCAGGGTG TGCAGCTGAC AATGACCACC CCAGGCAGTG    480
GATCAGTGGG CAAAATGTCT GTGGAGAGTT CCTCATCCTC CAGCAGCGAG TCAGAGTGCT    540
GTGAAGAATG TGGACTTTCA TCTCCCAGTA CGTTGGCATC TCCAGTGTCC CCCATTCCAC    600
CACCCCCACC AGCACCCGTG ATGCCCAGCA CCTCTGGTCG CAAGCCCAAG GGTCCCAAGA    660
CCAAGACCA                                                            669
```

( 2 ) INFORMATION FOR SEQ ID NO:89:

( i ) SEQUENCE CHARACTERISTICS:
        ( A ) LENGTH: 663 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:89:

```
TTGGTGCTAA TGACAGTGAC ATACTGGGTC AGGCTGCCAA TCAACCTGGT ATTCACCATA    60
GCTCAGCAGG TATCACCATC ACCACCCCAT CCATCCTCAC CACCACCACT GCTCCCAGCA    120
CCCCCCAAGT CGCTGTTACT CAGTCAGAGA GTCAGCCAAT GCCGCCACCT GTTTGCAATC    180
CTGAAACCCT GTTCATCCCA CGTAAGGAAT CCCGGAAGAC AGACTGCCCT ACCAAGATCA    240
TTATTAAACC ACCCGTGCCT CCCACGTCCA CCATGATCCC AGCATCCAG ATTAAGATAG     300
AGCCTGAGGA ATTCTTCAAG CTCCAATACA AAGACCAGGA CATCCAACCC ACCTCTGGAT    360
GTATTGTGAT CTCAGACAGT GAAGAGGAAG AAGACACTCA GACTCTGATT CCCACAGCCT    420
CCTCTTCCTT AGATAACCAG GGTGTGCAGC TGACAATGAC CACCCCAGGC AGTGGATCAG    480
TGGGCAAAAT GTCTGTGGAG AGTTCCTCAT CCTCCAGCAG CGAGTCAGAG TGCTGTGAAG    540
AATGTGGACT TTCATCTCCC AGTACGTTGG CATCCCGGT GTCTCCCTT CCACCACCCC      600
CACCAGCACC CGTGATGCCC AGCACCTCTG GTGCCAAGCC CAAGGGTCCC AAGACCATGA    660
```

```
                                                                                      CCA                                                                                                      663

( 2 ) INFORMATION FOR SEQ ID NO:90:

( i ) SEQUENCE CHARACTERISTICS:
        ( A ) LENGTH: 663 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:90:

CTTCTTATCA  CCATCAGGTG  ACATCCTCGC  CCAGGCTGTC  AATCATGCCG  GTATCGATTC        60
CAGTAGCACC  GGCCCCACGC  TGACAACCCA  CTCTTGCAGC  GTTAGCAGCG  CCCCTCTTAA       120
CAAGCCGACC  CCCACCAGCG  TCGCGGTTAC  TAACACTCCT  CTCCCCGGGG  CATCCGCTAC       180
TCCCGAGCTC  AGCCCGCGTA  AGAAACCGCG  CAAAACCACG  CGTCCTTTCA  AGGTGATTAT       240
TAAACCGCCC  GTGCCTCCCG  CGCCTATCAT  GCTGCCCCTC  ATCAAACAGG  AAGACATCAA       300
GCCCGAGCCC  GACTTTACCA  TCCAGTACCG  CAACAAGATT  ATCGATACCG  CCGGCTGTAT       360
CGTGATCTCT  GATAGCGAGG  AAGAACAGGG  TGAAGAAGTC  GAAACCCGCG  GTGCTACCGC       420
GTCTTCCCCT  TCCACCGGCA  GCGGCACGCC  GCGAGTGACC  TCTCCCACGC  ACCCGCTCTC       480
CCAGATGAAC  CACCCTCCTC  TTCCCGATCC  CTTGGGCCGG  CCCGATGAAG  ATAGTTCCTC       540
TTCGTCTTCC  TCCTCCTGCA  GTTCGGCTTC  GGACTCGGAG  AGTGAGTCCG  AGGAGATGAA       600
ATGCAGCAGT  GGCGGAGGAG  CATCCGTGAC  CTCGAGCCAC  CATGGGCGCG  GCGGTTTTGG       660
TGG                                                                                                                                                                                           663
```

( 2 ) INFORMATION FOR SEQ ID NO:91:

( i ) SEQUENCE CHARACTERISTICS:
        ( A ) LENGTH: 219 amino acids
        ( B ) TYPE: amino acid
        ( C ) STRANDEDNESS: single
        ( D ) TOPOLOGY: linear ( x i ) SEQUENCE DESCRIPTION: SEQ ID NO:91:

```
Gly  Ala  Ser  Asp  Ser  Asp  Ile  Leu  Ala  Gln  Ala  Val  Asn  Gln  Ala  Gly
 1              5                        10                           15

Ile  Asp  His  Ser  Ser  Ala  Gly  Thr  Thr  Ile  Thr  Thr  Pro  Ser  Ile  Phe
                20                       25                     30

Thr  Thr  Thr  Thr  Ala  Pro  Ser  Thr  Pro  Gln  Gly  Val  Val  Thr  Gln  Pro
               35                       40                     45

Glu  Ser  Gln  Pro  Ile  Pro  Pro  Leu  Val  Cys  Asn  Leu  Thr  Leu  Phe  Ile
     50                       55                      60

Pro  Arg  Lys  Lys  Ser  Arg  Lys  Thr  Asp  Cys  Pro  Thr  Lys  Ile  Ile  Ile
65                       70                      75                         80

Lys  Pro  Pro  Val  Pro  Pro  Thr  Ser  Thr  Met  Ile  Pro  Ala  Ser  Gln  Ile
                    85                       90                       95

Lys  Lys  Glu  Pro  Glu  Glu  Phe  Phe  Lys  Leu  Gln  Tyr  Lys  Asp  Gln  Asp
               100                       105                    110

Ile  Gln  Pro  Thr  Ser  Gly  Cys  Ile  Val  Ile  Ser  Asp  Ser  Glu  Glu  Glu
          115                       120                    125

Glu  Asp  Thr  Gln  Thr  Leu  Ile  Pro  Thr  Ala  Ser  Ser  Ser  Ser  Ser  Ser
     130                      135                      140

Glu  Asn  Gln  Gly  Val  Gln  Leu  Thr  Met  Thr  Thr  Pro  Gly  Ser  Gly  Ser
145                      150                      155                       160

Val  Gly  Lys  Met  Ser  Val  Glu  Ser  Ser  Ser  Ser  Ser  Ser  Ser  Glu  Ser
```

|     |     |     |     | 165 |     |     |     |     | 170 |     |     |     |     | 175 |     |
|-----|-----|-----|-----|-----|-----|-----|-----|-----|-----|-----|-----|-----|-----|-----|-----|
| Glu | Cys | Cys | Glu | Glu | Cys | Gly | Leu | Ser | Ser | Pro | Ser | Thr | Leu | Ala | Ser |
|     |     |     | 180 |     |     |     |     | 185 |     |     |     |     | 190 |     |     |
| Pro | Val | Ser | Pro | Ile | Pro | Pro | Pro | Pro | Ala | Pro | Val | Met | Pro | Ser |
|     |     | 195 |     |     |     | 200 |     |     |     |     | 205 |     |     |     |
| Thr | Ser | Gly | Arg | Lys | Pro | Lys | Gly | Pro | Lys | Thr |
|     |     | 210 |     |     |     | 215 |     |     |     |     |

( 2 ) INFORMATION FOR SEQ ID NO:92:

( i ) SEQUENCE CHARACTERISTICS:
        ( A ) LENGTH: 218 amino acids
        ( B ) TYPE: amino acid
        ( C ) STRANDEDNESS: single
        ( D ) TOPOLOGY: linear ( x i ) SEQUENCE DESCRIPTION: SEQ ID NO:92:

| Gly | Ala | Asn | Asp | Ser | Asp | Ile | Leu | Gly | Gln | Ala | Ala | Asn | Gln | Pro | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ile | His | His | Ser | Ser | Ala | Gly | Thr | Thr | Ile | Thr | Thr | Pro | Ser | Ile | Leu |
|     |     |     | 20  |     |     |     |     | 25  |     |     |     |     | 30  |     |     |
| Thr | Thr | Thr | Thr | Ala | Pro | Ser | Thr | Pro | Gln | Val | Ala | Val | Thr | Gln | Ser |
|     |     | 35  |     |     |     |     | 40  |     |     |     |     | 45  |     |     |     |
| Glu | Ser | Gln | Pro | Met | Pro | Pro | Pro | Val | Cys | Asn | Pro | Glu | Thr | Leu | Phe |
|     | 50  |     |     |     |     | 55  |     |     |     |     | 60  |     |     |     |     |
| Ile | Pro | Arg | Lys | Glu | Ser | Arg | Lys | Thr | Asp | Cys | Pro | Thr | Lys | Ile | Ile |
| 65  |     |     |     |     | 70  |     |     |     |     | 75  |     |     |     |     | 80  |
| Ile | Lys | Pro | Pro | Val | Pro | Pro | Thr | Ser | Thr | Met | Ile | Pro | Ala | Ser | Gln |
|     |     |     |     | 85  |     |     |     |     | 90  |     |     |     |     | 95  |     |
| Ile | Lys | Ile | Glu | Pro | Glu | Glu | Phe | Phe | Lys | Leu | Gln | Tyr | Lys | Asp | Gln |
|     |     |     | 100 |     |     |     |     | 105 |     |     |     |     | 110 |     |     |
| Asp | Ile | Gln | Pro | Thr | Ser | Gly | Cys | Ile | Val | Ile | Ser | Asp | Ser | Glu | Glu |
|     |     | 115 |     |     |     |     | 120 |     |     |     |     | 125 |     |     |     |
| Glu | Glu | Asp | Thr | Gln | Thr | Leu | Ile | Pro | Thr | Ala | Ser | Ser | Ser | Leu | Asp |
|     | 130 |     |     |     |     | 135 |     |     |     |     | 140 |     |     |     |     |
| Asn | Gln | Gly | Val | Gln | Leu | Thr | Met | Thr | Thr | Pro | Gly | Ser | Gly | Ser | Val |
| 145 |     |     |     |     | 150 |     |     |     |     | 155 |     |     |     |     | 160 |
| Gly | Lys | Met | Ser | Val | Glu | Ser | Ser | Ser | Ser | Ser | Ser | Ser | Glu | Ser | Glu |
|     |     |     |     | 165 |     |     |     |     | 170 |     |     |     |     | 175 |     |
| Cys | Cys | Glu | Glu | Cys | Gly | Leu | Ser | Ser | Pro | Ser | Thr | Leu | Ala | Ser | Pro |
|     |     |     | 180 |     |     |     |     | 185 |     |     |     |     | 190 |     |     |
| Val | Ser | Pro | Leu | Pro | Pro | Pro | Pro | Ala | Pro | Val | Met | Pro | Ser | Thr |
|     |     | 195 |     |     |     | 200 |     |     |     |     | 205 |     |     |     |
| Ser | Gly | Ala | Lys | Pro | Lys | Gly | Pro | Lys | Thr |
|     | 210 |     |     |     | 215 |     |     |     |     |

( 2 ) INFORMATION FOR SEQ ID NO:93:

( i ) SEQUENCE CHARACTERISTICS:
        ( A ) LENGTH: 264 amino acids
        ( B ) TYPE: amino acid
        ( C ) STRANDEDNESS: single
        ( D ) TOPOLOGY: linear ( x i ) SEQUENCE DESCRIPTION: SEQ ID NO:93:

| Pro | Pro | Pro | Pro | Thr | Pro | Leu | Asp | Ile | Leu | Ala | Gln | Ala | Val | Ser | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Gly | Ile | Asp | Ser | Ser | Ser | Ala | Gly | Val | Thr | Ala | Pro | Ile | Pro | Ser |
|     |     |     | 20  |     |     |     |     | 25  |     |     |     |     | 30  |     |     |

| Ser | Met | Ile | Thr | Thr | Thr | Ala | Pro | Thr | Ile | Ala | Pro | Thr | Thr | Thr | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |
| Ile | Gln | Val | Pro | Gly | Met | Gln | Ile | Thr | Ala | Ser | Leu | Gln | Gly | Thr | Pro |
|     | 50  |     |     |     |     | 55  |     |     |     |     | 60  |     |     |     |     |
| Lys | Pro | Lys | Ser | Lys | Pro | Lys | Pro | Lys | Ile | Pro | Ala | Pro | Pro | Ser | Ala |
| 65  |     |     |     |     | 70  |     |     |     |     | 75  |     |     |     |     | 80  |
| Ala | Ile | Ala | Ala | Pro | Ala | Pro | Ser | Ser | Ser | Thr | Thr | Thr | Ser | Thr | Thr |
|     |     |     |     | 85  |     |     |     |     | 90  |     |     |     |     | 95  |     |
| Ser | Ser | Thr | Asn | Pro | Ala | Val | Cys | Lys | Pro | Thr | Asp | Ser | Met | Ser | Gln |
|     |     |     | 100 |     |     |     |     | 105 |     |     |     |     | 110 |     |     |
| Arg | Lys | Lys | Ser | Arg | Lys | Thr | Gln | His | Pro | Met | Lys | Val | Ile | Ile | Lys |
|     |     | 115 |     |     |     |     | 120 |     |     |     |     | 125 |     |     |     |
| Pro | Pro | Ser | Pro | Pro | Thr | Cys | Met | Leu | Lys | Pro | Ser | Glu | Ile | Lys | Gln |
|     | 130 |     |     |     |     |     | 135 |     |     |     | 140 |     |     |     |     |
| Glu | Gly | Glu | Ser | Phe | Ile | Arg | Tyr | Lys | Gly | Gln | Asp | Ile | Gln | Pro | Thr |
| 145 |     |     |     |     | 150 |     |     |     |     | 155 |     |     |     |     | 160 |
| Ser | Gly | Cys | Ile | Val | Ile | Ser | Asp | Ser | Glu | Glu | Glu | Asp | Thr | Glu |
|     |     |     |     | 165 |     |     |     |     |     | 170 |     |     |     | 175 |     |
| Pro | Gly | Val | Ser | Ala | Arg | Ala | Thr | Ser | Glu | Gln | Gln | Gly | Val | Gln | Leu |
|     |     |     | 180 |     |     |     |     | 185 |     |     |     |     | 190 |     |     |
| Lys | Ile | Thr | Thr | Lys | Met | Ser | Gly | Ala | Ser | Gly | Gln | Ile | Pro | Met | Asp |
|     |     | 195 |     |     |     |     | 200 |     |     |     |     | 205 |     |     |     |
| Ser | Ser | Ser | Ser | Ser | Ser | Ser | Asp | Ser | Glu | Cys | Cys | Asp | Glu | Cys | Ala |
|     | 210 |     |     |     |     |     | 215 |     |     |     | 220 |     |     |     |     |
| Gly | Asp | His | Phe | Ser | Ser | Ala | Ser | Thr | Ile | Thr | Ser | Pro | Val | Ser | Pro |
| 225 |     |     |     |     | 230 |     |     |     |     | 235 |     |     |     |     | 240 |
| Ile | His | Thr | Pro | Pro | Pro | Ala | Pro | Met | Ile | Pro | Ser | Thr | Ser | Lys | Gly |
|     |     |     |     | 245 |     |     |     |     | 250 |     |     |     |     | 255 |     |
| Lys | Thr | Pro | Lys | Ala | Pro | Arg | Thr |
|     |     |     | 260 |     |     |     |     |

( 2 ) INFORMATION FOR SEQ ID NO:94:

( i ) SEQUENCE CHARACTERISTICS:
      ( A ) LENGTH: 342 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:94:

| GAGCTCGGAT | GAGATCACGA | TGATCCGTGG | CGTTCACCAC | GACAGGCTCC | GAGTAAACCA | 60  |
| TGGAATCCGA | TGCCCCGTAG | GCCGAGTCCA | GAAACGAGGC | GAAGCTGAAC | CCCAGCTCGC | 120 |
| AGATCACGGC | GTCGCTGAGC | AAGTGGTCTT | TCTCCAGACT | GCTCAGCTTC | TGGCTCGTGT | 180 |
| ACCCGAAGTT | CTTGTGCGGA | GCCAGCTTCA | CGGACTGCTG | GCTGTCGTTC | ACGAACTTCA | 240 |
| GGGCCGCTTC | GATCAGCACC | TTGGTCTCTG | AGAAGCGCAC | CTGGCACCAC | GAAGTGTAAA | 300 |
| CATAGTAGAA | CAGGGTTTCC | ACCGCAGGCA | CGTACAATCC | CC         |            | 342 |

( 2 ) INFORMATION FOR SEQ ID NO:95:

( i ) SEQUENCE CHARACTERISTICS:
      ( A ) LENGTH: 355 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:95:

-continued

```
GAGCTCGAAT GAGATCACGA TGATCCGTGG CGTTCACCAC GACAGGCTCC GAGTAAACCA        60

TGGAATCCGA TACCCCGTAG GCCGAGTCCA GAAACGAGGC GAAACTGAAC CCCAGCTCGC       120

AGATCACGGC GTCGCTGAGC AAGTGGTCTT TTTCCAGACT GGTCAGCTTC TGGGTCGTGT       180

ACCCGAAGTT CTTGTGCGGA GCCAGCTTGA CGGACTGCTG GCTGTCGTTC ACGAACTTCA       240

GGGCCGCTTC GATCAAGCAC CTTGGGTCTC TGAGTAAGGG CAGTTTGGCA CCACGAAGGT       300

TGTTAAACCA TAATAGAACA GGGTTTTCCC ACCCCGAAGG CAAGGTCCAA TCCCC           355
```

( 2 ) INFORMATION FOR SEQ ID NO:96:

( i ) SEQUENCE CHARACTERISTICS:
( A ) LENGTH: 348 base pairs
( B ) TYPE: nucleic acid
( C ) STRANDEDNESS: single
( D ) TOPOLOGY: linear ( x i ) SEQUENCE DESCRIPTION: SEQ ID NO:96:

```
GCGCGCGGAT CAGATCGCGG TGATCGGTTG CGTTGGTCAC TAAAGGCTCG GAAAAGAGCA        60

TAGATTCGGC AGGTTGGTAA GCCGAATCGA AAAACGAGGC AAAACTGAAG GCCAACTCGC       120

AAACCACCGC GTCACTCAGC AGATGATCCT TTTCCAGACT GCTGAGTCGC TGGCTCATGT       180

ACCCCAAGCG CTTATGTGGC GCCAGCTTCA CCGACTGCTG ACTGTCGTGC ACAAACCGCA       240

ACGCCGCCTC GATCAGCACA CGCGGCTCCG AGAAGCGCAG ATTGACACCA TGACGTGTAC       300

ACGTAGTAGA AAAGCGTCTC GCCGGCCGGC ACGTAGAGCC CTCGCGCC                   348
```

( 2 ) INFORMATION FOR SEQ ID NO:97:

( i ) SEQUENCE CHARACTERISTICS:
( A ) LENGTH: 49 amino acids
( B ) TYPE: amino acid
( C ) STRANDEDNESS: single
( D ) TOPOLOGY: linear ( x i ) SEQUENCE DESCRIPTION: SEQ ID NO:97:

```
Met Leu Ser Asp Ala Val Ile Cys Glu Leu Gly Phe Ser Phe Ala Ser
 1               5                  10                  15

Val Phe Leu Asp Ser Ala Tyr Gly Val Ser Asp Ser Met Val Tyr Ser
                20                  25                  30

Glu Trp Pro Val Val Val Asn Ala Thr Asp His Arg Asp Leu Ile Arg
                35                  40                  45

Ala
```

( 2 ) INFORMATION FOR SEQ ID NO:98:

( i ) SEQUENCE CHARACTERISTICS:
( A ) LENGTH: 48 amino acids
( B ) TYPE: amino acid
( C ) STRANDEDNESS: single
( D ) TOPOLOGY: linear ( x i ) SEQUENCE DESCRIPTION: SEQ ID NO:98:

```
Met Leu Ser Asp Ala Val Ile Cys Glu Leu Gly Phe Ser Phe Ala Ser
 1               5                  10                  15

Val Phe Leu Asp Ser Ala Tyr Gly Ser Asp Ser Met Val Tyr Ser Glu
                20                  25                  30

Trp Pro Val Val Val Asn Ala Thr Asp His Arg Asp Leu Ile Arg Ala
                35                  40                  45
```

( 2 ) INFORMATION FOR SEQ ID NO:99:

( i ) SEQUENCE CHARACTERISTICS:
  ( A ) LENGTH: 38 amino acids
  ( B ) TYPE: amino acid
  ( C ) STRANDEDNESS: single
  ( D ) TOPOLOGY: linear ( x i ) SEQUENCE DESCRIPTION: SEQ ID NO:99:

```
Met Leu Ser Asp Ala Val Cys Glu Leu Phe Ser Phe Ala Ser Val Phe
 1               5                  10                  15
Asp Ser Ala Tyr Ser Met Ser Glu Trp Pro Val Asn Ala Thr Asp His
             20                  25                  30
Arg Asp Leu Ile Arg Ala
             35
```

( 2 ) INFORMATION FOR SEQ ID NO:100:

( i ) SEQUENCE CHARACTERISTICS:
  ( A ) LENGTH: 24 amino acids
  ( B ) TYPE: amino acid
  ( C ) STRANDEDNESS: single
  ( D ) TOPOLOGY: linear ( x i ) SEQUENCE DESCRIPTION: SEQ ID NO:100:

```
Met Asp Ala Val Glu Leu Phe Ser Ala Ser Leu Asp Ser Tyr Ser Glu
 1               5                  10                  15
Trp Pro Val Asn Ala His Asp Leu
             20
```

( 2 ) INFORMATION FOR SEQ ID NO:101:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( x i ) SEQUENCE DESCRIPTION: SEQ ID NO:101:

```
Met Leu Asp Val Glu Leu Phe Ser Leu Asp Ser Tyr Ser Met Trp Pro
 1               5                  10                  15
Asn His
```

( 2 ) INFORMATION FOR SEQ ID NO:102:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( x i ) SEQUENCE DESCRIPTION: SEQ ID NO:102:

```
Met Asp Val Glu Leu Ser Phe Asp Ser Tyr Trp Pro Val
 1               5                  10
```

( 2 ) INFORMATION FOR SEQ ID NO:103:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( x i ) SEQUENCE DESCRIPTION: SEQ ID NO:103:

```
Met Asp Cys Glu Leu Ser Ala Leu Ser Tyr Trp Pro
 1               5                  10
```

( 2 ) INFORMATION FOR SEQ ID NO:104:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( x i ) SEQUENCE DESCRIPTION: SEQ ID NO:104:

| Met | Asp | Glu | Leu | Ser | Phe | Leu | Tyr | Trp | Pro | Ala | Asp | Ile | Ala |
|-----|-----|-----|-----|-----|-----|-----|-----|-----|-----|-----|-----|-----|-----|
| 1 | | | | 5 | | | | | 10 | | | | |